United States Patent
Parham et al.

(10) Patent No.: US 10,500,286 B2
(45) Date of Patent: Dec. 10, 2019

(54) CCK2R-DRUG CONJUGATES

(71) Applicant: ENDOCYTE, INC., West Lafayette, IN (US)

(72) Inventors: Garth L. Parham, Largo, FL (US); Melissa Nelson, Delphi, IN (US); Marilynn Vetzel, Rossville, IN (US); Christina M. Dircksen, West Lafayette, IN (US); Joseph Anand Reddy, West Lafayette, IN (US); Christopher Paul Leamon, West Lafayette, IN (US); Iontcho Radoslavov Vlahov, West Lafayette, IN (US)

(73) Assignee: Endocyte, Inc., West Lafayette, IN (US)

( * ) Notice: Subject to any disclaimer, the term of this patent is extended or adjusted under 35 U.S.C. 154(b) by 0 days.

(21) Appl. No.: 15/751,633

(22) PCT Filed: Aug. 10, 2016

(86) PCT No.: PCT/US2016/046292
§ 371 (c)(1),
(2) Date: Feb. 9, 2018

(87) PCT Pub. No.: WO2017/030859
PCT Pub. Date: Feb. 23, 2017

(65) Prior Publication Data
US 2018/0228909 A1 Aug. 16, 2018

Related U.S. Application Data

(60) Provisional application No. 62/205,411, filed on Aug. 14, 2015, provisional application No. 62/261,227, filed on Nov. 30, 2015, provisional application No. 62/323,287, filed on Apr. 15, 2016.

(51) Int. Cl.
| | | |
|---|---|---|
| *A61K 47/64* | (2017.01) | |
| *A61K 38/03* | (2006.01) | |
| *C07D 243/12* | (2006.01) | |
| *A61P 35/00* | (2006.01) | |
| *A61K 31/5513* | (2006.01) | |
| *A61K 38/07* | (2006.01) | |
| *A61K 49/00* | (2006.01) | |
| *C07D 405/14* | (2006.01) | |
| *A61K 51/08* | (2006.01) | |
| *C07D 417/14* | (2006.01) | |
| *C07D 209/20* | (2006.01) | |
| *A61K 47/54* | (2017.01) | |
| *A61K 38/14* | (2006.01) | |

(52) U.S. Cl.
CPC .......... *A61K 47/64* (2017.08); *A61K 31/5513* (2013.01); *A61K 38/03* (2013.01); *A61K 38/07* (2013.01); *A61K 47/545* (2017.08); *A61K 49/00* (2013.01); *A61K 51/088* (2013.01); *A61P 35/00* (2018.01); *C07D 209/20* (2013.01); *C07D 243/12* (2013.01); *C07D 405/14* (2013.01); *C07D 417/14* (2013.01); *A61K 38/14* (2013.01)

(58) Field of Classification Search
CPC .. A61K 49/0002; A61K 51/088; A61K 51/08; C07D 407/12
See application file for complete search history.

(56) References Cited

FOREIGN PATENT DOCUMENTS

WO WO2013126797 8/2013

OTHER PUBLICATIONS

PCT Search Report and Written Opinion for PCT/US2016/046292, completed Sep. 20, 2016.
Roosenburg, Susan, et al., "Radiolabeled CCK/Gastrin Peptides for Imaging and Therapy of CCK2 Receptor-Expressing Tumors," 2010, Amino Acids; The Forum for Amino Acid and Protein Research, vol. 41, No. 5, pp. 1049-1058.
Correia, Joao, D. G., et al., "Radiopharmaceuticals for Imaging and Therapy," 2011, Dalton Transactions: the International journal for inorganic, organometallic and bioinorganic chemistry, vol. 40, No. 23, pp. 6144-6167.
Reddy, J. A., et al., "Folate-Targeted, Cationic Liposome-Mediated Gene Transfer into Disseminated Peritoneal Tumors," 2002, Gene Therapy, vol. 9, No. 22, pp. 1542-1550.
Saad, Maha, et al., "Receptor Targeted Polymers, Dendrimers Liposomes: Which Nanocarrier is the Most Efficient for Tumor-Specific Treatment and Imaging?," 2008, Journal of Controlled Release, vol. 130, No. 2, pp. 107-114.

*Primary Examiner* — Kaipeen E Yang
(74) *Attorney, Agent, or Firm* — Barnes & Thornburg LLP

(57) ABSTRACT

The disclosure provided herein pertains to CCK2R-drug conjugates. In particular, the disclosure pertains to CCK2R-drug conjugates that target the delivery of drugs to a mammalian recipient. Also described are methods of making and using CCK2R-drug conjugates.

5 Claims, 8 Drawing Sheets

CCK2R-DRUG CONJUGATES

CROSS REFERENCE TO RELATED APPLICATIONS

This application is a U.S. national stage application under 35 U.S.C. § 371(b) of International Application No. PCT/US2016/046292 filed Aug. 10, 2016, which claims priority under 35 U.S.C. § 119(e) to U.S. Provisional Application Ser. No. 62/205,411, filed Aug. 14, 2015, U.S. Provisional Application Ser. No. 62/261,227, filed Nov. 30, 2015, and U.S. Provisional Application Ser. No. 62/323,287, filed Apr. 15, 2016, all of which are incorporated herein by reference in their entirety

TECHNICAL FIELD

The disclosure provided herein pertains to CCK2R-drug conjugates. In particular, the disclosure pertains to CCK2R-drug conjugates that target the delivery of drugs to a mammalian recipient. Also described are methods of making and using CCK2R-drug conjugates.

BACKGROUND

Cholecystokinin-2 receptors (also referred to as cholecystokinin-2 receptor, CCK2R, CCKBR or $CCK_2$) are regulatory peptides of the brain and gastrointestinal tract. CCK2R has been demonstrated to be overexpressed in certain human cancers. For example, CCK2R splice variants have been observed in human gastrointestinal and lung tumors. (See Korner, M. et al., *J. Cell Mol. Med.*, 14, 4, 933-43 (2010)). Natural substrates of high affinity for cholecystokinin receptors include peptide hormones CCK and gastrin. C-terminal CCK peptide amide is selectively targeting CCK2R with 2 times higher affinity than binding to CCK1R. CCK2R has also been implicated in leukemia through immunoblotting of several leukemia cells lines. (See Stubbs, M. et al., *Oncol. Rep.*, 14, 4, 1055-8 (2005).

The targeted delivery of drugs has been of recent interest, especially in the area of cancer therapy. Among the most well studied drug conjugates are anti-body drug conjugates (also known as ADCs) that have been designed as targeted therapies for cancer. (See Ducry, L. et al., *Bioconjugate Chemistry*, 21, 1, 5-13 (2010)). Examples of approved ADC treatments for cancer include Adcetris®, and Kadcyla®. Another promising avenue for the targeted delivery of drugs that has gained significant interest is the delivery of drug conjugates to a target cell through the binding of a receptor with a ligand. One example of such an approach is the delivery of a drug conjugate to a vitamin receptor through a vitamin receptor binding ligand. See for example, drug conjugates of folate described in U.S. Pat. No. 7,601,332.

The development of novel drug conjugates for delivery of therapeutic agents to molecular targets associated with cancer cells continues to be of great interest. Here we report the design and synthesis of novel CCK2-receptor drug conjugates.

SUMMARY

In one aspect, the disclosure provides conjugates of the formula A-L-B, or a pharmaceutically acceptable salt thereof, wherein A is a drug (D) or an imaging agent (I), L is a linker, and B is a binding ligand of CCK2R.

In one aspect, the disclosure provides conjugates of the formula D-L-B, or a pharmaceutically acceptable salt thereof, wherein D is a drug, L is a linker comprising at least one releasable linker ($L^1$), and B is a binding ligand of CCK2R.

In one aspect, the disclosure provides conjugates of the formula I-L-B, or a pharmaceutically acceptable salt thereof, wherein I is an imaging, L is a linker, and B is a binding ligand of CCK2R.

In another aspect, the disclosure provides pharmaceutical compositions comprising a therapeutically effective amount of the conjugates described herein, or a pharmaceutically acceptable salt thereof, and at least on excipient.

In another aspect, the disclosure provides a method of treating abnormal cell growth in a mammal, including a human, the method comprising administering to the mammal any of the conjugates or compositions described herein.

In another aspect, the disclosure provides uses of conjugates or compositions as described herein in the preparation of medicament for treating abnormal cell growth in a mammal.

In another aspect, the disclosure provides conjugates or compositions as described herein for the treatment abnormal cell growth in a mammal.

The conjugates of the present disclosure can be described as embodiments in any of the following enumerated clauses. It will be understood that any of the embodiments described herein can be used in connection with any other embodiments described herein to the extent that the embodiments do not contradict one another.

1. A conjugate of the formula A-L-B, or a pharmaceutically acceptable salt thereof, wherein A is a drug (D) or imaging agent (I), L is a linker, and B is a binding ligand of CCK2R.

1a. A conjugate of the formula D-L-B, or a pharmaceutically acceptable salt thereof, wherein D is a drug, L is a linker comprising at least one releasable linker ($L^1$), and B is a binding ligand of CCK2R.

1b. A conjugate of the formula I-L-B, or a pharmaceutically acceptable salt thereof, wherein I is an imaging agent, L is a linker, and B is a binding ligand of CCK2R.

1c. The conjugate of clause 1, having the formula

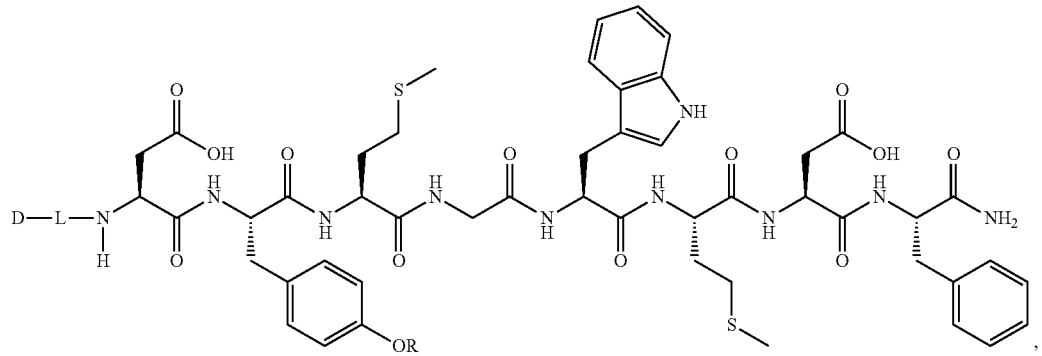

wherein R is H, $SO_3^-$ or $SO_3^M$, wherein M is a counter-ion, L is a linker comprising a disulfide moiety, and D is a drug, or a pharmaceutically acceptable salt thereof.

1d. The conjugate of clause 1, having the formula

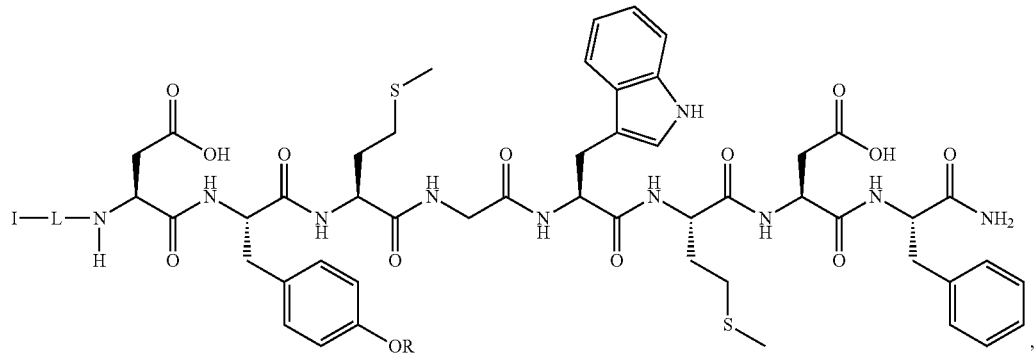

wherein R is H, $SO_3^-$ or $SO_3^M$, wherein M is a counter-ion, L is a linker, and I is an imaging agent, or a pharmaceutically acceptable salt thereof.

1e. The conjugate of clause 1, having the formula

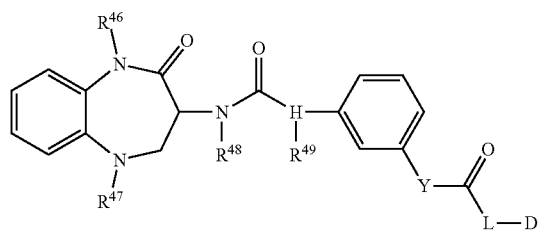

wherein
Y is a bond or a $C_1$-$C_6$ alkyl;
each of $R^{46}$, $R^{47}$, $R^{48}$ and $R^{49}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, $-OR^{50}$, $-OC(O)R^{50}$, $-OC(O)NR^{50}R^{50'}$, $-OS(O)R^{50}$, $-OS(O)_2R^{50}$, $-SR^{50}$, $-S(O)R^{50}$, $-S(O)_2R^{50}$, $-S(O)NR^{50}R^{50'}$, $-S(O)_2NR^{50}R^{50'}$, $-OS(O)NR^{50}R^{50'}$, $-OS(O)_2NR^{50}R^{50'}$, $-NR^{50}R^{50'}$, $-NR^{50}C(O)R^{51}$, $-NR^{50}C(O)OR^{51}$, $-NR^{50}C(O)NR^{51}R^{51'}$, $-NR^{50}S(O)R^{51}$, $-NR^{50}S(O)_2R^{51}$, $-NR^{50}S(O)NR^{51}R^{51'}$, $-NR^{50}S(O)_2NR^{51}R^{51'}$, $-C(O)R^{50}$, $-C(O)OR^{50}$ or $-C(O)NR^{50}R^{50'}$; and each $R^{50}$, $R^{50'}$, $R^{51}$ and $R^{51'}$ is independently H, $C_1$-$C_6$ alkyl, $C_2$-$C_6$ alkenyl, $C_2$-$C_6$ alkynyl or $C_3$-$C_6$ cycloalkyl;

L is a linker comprising a disulfide moiety, and D is a drug, or a pharmaceutically acceptable salt thereof.

2. The conjugate of clause 1 to 1e, or a pharmaceutically acceptable salt thereof, wherein R is H.

3. The conjugate of clause 1 to 1e, or a pharmaceutically acceptable salt thereof, wherein R is $SO_3^-$ or $SO_3M$, wherein M is a counter-ion.

4. The conjugate of any one of clauses 1 to 3, or a pharmaceutically acceptable salt thereof, wherein L further comprises a polyether moiety.

5. The conjugate of any one of the preceding clauses, or a pharmaceutically acceptable salt thereof, wherein L further comprises a hydrazine moiety.

6. The conjugate of any one of the preceding clauses, wherein L further comprises one or more amino acids.

7. The conjugate of clause 6, or a pharmaceutically acceptable salt thereof, wherein at least one amino acid is in the D-configuration.

8. The conjugate of clause 6, or a pharmaceutically acceptable salt thereof, wherein at least one amino acid is in the L-configuration.

9. The conjugate of any one of the preceding clauses, or a pharmaceutically acceptable salt thereof, wherein L further comprises one or more amino acids selected from the group consisting of L-asparagine, L-arginine, L-glycine, L-aspartic acid, L-glutamic acid, L-glutamine, L-cysteine, L-alanine, L-valine, L-leucine, L-isoleucine, 3-amino-L-alanine, D-asparagine, D-arginine, D-glycine, D-aspartic acid, D-glutamic acid, D-glutamine, D-cysteine, D-alanine, D-valine, D-leucine, D-isoleucine and 3-amino-D-alanine.

10. The conjugate of any one of the preceding clauses, or a pharmaceutically acceptable salt thereof, wherein L further comprises at least two amino acids selected from the group consisting of L-asparagine, L-arginine, L-glycine, L-aspartic acid, L-glutamic acid, L-glutamine, L-cysteine, L-alanine, L-valine, L-leucine, L-isoleucine and 3-amino-L-alanine.

11. The conjugate of any one of the preceding clauses, or a pharmaceutically acceptable salt thereof, wherein D is a drug selected from the group consisting of a vinca alkaloid, a cryptophycin, bortezomib, thiobortezomib, a tubulysin, aminopterin, rapamycin, paclitaxel, docetaxel, doxorubicin, daunorubicin, everolimus, α-amanatin, verucarin, didemnin B, geldanomycin, purvalanol A, ispinesib, budesonide, dasatinib, an epothilone, a maytansine, and a tyrosine kinase inhibitor.

12. The conjugate of any one of the preceding clauses, or a pharmaceutically acceptable salt thereof, wherein D, when present, is a tubulysin.

13. The conjugate of any one of the preceding clauses, or a pharmaceutically acceptable salt thereof, wherein D, when present, is a tetrapeptide of the formula I

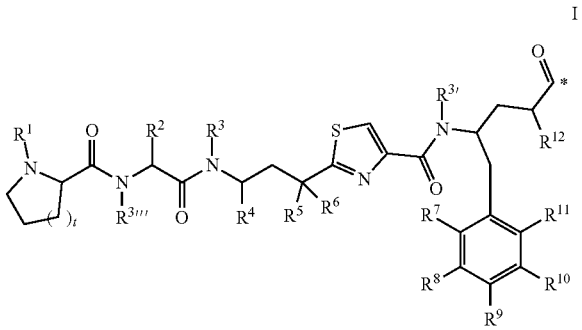

I wherein $R^1$, $R^3$, $R^{3'}$ and $R^{3''}$ are each independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{13}$, —$OC(O)R^{13}$, —$OC(O)NR^{13}R^{13'}$, —$OS(O)R^{13}$, —$OS(O)_2R^{13}$, —$SR^{13}$, —$SC(O)R^{13}$, —$S(O)R^{13}$, —$S(O)_2R^{13}$, —$S(O)_2OR^{13}$, —$S(O)NR^{13}R^{13'}$, —$S(O)_2NR^{13}R^{13'}$, —$OS(O)NR^{13}R^{13'}$, —$OS(O)_2NR^{13}R^{13'}$, —$NR^3R^{3'}$, —$NR^{13}C(O)R^{14}$, —$NR^{13}C(O)OR^{14}$, —$NR^{13}C(O)NR^{14}R^{14'}$, —$NR^{13}S(O)R^{14}$, —$NR^{13}S(O)_2R^{14}$, —$NR^{13}S(O)NR^{13}R^{14}$, —$NR^{13}S(O)_2NR^{14}R^{14'}$, —$P(O)(OR^{13})_2$, —$C(O)R^{13}$, —$C(O)OR^{13}$ or —$C(O)NR^{13}R^{13'}$;

$R^2$, $R^4$ and $R^{12}$ are each independently selected from the group consisting of H, $C_1$-$C_6$ alkyl, $C_2$-$C_6$ alkenyl, $C_2$-$C_6$ alkynyl;

$R^5$ and $R^6$ are each independently selected from the group consisting of H, halogen, $C_1$-$C_6$ alkyl, $C_2$-$C_6$ alkenyl, $C_2$-$C_6$ alkynyl, —$OR^{15}$, —$SR^{15}$, —$OC(O)R^{15}$, —$OC(O)NR^{15}R^{15'}$, and —$NR^{15}R^{15'}$, wherein each hydrogen atom in $C_1$-$C_6$ alkyl, $C_2$-$C_6$ alkenyl and $C_2$-$C_6$ alkynyl is independently optionally substituted by halogen, —$OR^{16}$, —$SR^{16}$, —$NR^{16}R^{16'}$, $C(O)R^{16}$, —$C(O)OR^{16}$ or —$C(O)NR^{16}R^{16'}$; or $R^5$ and $R^6$ taken together with the carbon atom to which they are attached form a —C(O)—;

each $R^7$, $R^8$, $R^9$, $R^{10}$ and $R^{11}$ is independently selected from the group consisting of H, halogen, $C_1$-$C_6$ alkyl, $C_2$-$C_6$ alkenyl, $C_2$-$C_6$ alkynyl, —CN, —$NO_2$, —NCO, —$OR^{17}$, —$SR^{17}$, —$S(O)_2OR^{17}$, —$NR^{17}R^{17'}$, —$P(O)(OR^{17})_2$, —$C(O)R^{17}$, —$C(O)OR^{17}$ and —$C(O)NR^{17}R^{17'}$, wherein each hydrogen atom in $C_1$-$C_6$ alkyl, $C_2$-$C_6$ alkenyl and $C_2$-$C_6$ alkynyl is independently optionally substituted by halogen, —$OR^{18}$, —$SR^{18}$, —$NR^{18}R^{18'}$, —$C(O)R^{18}$, —$C(O)OR^{18}$ or —$C(O)NR^{18}R^{18'}$;

each $R^{13}$, $R^{13'}$, $R^{14}$, $R^{14'}$, $R^{15}$, $R^{15'}$, $R^{16}$, $R^{16'}$, $R^{17}$ and $R^{17'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by halogen, —OH, —SH, —$NH_2$ or —$CO_2H$;

each $R^{18}$ and $R^{18'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl —$C(O)R^{19}$, —$P(O)(OR^{19})_2$, and —$S(O)_2OR^{19}$;

each $R^{19}$ is independently selected from H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl; and t is 1, 2 or 3, wherein * is a covalent bond.

14. The conjugate of clause 13, or a pharmaceutically acceptable salt thereof, wherein t is 2.

15. The conjugate of clause 13 or 14, or a pharmaceutically acceptable salt thereof, wherein $R^{1a}$ is $C_1$-$C_6$ alkyl.

16. The conjugate of any one of clauses 13 to 15, or a pharmaceutically acceptable salt thereof, wherein $R^1$ is methyl.

17. The conjugate of any one of clauses 13 to 16, or a pharmaceutically acceptable salt thereof, wherein $R^2$ is $C_1$-$C_6$ alkyl.

18. The conjugate of any one of clauses 13 to 17, or a pharmaceutically acceptable salt thereof, wherein $R^2$ is sec-butyl.

19. The conjugate of any one of clauses 13 to 18, or a pharmaceutically acceptable salt thereof, wherein $R^3$ is $C_1$-$C_6$ alkyl, wherein each hydrogen atom in $C_1$-$C_6$ alkyl is independently optionally substituted by —$OC(O)R^{13}$ and wherein $R^{13}$ is $C_1$-$C_6$ alkyl.

20. The conjugate of any one of clauses 13 to 19, or a pharmaceutically acceptable salt thereof, wherein $R^4$ is $C_1$-$C_6$ alkyl.

21. The conjugate of any one of clauses 13 to 20, or a pharmaceutically acceptable salt thereof, wherein $R^4$ is isopropyl.

22. The conjugate of any one of clauses 13 to 21, or a pharmaceutically acceptable salt thereof, wherein $R^5$ is —$OC(O)R^{15}$.

23. The conjugate of clause 22, or a pharmaceutically acceptable salt thereof, wherein $R^{15}$ is methyl.

24. The conjugate of any one of clauses 13 to 23, or a pharmaceutically acceptable salt thereof, wherein $R^6$ is H.

25. The conjugate of any one of clauses 13 to 24, or a pharmaceutically acceptable salt thereof, wherein $R^7$, $R^8$, $R^{10}$ and $R^{11}$ are H.

26. The conjugate of any one of clauses 13 to 25, or a pharmaceutically acceptable salt thereof, wherein $R^7$ is —OH.

27. The conjugate of any one of clauses 13 to 26, or a pharmaceutically acceptable salt thereof, wherein $R^{12}$ is $C_1$-$C_6$ alkyl.

28. The conjugate of any one of clauses 13 to 27, or a pharmaceutically acceptable salt thereof, wherein $R^{12}$ is methyl.

29. The conjugate of any one of clauses 13 to 28, or a pharmaceutically acceptable salt thereof, wherein $R^{3'}$ and $R^{3''}$ are H.

30. The conjugate of any one of clauses 13 to 29, or a pharmaceutically acceptable salt thereof, wherein D is a tetrapeptide of the formula

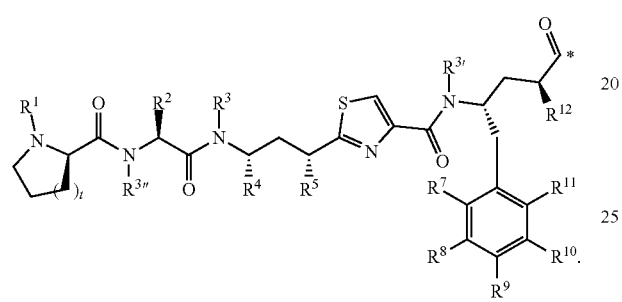

31. The conjugate of any one of clauses 13 to 30, or a pharmaceutically acceptable salt thereof, wherein D is a tetrapeptide of the formula

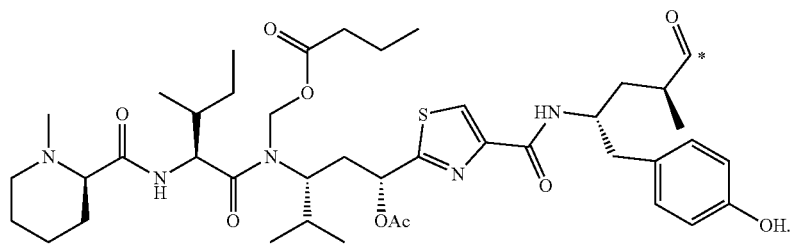 [SMILES: CCCC(=O)OCN(C(=O)[C@@H](NC(=O)[C@H]1CCCCN1C)C(C)CC)[C@H](C[C@@H](OC(C)=O)c1nc(C(=O)N[C@@H](Cc2ccc(O)cc2)C[C@H](C)C=O)cs1)C(C)C]

32. The conjugate of any one of the preceding clauses, or a pharmaceutically acceptable salt thereof, wherein L comprises a moiety $L^1$ of the formula selected from the group consisting of

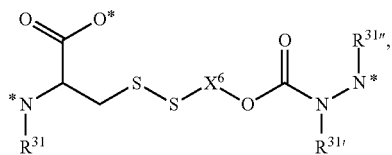

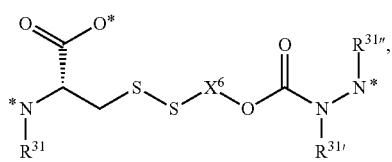

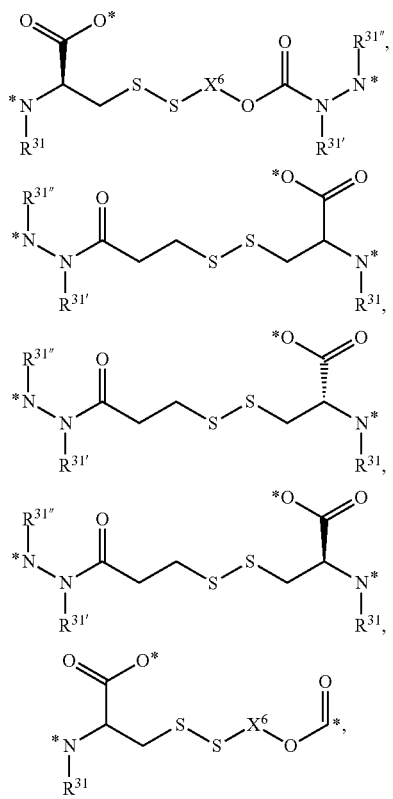

-continued

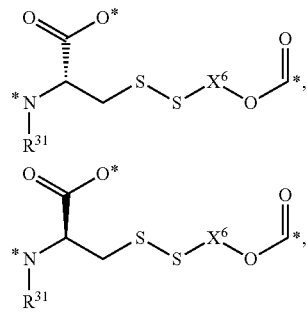

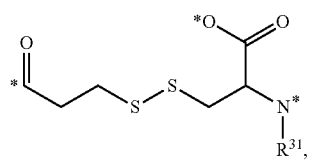

-continued

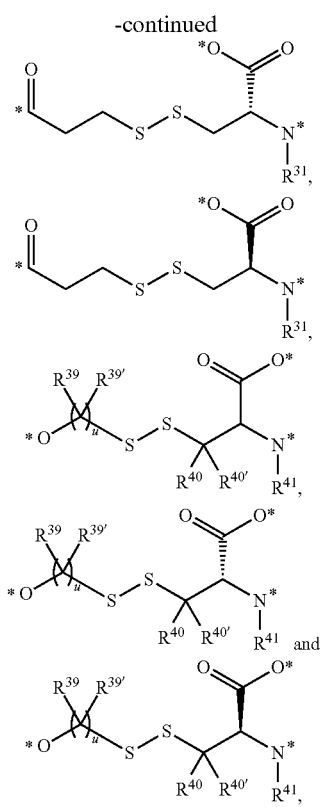

wherein each $R^{31}$, $R^{31'}$ and $R^{31''}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{32}$, $OC(O)R^{32}$, —$OC(O)NR^{32}R^{32'}$, —$OS(O)R^{32}$, —$OS(O)_2R^{32}$, —$SR^{32}$, —$S(O)R^{32}$, —$S(O)_2R^{32}$, —$S(O)NR^{32}R^{32'}$, —$S(O)_2NR^{32}R^{32'}$, —$OS(O)NR^{32}R^{32'}$, —$OS(O)_2NR^{32}R^{32'}$, —$NR^{32}R^{32'}$, —$NR^{32}C(O)R^{33}$, —$NR^{32}C(O)OR^{33}$, —$NR^{32}C(O)NR^{33}R^{33'}$, —$NR^{32}S(O)R^{33}$, —$NR^{32}S(O)_2R^{33}$, —$NR^{32}S(O)NR^{33}R^{33'}$, —$NR^{32}S(O)_2NR^{33}R^{33'}$, —$NR^{34}C(O)R^{32}$, —$C(O)OR^{32}$ or —$C(O)NR^{32}R^{32'}$;

each $X^6$ is independently $C_1$-$C_6$ alkyl or $C_6$-$C_{10}$ aryl($C_1$-$C_6$ alkyl), wherein each hydrogen atom in $C_1$-$C_6$ alkyl and $C_6$-$C_{10}$ aryl($C_1$-$C_6$ alkyl) is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{34}$, —$OC(O)R^{34}$, —$OC(O)NR^{34}R^{34'}$, —$OS(O)R^{34}$, —$OS(O)_2R^{34}$, —$SR^{34}$, —$S(O)R^{34}$, —$S(O)_2R^{34}$, —$S(O)NR^{34}R^{34'}$, —$S(O)_2NR^{34}R^{34'}$, —$OS(O)NR^{34}R^{34'}$, —$OS(O)_2NR^{34}R^{34'}$, —$NR^{34}R^{34'}$, —$NR^{34}C(O)R^{35}$, —$NR^{34}C(O)OR^{35}$, —$NR^{34}C(O)NR^{35}R^{35'}$, —$NR^{34}S(O)R^{35}$, —$NR^{34}S(O)_2R^{35}$, —$NR^{34}S(O)NR^{35}R^{35'}$, —$NR^{34}S(O)_2NR^{35}R^{35'}$, —$C(O)R^{34}$, —$C(O)OR^{34}$ or —$C(O)NR^{34}R^{34'}$;

each $R^{32}$, $R^{32'}$, $R^{33}$, $R^{33'}$, $R^{34}$, $R^{34'}$, $R^{35}$ and $R^{35'}$ is independently selected from the group consisting of H, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl;

each $R^{39}$, $R^{39'}$, $R^{40}$ and $R^{40'}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{44}$, —$OC(O)R^{44}$, —$OC(O)NR^{44}R^{44'}$, —$OS(O)R^{44}$, —$OS(O)_2R^{44}$, —$SR^{44}$, —$S(O)R^{44}$, —$S(O)_2R^{44}$, —$S(O)NR^{44}R^{44'}$, —$S(O)_2NR^{44}R^{44'}$, —$OS(O)NR^{44}R^{44'}$, —$OS(O)_2NR^{44}R^{44'}$, —$NR^{44}R^{44'}$, —$NR^{44}C(O)R^{45}$, —$NR^{44}C(O)OR^{45}$, —$NR^4C(O)NR^{45}R^{45'}$, —$NR^{44}S(O)R^{45}$, —$NR^{44}S(O)_2R^{45}$, —$NR^{44}S(O)NR^{45}R^{45'}$, —$NR^{44}S(O)_2NR^{45}R^{45'}$, —$C(O)R^{44}$, —$C(O)OR^{44}$ or —$C(O)NR^{44}R^{44'}$;

each $R^{41}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{42}$, $OC(O)R^{42}$, —$OC(O)NR^{42}R^{42'}$, —$OS(O)R^{42}$, —$OS(O)_2R^{42}$, —$SR^{42}$, —$S(O)R^{42}$, $S(O)_2R^{42}$, —$S(O)NR^{42}R^{42'}$, —$S(O)_2NR^{42}R^{42'}$, —$OS(O)NR^{42}R^{42'}$, —$OS(O)_2NR^{42}R^{42'}$, —$NR^{42}R^{42'}$, —$NR^{42}C(O)R^{43}$, —$NR^{42}C(O)OR^{43}$, —$NR^{42}C(O)NR^{43}R^{43'}$, —$NR^{42}S(O)R^{43}$, —$NR^{42}S(O)_2R^{43}$, —$NR^{42}S(O)NR^{43}R^{43'}$, —$NR^{42}S(O)_2NR^{43}R^{43'}$, —$C(O)R^{42}$, —$C(O)OR^{42}$ or —$C(O)NR^{42}R^{42'}$;

each $R^{42}$, $R^{42'}$, $R^{43}$, $R^{43'}$, $R^{44}$, $R^{44'}$, $R^{45}$, and $R^{45'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl; and u is 1, 2, 3 or 4;

wherein * is a covalent bond.

32a. The conjugate of any one of the preceding clauses, or a pharmaceutically acceptable salt thereof, wherein L comprises a moiety $L^1$ of the formula selected from the group consisting of

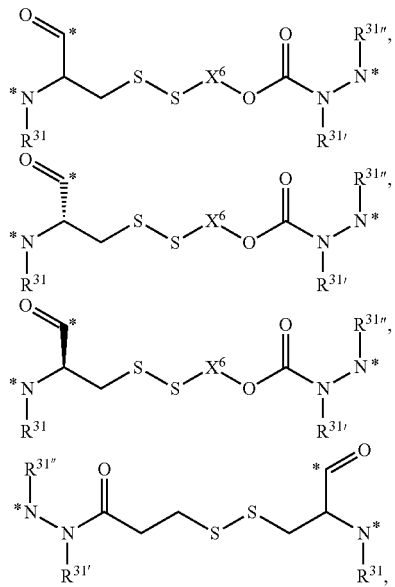

-continued

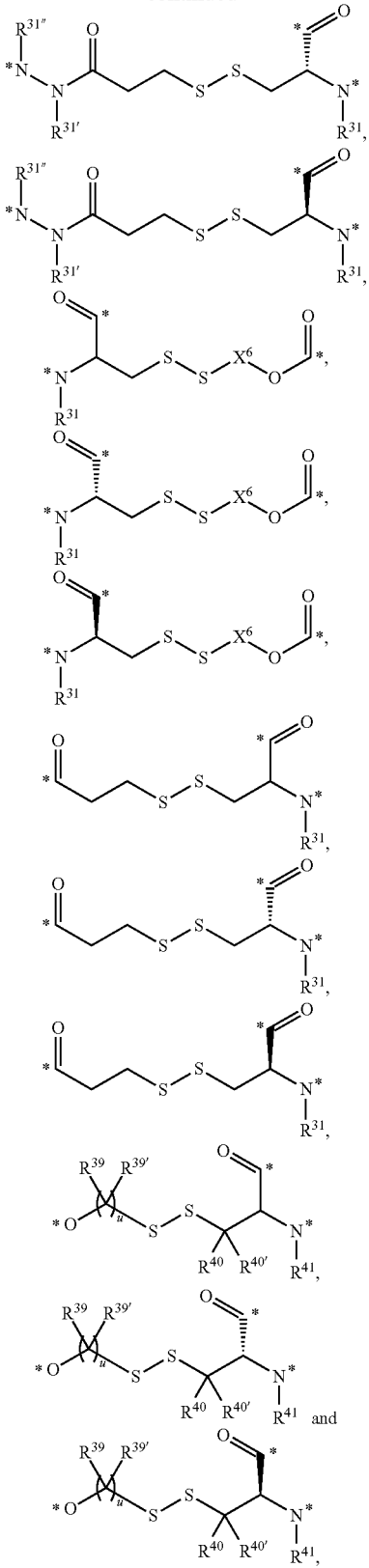

wherein
each $R^{31}$, $R^{31'}$ and $R^{31''}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{32}$, $OC(O)R^{32}$, —$OC(O)NR^{32}R^{32'}$, —$OS(O)R^{32}$, —$OS(O)_2R^{32}$, —$SR^{32}$, —$S(O)R^{32}$, —$S(O)_2R^{32}$, —$S(O)NR^{32}R^{32'}$, —$S(O)_2NR^{32}R^{32'}$, —$OS(O)NR^{32}R^{32'}$, —$OS(O)_2NR^{32}R^{32'}$, —$NR^{32}R^{32'}$, —$NR^{32}C(O)R^{33}$, —$NR^{32}C(O)OR^{33}$, —$NR^{32}C(O)NR^{33}R^{33'}$, —$NR^{32}S(O)R^{33}$, —$NR^{32}S(O)_2R^{33}$, —$NR^{32}S(O)NR^{33}R^{33'}$, —$NR^{32}S(O)_2NR^{33}R^{33'}$, —$C(O)R^{32}$, —$C(O)OR^{32}$ or —$C(O)NR^{32}R^{32'}$;

each $X^6$ is independently $C_1$-$C_6$ alkyl or $C_6$-$C_{10}$ aryl($C_1$-$C_6$ alkyl), wherein each hydrogen atom in $C_1$-$C_6$ alkyl and $C_6$-$C_{10}$ aryl($C_1$-$C_6$ alkyl) is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{34}$, —$OC(O)R^{34}$, —$OC(O)NR^{34}R^{34'}$, —$OS(O)R^{34}$, —$OS(O)_2R^{34}$, —$SR^{34}$, —$S(O)R^{34}$, —$S(O)_2R^{34}$, —$S(O)NR^{34}R^{34'}$, —$S(O)_2NR^{34}R^{34'}$, —$OS(O)NR^{34}R^{34'}$, —$OS(O)_2NR^{34}R^{34'}$, —$NR^{34}R^{34'}$, —$NR^{34}C(O)R^{35}$, —$NR^{34}C(O)OR^{35}$, —$NR^{34}C(O)NR^{35}R^{35'}$, —$NR^{34}S(O)R^{35}$, —$NR^{34}S(O)_2R^{35}$, —$NR^{34}S(O)NR^{35}R^{35'}$, —$NR^{34}S(O)_2NR^{35}R^{35'}$, —$C(O)R^{34}$, —$C(O)OR^{34}$ or —$C(O)NR^{34}R^{34'}$;

each $R^{32}$, $R^{32'}$, $R^{33}$, $R^{33'}$, $R^{34}$, $R^{34'}$, $R^{35}$ and $R^{35'}$ is independently selected from the group consisting of H, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl;

each $R^{39}$, $R^{39'}$, $R^{40}$ and $R^{40'}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{44}$, —$OC(O)R^{44}$, —$OC(O)NR^{44}R^{44'}$, —$OS(O)R^{44}$, —$OS(O)_2R^{44}$, —$SR^{44}$, —$S(O)R^{44}$, —$S(O)_2R^{44}$, —$S(O)NR^{44}R^{44'}$, —$S(O)_2NR^{44}R^{44'}$, —$OS(O)NR^{44}R^{44'}$, —$OS(O)_2NR^{44}R^{44'}$, —$NR^{44}R^{44'}$, —$NR^{44}C(O)R^{45}$, $NR^{44}C(O)OR^{45}$, —$NR^{44}C(O)NR^{45}R^{45'}$, —$NR^{44}S(O)R^{45}$, —$NR^{44}S(O)_2R^{45}$, —$NR^{44}S(O)NR^{45}R^{45'}$, —$NR^{44}S(O)_2NR^{45}R^{45'}$, —$C(O)R^{44}$, —$C(O)OR^{44}$ or —$C(O)NR^{44}R^{44'}$;

each $R^{41}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{42}$, $OC(O)R^{42}$, —$OC(O)NR^{42}R^{42'}$, —$OS(O)R^{42}$, —$OS(O)_2R^{42}$, —$SR^{42}$, —$S(O)R^{42}$, —$S(O)_2R^{42}$, —$S(O)NR^{42}R^{42'}$, —$S(O)_2NR^{42}R^{42'}$, —$OS(O)NR^{42}R^{42'}$, —$OS(O)_2NR^{42}R^{42'}$, —$NR^{42}R^{42'}$, —$NR^{42}C(O)R^{43}$, —$NR^{42}C(O)OR^{43}$, —$NR^{42}C(O)NR^{43}R^{43'}$, —$NR^{42}S(O)R^{43}$, —$NR^{42}S(O)_2R^{43}$, —$NR^{42}S(O)NR^{43}R^{43'}$, —$NR^{42}S(O)_2NR^{43}R^{43'}$, —$C(O)R^{42}$, —$C(O)OR^{42}$ or —$C(O)NR^{42}R^{42'}$;

each $R^{42}$, $R^{42'}$, $R^{43}$, $R^{43'}$, $R^{44}$, $R^{44'}$, $R^{45}$, and $R^{45'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl; and
u is 1, 2, 3 or 4;
wherein * is a covalent bond.

33. The conjugate of any one of the preceding clauses, or a pharmaceutically acceptable salt thereof, wherein L comprises a moiety $L^1$ of the formula selected from the group consisting of

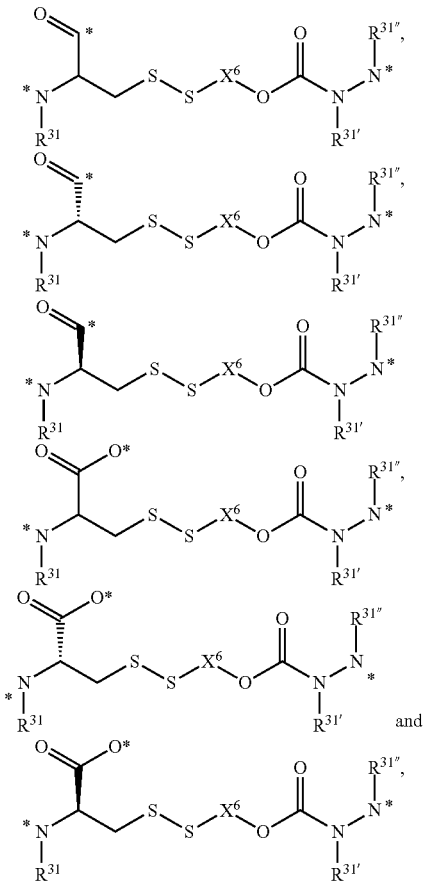

wherein each $R^{31}$, $R^{31'}$ and $R^{31''}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{32}$, $OC(O)R^{32}$, —$OC(O)NR^{32}R^{32'}$, —$OS(O)R^{32}$, —$OS(O)_2R^{32}$, —$SR^{32}$, —$S(O)R^{32}$, —$S(O)_2R^{32}$, —$S(O)NR^{32}R^{32'}$, —$S(O)_2NR^{32}R^{32'}$, —$OS(O)NR^{32}R^{32'}$, —$OS(O)_2NR^{32}R^{32'}$, —$NR^{32}R^{32'}$, —$NR^{32}C(O)R^{33}$, —$NR^{32}C(O)OR^{33}$, —$NR^{32}C(O)NR^{33}R^{33'}$, —$NR^{32}S(O)R^{33}$, —$NR^{32}S(O)_2R^{33}$, —$NR^{32}S(O)NR^{33}R^{33'}$, —$NR^{32}S(O)_2NR^{33}R^{33'}$, —$C(O)R^{32}$, —$C(O)OR^{32}$ or —$C(O)NR^{32}R^{32'}$;

each $X^6$ is independently $C_1$-$C_6$ alkyl or $C_6$-$C_{10}$ aryl($C_1$-$C_6$ alkyl), wherein each hydrogen atom in $C_1$-$C_6$ alkyl and $C_6$-$C_{10}$ aryl($C_1$-$C_6$ alkyl) is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{34}$, —$OC(O)R^{34}$, —$OC(O)NR^{34}R^{34'}$, —$OS(O)R^{34}$, —$OS(O)_2R^{34}$, —$SR^{34}$, —$S(O)R^{34}$, —$S(O)_2R^{34}$, —$S(O)NR^{34}R^{34'}$, —$S(O)_2NR^{34}R^{34'}$, —$OS(O)NR^{34}R^{34'}$, —$OS(O)_2NR^{34}R^{34'}$, —$NR^{34}R^{34'}$, —$NR^{34}C(O)R^{35}$, —$NR^{34}C(O)OR^{35}$, —$NR^{34}C(O)NR^{35}R^{35'}$, —$NR^{34}S(O)R^{35}$, —$NR^{34}S(O)_2R^{35}$, —$NR^{34}S(O)NR^{35}R^{35'}$, —$NR^{34}S(O)_2NR^{35}R^{35'}$, —$C(O)R^{34}$, —$C(O)OR^{34}$ or —$C(O)NR^{34}R^{34'}$;

each $R^{32}$, $R^{32'}$, $R^{33}$, $R^{33'}$, $R^{34}$, $R^{34'}$, $R^{35}$ and $R^{35'}$ is independently selected from the group consisting of H, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl.

34. The conjugate of clause 33, or a pharmaceutically acceptable salt thereof, wherein L comprises a moiety $L^1$ of the formula

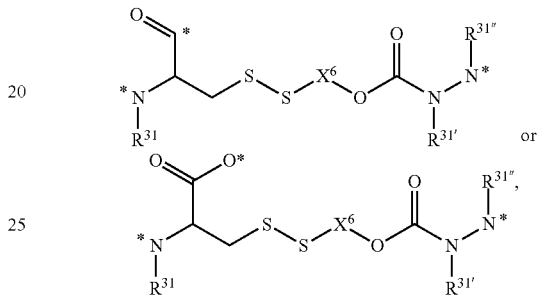

wherein each $R^{31}$, $R^{31'}$ and $R^{31''}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{32}$, $OC(O)R^{32}$, —$OC(O)NR^{32}R^{32'}$, —$OS(O)R^{32}$, —$OS(O)_2R^{32}$, —$SR^{32}$, —$S(O)R^{32}$, —$S(O)_2R^{32}$, —$S(O)NR^{32}R^{32'}$, —$S(O)_2NR^{32}R^{32'}$, —$OS(O)NR^{32}R^{32'}$, —$OS(O)_2NR^{32}R^{32'}$, —$NR^{32}R^{32'}$, —$NR^{32}C(O)R^{33}$, —$NR^{32}C(O)OR^{33}$, —$NR^{32}C(O)NR^{33}R^{33'}$, —$NR^{32}S(O)R^{33}$, —$NR^{32}S(O)_2R^{33}$, —$NR^{32}S(O)NR^{33}R^{33'}$, —$NR^{32}S(O)_2NR^{33}R^{33'}$, —$C(O)R^{32}$, —$C(O)OR^{32}$ or —$C(O)NR^{32}R^{32'}$;

each $X^6$ is independently $C_1$-$C_6$ alkyl or $C_6$-$C_{10}$ aryl($C_1$-$C_6$ alkyl), wherein each hydrogen atom in $C_1$-$C_6$ alkyl and $C_6$-$C_{10}$ aryl($C_1$-$C_6$ alkyl) is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{34}$, —$OC(O)R^{34}$, —$OC(O)NR^{34}R^{34'}$, —$OS(O)R^{34}$, —$OS(O)_2R^{34}$, —$SR^{34}$, —$S(O)R^{34}$, —$S(O)_2R^{34}$, —$S(O)NR^{34}R^{34'}$, —$S(O)_2NR^{34}R^{34'}$, —$OS(O)NR^{34}R^{34'}$, —$OS(O)_2NR^{34}R^{34'}$, —$NR^{34}R^{34'}$, —$NR^{34}C(O)R^{35}$, —$NR^{34}C(O)OR^{35}$, —$NR^{34}C(O)NR^{35}R^{35'}$, —$NR^{34}S(O)R^{35}$, —$NR^{34}S(O)_2R^{35}$, —$NR^{34}S(O)NR^{35}R^{35'}$, —$NR^{34}S(O)_2NR^{35}R^{35'}$, —$C(O)R^{34}$, —$C(O)OR^{34}$ or —$C(O)NR^{34}R^{34'}$;

each $R^{32}$, $R^{32'}$, $R^{33}$, $R^{33'}$, $R^{34}$, $R^{34'}$, $R^{35}$ and $R^{35'}$ is independently selected from the group consisting of H, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl.

35. The conjugate of clause 33, or a pharmaceutically acceptable salt thereof, wherein L comprises a moiety $L^1$ of the formula

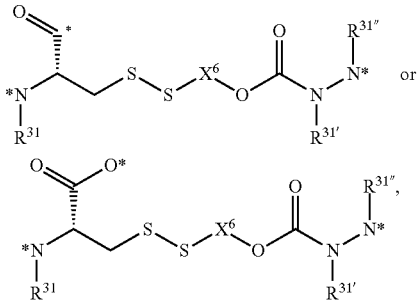

or wherein each $R^{31}$, $R^{31'}$ and $R^{31''}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, $-OR^{32}$, $OC(O)R^{32}$, $-OC(O)NR^{32}R^{32'}$, $-OS(O)R^{32}$, $-OS(O)_2R^{32}$, $-SR^{32}$, $-S(O)R^{32}$, $-S(O)_2R^{32}$, $-S(O)NR^{32}R^{32'}$, $-S(O)_2NR^{32}R^{32'}$, $-OS(O)NR^{32}R^{32'}$, $-OS(O)_2NR^{32}R^{32'}$, $-NR^{32}R^{32'}$, $-NR^{32}C(O)R^{33}$, $-NR^{32}C(O)OR^{33}$, $-NR^{32}C(O)NR^{33}R^{33'}$, $-NR^{32}S(O)R^{33}$, $-NR^{32}S(O)_2R^{33}$, $-NR^{32}S(O)NR^{33}R^{33'}$, $-NR^{32}S(O)_2NR^{33}R^{33'}$, $-C(O)R^{32}$, $-C(O)OR^{32}$ or $-C(O)NR^{32}R^{32'}$;

each $X^6$ is independently $C_1$-$C_6$ alkyl or $C_6$-$C_{10}$ aryl($C_1$-$C_6$ alkyl), wherein each hydrogen atom in $C_1$-$C_6$ alkyl and $C_6$-$C_{10}$ aryl($C_1$-$C_6$ alkyl) is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, $-OR^{34}$, $-OC(O)R^{34}$, $-OC(O)NR^{34}R^{34'}$, $-OS(O)R^{34}$, $-OS(O)_2R^{34}$, $-SR^{34}$, $-S(O)R^{34}$, $-S(O)_2R^{34}$, $-S(O)NR^{34}R^{34'}$, $-S(O)_2NR^{34}R^{34'}$, $-OS(O)NR^{34}R^{34'}$, $-OS(O)_2NR^{34}R^{34'}$, $-NR^{34}R^{34'}$, $-NR^{34}C(O)R^{35}$, $-NR^{34}C(O)OR^{35}$, $-NR^{34}C(O)NR^{35}R^{35'}$, $-NR^{34}S(O)R^{35}$, $-NR^{34}S(O)_2R^{35}$, $-NR^{34}S(O)NR^{35}R^{35'}$, $-NR^{34}S(O)_2NR^{35}R^{35'}$, $-C(O)R^{34}$, $-C(O)OR^{34}$ or $-C(O)NR^{34}R^{34'}$;

each $R^{32}$, $R^{32'}$, $R^{33}$, $R^{33'}$, $R^{34}$, $R^{34'}$, $R^{35}$ and $R^{35'}$ is independently selected from the group consisting of H, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl.

36. The conjugate of clause 33, or a pharmaceutically acceptable salt thereof, wherein L comprises a moiety $L^1$ of the formula

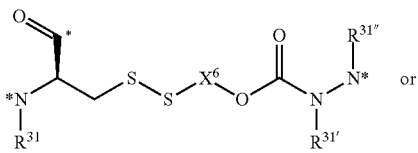

or

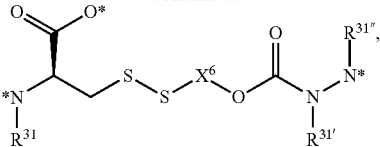

wherein each $R^{31}$, $R^{31'}$ and $R^{31''}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, $-OR^{32}$, $OC(O)R^{32}$, $-OC(O)NR^{32}R^{32'}$, $-OS(O)R^{32}$, $-OS(O)_2R^{32}$, $-SR^{32}$, $-S(O)R^{32}$, $-S(O)_2R^{32}$, $-S(O)NR^{32}R^{32'}$, $-S(O)_2NR^{32}R^{32'}$, $-OS(O)NR^{32}R^{32'}$, $-OS(O)_2NR^{32}R^{32'}$, $-NR^{32}R^{32'}$, $-NR^{32}C(O)R^{33}$, $-NR^{32}C(O)OR^{33}$, $-NR^{32}C(O)NR^{33}R^{33'}$, $-NR^{32}S(O)R^{33}$, $-NR^{32}S(O)_2R^{33}$, $-NR^{32}S(O)NR^{33}R^{33'}$, $-NR^{32}S(O)_2NR^{33}R^{33'}$, $-C(O)R^{32}$, $-C(O)OR^{32}$ or $-C(O)NR^{32}R^{32'}$;

each $X^6$ is independently $C_1$-$C_6$ alkyl or $C_6$-$C_{10}$ aryl($C_1$-$C_6$ alkyl), wherein each hydrogen atom in $C_1$-$C_6$ alkyl and $C_6$-$C_{10}$ aryl($C_1$-$C_6$ alkyl) is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, $-OR^{34}$, $-OC(O)R^{34}$, $-OC(O)NR^{34}R^{34'}$, $-OS(O)R^{34}$, $-OS(O)_2R^{34}$, $-SR^{34}$, $-S(O)R^{34}$, $-S(O)_2R^{34}$, $-S(O)NR^{34}R^{34'}$, $-S(O)_2NR^{34}R^{34'}$, $-OS(O)NR^{34}R^{34'}$, $-OS(O)_2NR^{34}R^{34'}$, $-NR^{34}R^{34'}$, $-NR^{34}C(O)R^{35}$, $-NR^{34}C(O)OR^{35}$, $-NR^{34}C(O)NR^{35}R^{35'}$, $-NR^{34}S(O)R^{35}$, $-NR^{34}S(O)_2R^{35}$, $-NR^{34}S(O)NR^{35}R^{35'}$, $-NR^{34}S(O)_2NR^{35}R^{35'}$, $-C(O)R^{34}$, $-C(O)OR^{34}$ or $-C(O)NR^{34}R^{34'}$;

each $R^{32}$, $R^{32'}$, $R^{33}$, $R^{33'}$, $R^{34}$, $R^{34'}$, $R^{35}$ and $R^{35'}$ is independently selected from the group consisting of H, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl.

37. The conjugate of any one of clauses 1 to 32, or a pharmaceutically acceptable salt thereof, wherein L comprises a moiety $L^1$ of the formula selected from the group consisting of

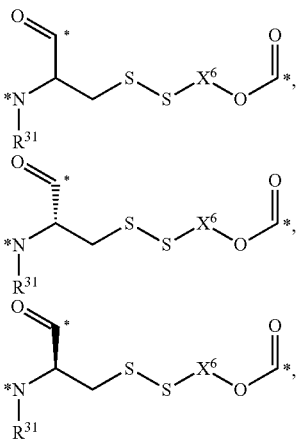

-continued

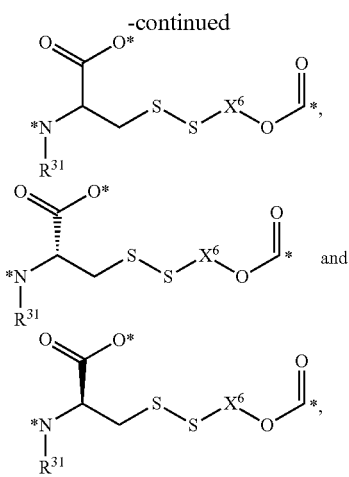

wherein each $R^{31}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{32}$, $OC(O)R^{32}$, —$OC(O)NR^{32}R^{32'}$, —$OS(O)R^{32}$, —$OS(O)_2R^{32}$, —$SR^{32}$, —$S(O)R^{32}$, —$S(O)_2R^{32}$, —$S(O)NR^{32}R^{32'}$, —$S(O)_2NR^{32}R^{32'}$, —$OS(O)NR^{32}R^{32'}$, —$OS(O)_2NR^{32}R^{32'}$, —$NR^{32}R^{32'}$, —$NR^{32}C(O)R^{33}$, —$NR^{32}C(O)OR^{33}$, —$NR^{32}C(O)NR^{33}R^{33'}$, —$NR^{32}S(O)R^{33}$, —$NR^{32}S(O)_2R^{33}$, —$NR^{32}S(O)NR^{33}R^{33'}$, —$NR^{32}S(O)_2NR^{33}R^{33'}$, —$C(O)R^{32}$, —$C(O)OR^{32}$ or —$C(O)NR^{32}R^{32'}$;

each $X^6$ is independently $C_1$-$C_6$ alkyl or $C_6$-$C_{10}$ aryl($C_1$-$C_6$ alkyl), wherein each hydrogen atom in $C_1$-$C_6$ alkyl and $C_6$-$C_{10}$ aryl($C_1$-$C_6$ alkyl) is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{34}$, —$OC(O)R^{34}$, —$OC(O)NR^{34}R^{34'}$, —$OS(O)R^{34}$, —$OS(O)_2R^{34}$, —$SR^{34}$, —$S(O)R^{34}$, —$S(O)_2R^{34}$, —$S(O)NR^{34}R^{34'}$, —$S(O)_2NR^{34}R^{34'}$, —$OS(O)NR^{34}R^{34'}$, —$OS(O)_2NR^{34}R^{34'}$, —$NR^{34}R^{34'}$, —$NR^{34}C(O)R^{35}$, —$NR^{34}C(O)OR^{35}$, —$NR^{34}C(O)NR^{35}R^{35'}$, —$NR^{34}S(O)R^{35}$, —$NR^{34}S(O)_2R^{35}$, —$NR^{34}S(O)NR^{35}R^{35'}$, —$NR^{34}S(O)_2NR^{35}R^{35'}$, —$C(O)R^{34}$, —$C(O)OR^{34}$ or —$C(O)NR^{34}R^{34'}$;

each $R^{32}$, $R^{32'}$, $R^{33}$, $R^{33'}$, $R^{34}$, $R^{34'}$, $R^{35}$ and $R^{35'}$ is independently selected from the group consisting of H, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl.

38. The conjugate of clause 37, or a pharmaceutically acceptable salt thereof, wherein L comprises a moiety $L^1$ of the formula

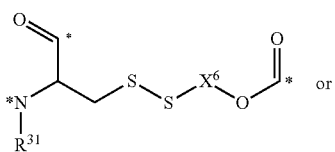

-continued

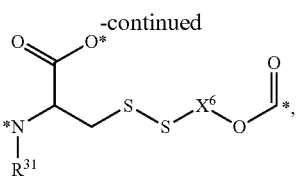

wherein each $R^{31}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{32}$, $OC(O)R^{32}$, —$OC(O)NR^{32}R^{32'}$, —$OS(O)R^{32}$, —$OS(O)_2R^{32}$, —$SR^{32}$, —$S(O)R^{32}$, —$S(O)_2R^{32}$, —$S(O)NR^{32}R^{32'}$, —$S(O)_2NR^{32}R^{32'}$, —$OS(O)NR^{32}R^{32'}$, —$OS(O)_2NR^{32}R^{32'}$, —$NR^{32}R^{32'}$, —$NR^{32}C(O)R^{33}$, —$NR^{32}C(O)OR^{33}$, —$NR^{32}C(O)NR^{33}R^{33'}$, —$NR^{32}S(O)R^{33}$, —$NR^{32}S(O)_2R^{33}$, —$NR^{32}S(O)NR^{33}R^{33'}$, —$NR^{32}S(O)_2NR^{33}R^{33'}$, —$C(O)R^{32}$, —$C(O)OR^{32}$ or —$C(O)NR^{32}R^{32'}$;

each $X^6$ is independently $C_1$-$C_6$ alkyl or $C_6$-$C_{10}$ aryl($C_1$-$C_6$ alkyl), wherein each hydrogen atom in $C_1$-$C_6$ alkyl and $C_6$-$C_{10}$ aryl($C_1$-$C_6$ alkyl) is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{34}$, —$OC(O)R^{34}$, —$OC(O)NR^{34}R^{34'}$, —$OS(O)R^{34}$, —$OS(O)_2R^{34}$, —$SR^{34}$, —$S(O)R^{34}$, —$S(O)_2R^{34}$, —$S(O)NR^{34}R^{34'}$, —$S(O)_2NR^{34}R^{34'}$, —$OS(O)NR^{34}R^{34'}$, —$OS(O)_2NR^{34}R^{34'}$, —$NR^{34}R^{34'}$, —$NR^{34}C(O)R^{35}$, —$NR^{34}C(O)OR^{35}$, —$NR^{34}C(O)NR^{35}R^{35'}$, —$NR^{34}S(O)R^{35}$, —$NR^{34}S(O)_2R^{35}$, —$NR^{34}S(O)NR^{35}R^{35'}$, —$NR^{34}S(O)_2NR^{35}R^{35'}$, —$C(O)R^{34}$, —$C(O)OR^{34}$ or —$C(O)NR^{34}R^{34'}$;

each $R^{32}$, $R^{32'}$, $R^{33}$, $R^{33'}$, $R^{34}$, $R^{34'}$, $R^{35}$ and $R^{35'}$ is independently selected from the group consisting of H, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl.

39. The conjugate of clause 37, or a pharmaceutically acceptable salt thereof, wherein L comprises a moiety $L^1$ of the formula

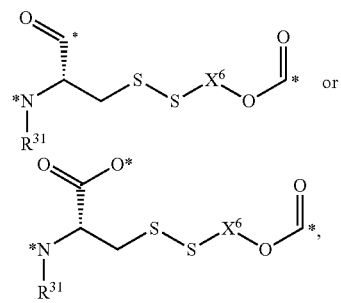

wherein each $R^{31}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{32}$, $OC(O)R^{32}$, —$OC(O)NR^{32}R^{32'}$, —$OS(O)R^{32}$, —$OS(O)_2R^{32}$, —$SR^{32}$, —$S(O)R^{32}$, —$S(O)_2R^{32}$, —$S(O)NR^{32}R^{32'}$, —$S(O)_2NR^{32}R^{32'}$, —$OS(O)NR^{32}R^{32'}$, —$OS(O)_2NR^{32}R^{32'}$, —$NR^{32}R^{32'}$, —$NR^{32}C(O)R^{33}$, —$NR^{32}C(O)OR^{33}$, —$NR^{32}C(O)NR^{33}R^{33'}$, —$NR^{32}S(O)R^{33}$, —$NR^{32}S(O)_2R^{33}$, —$NR^{32}S(O)NR^{33}R^{33'}$, —$NR^{32}S(O)_2NR^{33}R^{33'}$, —$C(O)R^{32}$, —$C(O)OR^{32}$ or —$C(O)NR^{32}R^{32'}$;

each $X^6$ is independently $C_1$-$C_6$ alkyl or $C_6$-$C_{10}$ aryl($C_1$-$C_6$ alkyl), wherein each hydrogen atom in $C_1$-$C_6$ alkyl and $C_6$-$C_{10}$ aryl($C_1$-$C_6$ alkyl) is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{34}$, —$OC(O)R^{34}$, —$OC(O)NR^{34}R^{34'}$, —$OS(O)R^{34}$, —$OS(O)_2R^{34}$, —$SR^{34}$, —$S(O)R^{34}$, —$S(O)_2R^{34}$, —$S(O)NR^{34}R^{34'}$, —$S(O)_2NR^{34}R^{34'}$, —$OS(O)NR^{34}R^{34'}$, —$OS(O)_2NR^{34}R^{34'}$, —$NR^{34}R^{34'}$, —$C(O)R^{35}$, —$NR^{34}C(O)OR^{35}$, —$NR^{34}C(O)NR^{35}R^{35'}$, —$NR^{34}S(O)R^{35}$, —$NR^{34}S(O)_2R^{35}$, —$NR^{34}S(O)NR^{35}R^{35'}$, —$NR^{34}S(O)_2NR^{35}R^{35'}$, —$C(O)R^{34}$, —$C(O)OR^{34}$ or —$C(O)NR^{34}R^{34'}$;

each $R^{32}$, $R^{32'}$, $R^{33}$, $R^{33'}$, $R^{34}$, $R^{34'}$, $R^{35}$ and $R^{35'}$ is independently selected from the group consisting of H, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl.

40. The conjugate of clause 37, or a pharmaceutically acceptable salt thereof, wherein L comprises a moiety $L^1$ of the formula

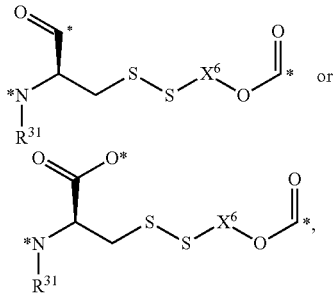

wherein each $R^{31}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{32}$, $OC(O)R^{32}$, —$OC(O)NR^{32}R^{32'}$, —$OS(O)R^{32}$, —$OS(O)_2R^{32}$, —$SR^{32}$, —$S(O)R^{32}$, —$S(O)_2R^{32}$, —$S(O)NR^{32}R^{32'}$, —$S(O)_2NR^{32}R^{32'}$, —$OS(O)NR^{32}R^{32'}$, —$OS(O)_2NR^{32}R^{32'}$, —$NR^{32}R^{32'}$, —$NR^{32}C(O)R^{33}$, —$NR^{32}C(O)OR^{33}$, —$NR^{32}C(O)NR^{33}R^{33'}$, —$NR^{32}S(O)R^{33}$, —$NR^{32}S(O)_2R^{33}$, —$NR^{32}S(O)NR^{33}R^{33'}$, —$NR^{32}S(O)_2NR^{33}R^{33'}$, —$C(O)R^{32}$, —$C(O)OR^{32}$ or —$C(O)NR^{32}R^{32'}$;

each $X^6$ is independently $C_1$-$C_6$ alkyl or $C_6$-$C_{10}$ aryl($C_1$-$C_6$ alkyl), wherein each hydrogen atom in $C_1$-$C_6$ alkyl and $C_6$-$C_{10}$ aryl($C_1$-$C_6$ alkyl) is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{34}$, —$OC(O)R^{34}$, —$OC(O)NR^{34}R^{34'}$, —$OS(O)R^{34}$, —$OS(O)_2R^{34}$, —$SR^{34}$, —$S(O)R^{34}$, —$S(O)_2R^{34}$, —$S(O)NR^{34}R^{34'}$, —$S(O)_2NR^{34}R^{34'}$, —$OS(O)NR^{34}R^{34'}$, —$OS(O)_2NR^{34}R^{34'}$, —$NR^{34}R^{34'}$, —$NR^{34}C(O)R^{35}$, —$NR^{34}C(O)OR^{35}$, —$NR^{34}C(O)NR^{35}R^{35'}$, —$NR^{34}S(O)R^{35}$, —$NR^{34}S(O)_2R^{35}$, —$NR^{34}S(O)NR^{35}R^{35'}$, —$NR^{34}S(O)_2NR^{35}R^{35'}$, —$C(O)R^{34}$ or —$C(O)NR^{34}R^{34'}$;

each $R^{32}$, $R^{32'}$, $R^{33}$, $R^{33'}$, $R^{34}$, $R^{34'}$, $R^{35}$ and $R^{35'}$ is independently selected from the group consisting of H, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl.

41. The conjugate of any one of clauses 32 to 40, or a pharmaceutically acceptable salt thereof, wherein $X^6$ is $C_1$-$C_6$ alkyl.

42. The conjugate of any one of clauses 32 to 41, or a pharmaceutically acceptable salt thereof, wherein $R^{31}$ is H.

43. The conjugate of any one of clauses 32 to 42, or a pharmaceutically acceptable salt thereof, wherein $R^{31'}$ is H.

44. The conjugate of any one of clauses 32 to 43, or a pharmaceutically acceptable salt thereof, wherein $R^{31''}$ is H.

45. The conjugate of any one of the preceding clauses, wherein L comprises a moiety $L^2$ of the formula

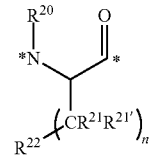

wherein $R^{20}$ is selected from the group consisting of H, $C_1$-$C_6$ alkyl, $C_2$-$C_6$ alkenyl, $C_2$-$C_6$ alkynyl, —$C(O)R^{23}$, —$C(O)OR^{23}$ and —$C(O)NR^{23}R^{23'}$, wherein each hydrogen atom in $C_1$-$C_6$ alkyl, $C_2$-$C_6$ alkenyl and $C_2$-$C_6$ alkynyl is independently optionally substituted by halogen, $C_1$-$C_6$ alkyl, $C_2$-$C_6$ alkenyl, and $C_2$-$C_6$ alkynyl, —$OR^{24}$, —$OC(O)R^{24}$, —$OC(O)NR^{24}R^{24'}$, —$OS(O)R^{24}$, —$OS(O)_2R^{24}$, —$SR^{24}$, —$S(O)R^{24}$, —$S(O)_2R^{24}$, —$S(O)NR^{24}R^{24'}$, —$S(O)_2NR^{24}R^{24'}$, —$OS(O)NR^{24}R^{24'}$, —$OS(O)_2NR^{24}R^{24'}$, —$NR^{24}R^{24'}$, —$NR^{24}C(O)R^{25}$, —$NR^{24}C(O)OR^{25}$, —$NR^{24}C(O)NR^{25}R^{25'}$, —$NR^{24}S(O)R^{25}$, —$NR^{24}S(O)_2R^{25}$, —$NR^{24}S(O)NR^{25}R^{25'}$, —$NR^{24}S(O)_2NR^{25}R^{25'}$, $C(O)R^{24}$, —$C(O)OR^{24}$, or —$C(O)NR^{24}R^{24'}$;

each $R^{21}$ and $R^{21'}$ is independently selected from the group consisting of H, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{24}$, $OC(O)R^{24}$, —$OC(O)NR^{24}R^{24'}$, —$OS(O)R^{24}$, —$OS(O)_2R^{24}$, —$SR^{24}$, —$S(O)R^{24}$, —$S(O)_2R^{24}$, —$S(O)NR^{24}R^{24'}$, —$S(O)_2NR^{24}R^{24'}$, —$OS(O)NR^{24}R^{24'}$, —$OS(O)_2NR^{24}R^{24'}$, —$NR^{24}R^{24'}$, —$NR^{24}C(O)R^{25}$, —$NR^{24}C(O)OR^{25}$, —$NR^{24}C(O)NR^{25}R^{25'}$, —$NR^{24}S(O)R^{25}$, —$NR^{24}S(O)_2R^{25}$, —$NR^{24}S(O)NR^{25}R^{25'}$, —$NR^{24}S(O)_2NR^{25}R^{25'}$, —$C(O)R^{24}$, —$C(O)OR^{24}$ and —$C(O)NR^{24}R^{24'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by halogen, $C_1$-$C_6$ alkyl, $C_2$-$C_6$ alkenyl, $C_2$-$C_6$ alkynyl, —$OR^{24}$, —$OC(O)R^{24}$, —$OC(O)NR^{24}R^{24'}$, —$OS(O)R^{24}$, —$OS(O)_2R^{24}$, —$SR^{24}$, —$S(O)R^{24}$, —$S(O)_2R^{24}$, —$S(O)NR^{24}R^{24'}$, —$S(O)_2NR^{24}R^{24'}$, —$OS(O)NR^{24}R^{24'}$, —$OS(O)_2NR^{24}R^{24'}$, —$NR^{24}R^{24'}$, —$NR^{24}C(O)R^{25}$, —NR$^{24}$C(O)OR$^{25}$, NR$^{24}$C(O)NR$^{25}$R$^{25'}$, —NR$^{24}$S(O)R$^{25}$, —NR$^{24}$S(O)$_2$R$^{25}$, —NR$^{24}$S(O)NR$^{25}$R$^{25'}$, —NR$^{24}$S(O)$_2$NR$^{25}$R$^{25'}$, —C(O)R$^{24}$, —C(O)OR$^{24}$ or —C(O)NR$^{24}$R$^{24'}$; or R$^{21}$ and R$^{21'}$ may combine to form a C$_4$-C$_6$ cycloalkyl or a 4- to 6-membered heterocycle, wherein each hydrogen atom in C$_4$-C$_6$ cycloalkyl or 4- to 6-membered heterocycle is independently optionally substituted by halogen, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{24}$, —OC(O)R$^{24}$, —OC(O)NR$^{24}$R$^{24'}$, —OS(O)R$^{24}$, —OS(O)$_2$R$^{24}$, —SR$^{24}$, —S(O)R$^{24}$, —S(O)$_2$R$^{24}$, —S(O)NR$^{24}$R$^{24'}$, —S(O)$_2$NR$^{24}$R$^{24'}$, —OS(O)NR$^{24}$R$^{24'}$, —OS(O)$_2$NR$^{24}$R$^{24'}$, —NR$^{24}$R$^{24'}$, —NR$^{24}$C(O)R$^{25}$, —NR$^{24}$C(O)OR$^{25}$, —NR$^{24}$C(O)NR$^{25}$R$^{25'}$, —NR$^{24}$S(O)R$^{25}$, —NR$^{24}$S(O)$_2$R$^{25}$, —NR$^{24}$S(O)NR$^{25}$R$^{25'}$, —NR$^{24}$S(O)$_2$NR$^{25}$R$^{25'}$, —C(O)R$^{24}$, —C(O)OR$^{24}$ or —C(O)NR$^{24}$R$^{24'}$;

R$^{22}$ is selected from the group consisting of H, D, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{26}$, —OC(O)R$^{26}$, —OC(O)NR$^{26}$R$^{26'}$, —OS(O)R$^{26}$, —OS(O)$_2$R$^{26}$, —SR$^{26}$, —S(O)R$^{26}$, —S(O)$_2$R$^{26}$, —S(O)NR$^{26}$R$^{26'}$, —S(O)$_2$NR$^{26}$R$^{26'}$, —OS(O)NR$^{26}$R$^{26'}$, —OS(O)$_2$NR$^{26}$R$^{26'}$, —NR$^{26}$R$^{26'}$, —NR$^{26}$C(O)R$^{27}$, —NR$^{26}$C(O)OR$^{27}$, —NR$^{26}$C(O)NR$^{27}$R$^{27'}$, NR$^{26}$C(=NR$^{26''}$)NR$^{27}$R$^{27'}$, —NR$^{26}$S(O)R$^{27}$, —NR$^{26}$S(O)$_2$R$^{27}$, —NR$^{26}$S(O)NR$^{27}$R$^{27'}$, —NR$^{26}$S(O)$_2$NR$^{27}$R$^{27'}$, —C(O)R$^{26}$, —C(O)OR$^{26}$ and —C(O)NR$^{26}$R$^{26'}$, wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl and 5- to 7-membered heteroaryl is independently optionally substituted by halogen, C$_1$-C$_6$ alkyl, C$_2$-C$_6$ alkenyl, —(CH$_2$)$_p$OR$^{28}$, —(CH$_2$)$_p$(OCH$_2$)$_q$OR$^{28}$, —(CH$_2$)$_p$(OCH$_2$CH$_2$)$_q$OR$^{28}$, —OR$^{29}$, —OC(O)R$^{29}$, —OC(O)NR$^{29}$R$^{29'}$, —OS(O)R$^{29}$, —OS(O)$_2$R$^{29}$, —(CH$_2$)$_p$OS(O)OR$^{29}$, —OS(O)$_2$OR$^{29}$, —SR$^{29}$, —S(O)R$^{29}$, —S(O)$_2$R$^{29}$, —S(O)NR$^{29}$R$^{29'}$, —S(O)$_2$NR$^{29}$R$^{29'}$, —OS(O)NR$^{29}$R$^{29'}$, —OS(O)$_2$NR$^{29}$R$^{29'}$, —NR$^{29}$R$^{29'}$, —NR$^{29}$C(O)R$^{30}$, —NR$^{29}$C(O)OR$^{30}$, —NR$^{29}$C(O)NR$^{30}$R$^{30'}$, —NR$^{29}$S(O)R$^{30}$, —NR$^{29}$S(O)$_2$R$^{30}$, —NR$^{29}$S(O)NR$^{30}$R$^{30'}$, —NR$^{29}$S(O)$_2$NR$^{30}$R$^{30'}$, —C(O)R$^{29}$, —C(O)OR$^{29}$ or —C(O)NR$^{29}$R$^{29'}$;

each R$^{24}$, R$^{24'}$, R$^{25}$, R$^{25'}$, R$^{26}$, R$^{26'}$, R$^{26''}$, R$^{29}$, R$^{29'}$, R$^{30}$ and R$^{30'}$ is independently selected from the group consisting of H, D, C$_1$-C$_7$ alkyl, C$_2$-C$_7$ alkenyl, C$_2$-C$_7$ alkynyl, C$_3$-C$_6$ cycloalkyl, 3- to 7-membered heterocycloalkyl, C$_6$-C$_{10}$ aryl and 5- to 7-membered heteroaryl, wherein each hydrogen atom in C$_1$-C$_7$ alkyl, C$_2$-C$_7$ alkenyl, C$_2$-C$_7$ alkynyl, C$_3$-C$_6$ cycloalkyl, 3- to 7-membered heterocycloalkyl, C$_6$-C$_{10}$ aryl, or 5- to 7-membered heteroaryl is independently optionally substituted by halogen, —OH, —SH, —NH$_2$ or —CO$_2$H;

R$^{27}$ and R$^{27'}$ are each independently selected from the group consisting of H, C$_1$-C$_9$ alkyl, C$_2$-C$_9$ alkenyl, C$_2$-C$_9$ alkynyl, C$_3$-C$_6$ cycloalkyl, —(CH$_2$)$_p$(sugar), —(CH$_2$)$_p$(OCH$_2$CH$_2$)$_q$-(sugar) and —(CH$_2$)$_p$(OCH$_2$CH$_2$CH$_2$)$_q$(sugar);

R$^{28}$ is H, D, C$_1$-C$_7$ alkyl, C$_2$-C$_7$ alkenyl, C$_2$-C$_7$ alkynyl, C$_3$-C$_6$ cycloalkyl, 3- to 7-membered heterocycloalkyl, C$_6$-C$_{10}$ aryl, 5- to 7-membered heteroaryl or sugar;

n is 1, 2, 3, 4 or 5;

p is 1, 2, 3, 4 or 5;

q is 1, 2, 3, 4 or 5; and

* is a covalent bond.

46. The conjugate of any of the preceding clauses, wherein L comprises a moiety L$^2$ of the formula

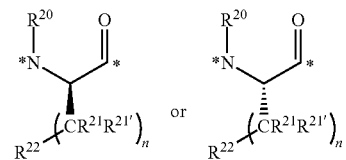

wherein R$^{20}$, R$^{21}$, R$^{21'}$, R$^{22}$ and n are as described herein, or a pharmaceutically acceptable salt thereof.

47. The conjugate of any of the preceding clauses, wherein L comprises a moiety L$^2$ of the formula

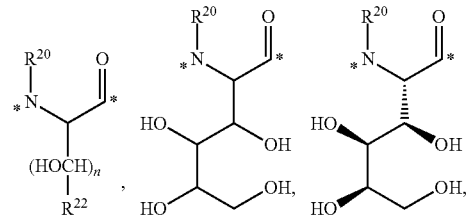

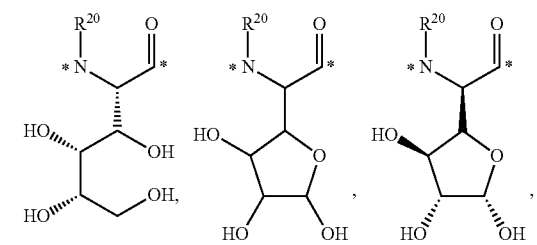

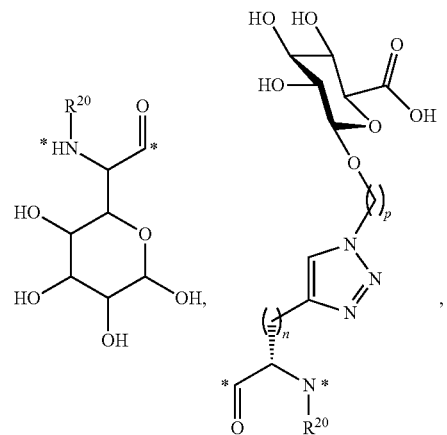

23
-continued
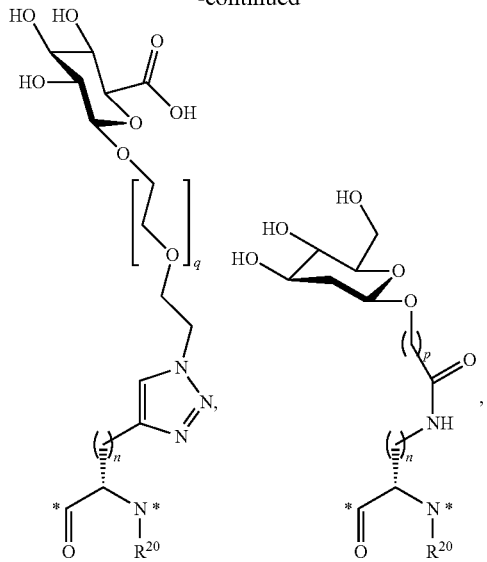
24
-continued
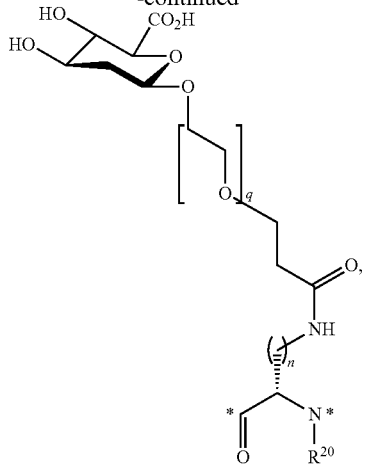
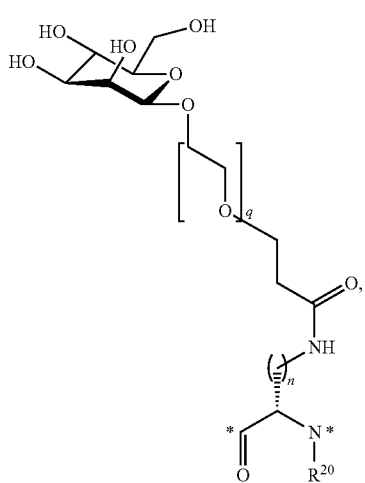
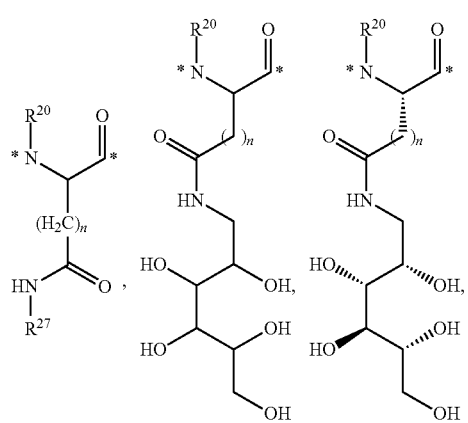

-continued

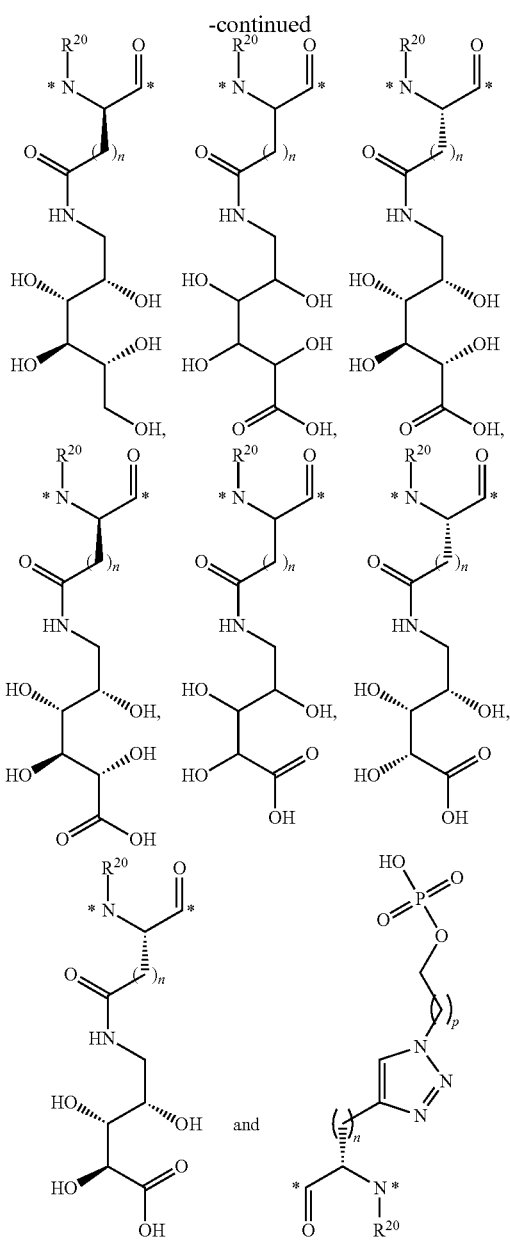

wherein $R^{20}$, n, p, q and r are as described herein, or a pharmaceutically acceptable salt thereof.

48. The conjugate of any one of the preceding clauses, or a pharmaceutically acceptable salt thereof, wherein L comprises one or more moiety $L^3$ of the formula

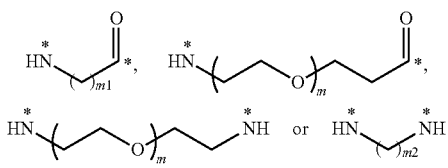

wherein m is an integer from 1 to about 50, m1 is an integer from 1 to about 30, m2 is an integer from 1 to 20, and each * represents a covalent bond to the rest of the conjugate.

49. The conjugate of any one of the preceding clauses, or a pharmaceutically acceptable salt thereof, wherein L comprises at least one AA.

50. The conjugate of any one of the preceding clauses, or a pharmaceutically acceptable salt thereof, wherein L is of the formula

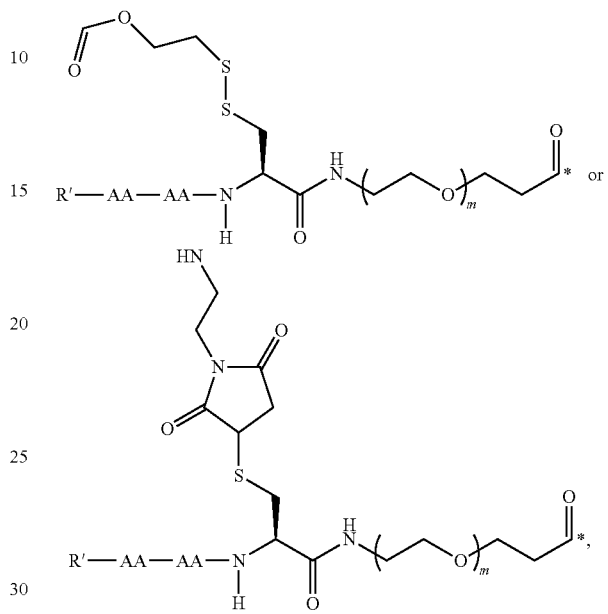

wherein AA is an amino acid, R' is selected from the group consisting of H, $C_1$-$C_6$ alkyl, and —C(O)R", R" is selected from the group consisting of H, $C_1$-$C_6$ alkyl, $C_2$-$C_6$ alkenyl, $C_2$-$C_6$ alkynyl $C_3$-$C_6$ cycloalkyl and $C_6$-$C_{10}$ aryl, m is an integer between 1 and 50, and * is a covalent bond.

51. The conjugate of any one of clauses 1 to 49, or a pharmaceutically acceptable salt thereof, wherein L is of the formula

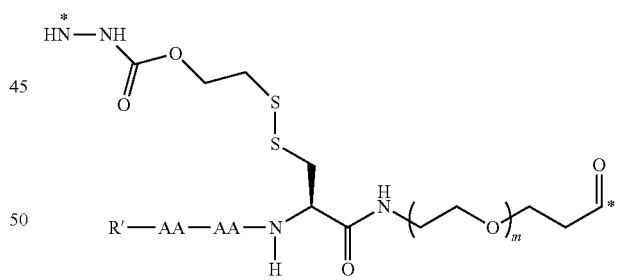

wherein AA is an amino acid, R' is selected from the group consisting of H, $C_1$-$C_6$ alkyl, and —C(O)R", R" is selected from the group consisting of H, $C_1$-$C_6$ alkyl, $C_2$-$C_6$ alkenyl, $C_2$-$C_6$ alkynyl $C_3$-$C_6$ cycloalkyl and $C_6$-$C_{10}$ aryl, m is an integer between 1 and 50, and * is a covalent bond.

52. The conjugate of clause 50 or 51, or a pharmaceutically acceptable salt thereof, wherein m is 2.

53. The conjugate of clause 50 or 51, or a pharmaceutically acceptable salt thereof, wherein m is 3.

54. The conjugate of clause 50 or 51, or a pharmaceutically acceptable salt thereof, wherein m is 12.

55. The conjugate of any one of clauses 1 to 49, or a pharmaceutically acceptable salt thereof, wherein L is of the formula -$L^3$-AA-$L^2$-AA-$L^2$-$L^1$-.

56. The conjugate of any one of clauses 1 to 49, or a pharmaceutically acceptable salt thereof, wherein L is of the formula

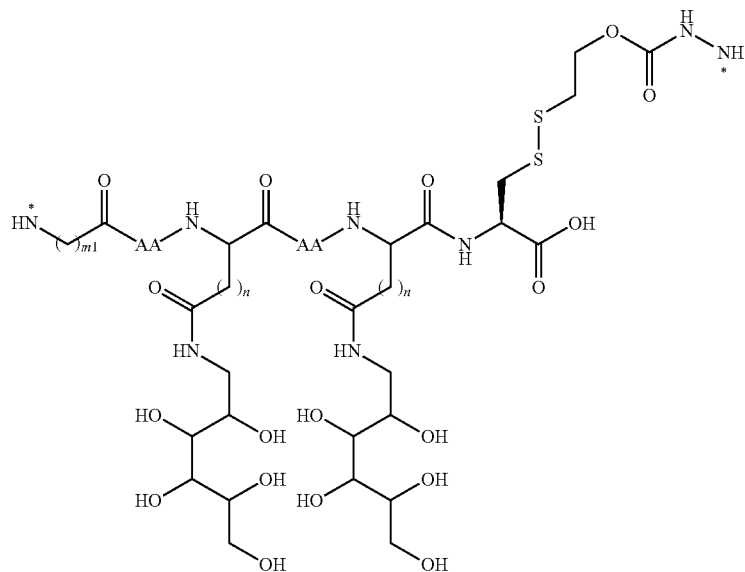

wherein m1 is an integer from 1 to about 30, and n is 2.

57. The conjugate of any one of clauses 1 to 49, or a pharmaceutically acceptable salt thereof, wherein L is of the formula -$L^3$-AA-$L^2$-AA-$L^2$-AA-AA-$L^1$-.

58. The conjugate of any one of clauses 1 to 49, or a pharmaceutically acceptable salt thereof, wherein L is of the formula

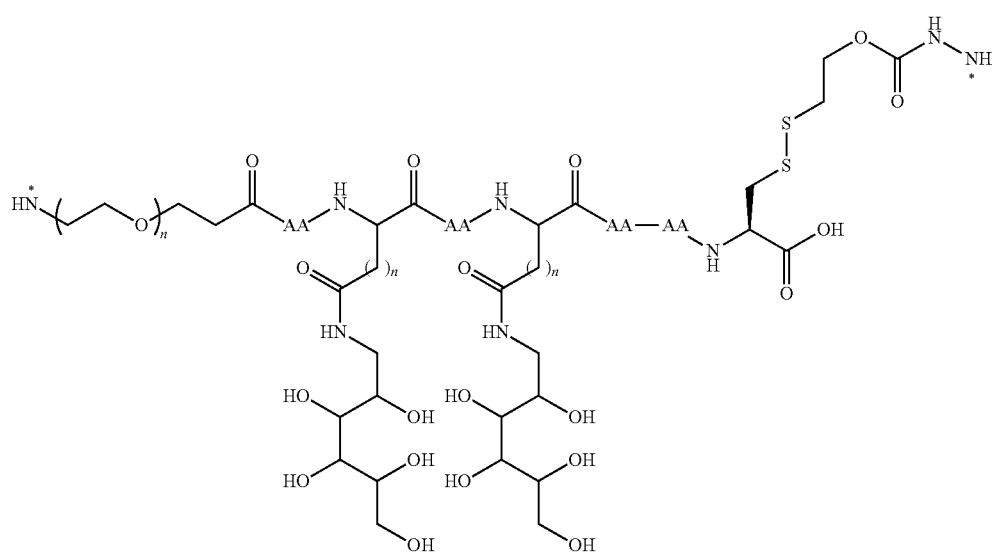

wherein m is an integer from about 1 to about 50, and n is 2.

59. The conjugate of any one of the preceding clauses, wherein AA is selected from the group consisting of Glu, Asp and Dap.
60. The conjugate of clause 1, or a pharmaceutically acceptable salt thereof, of the formula
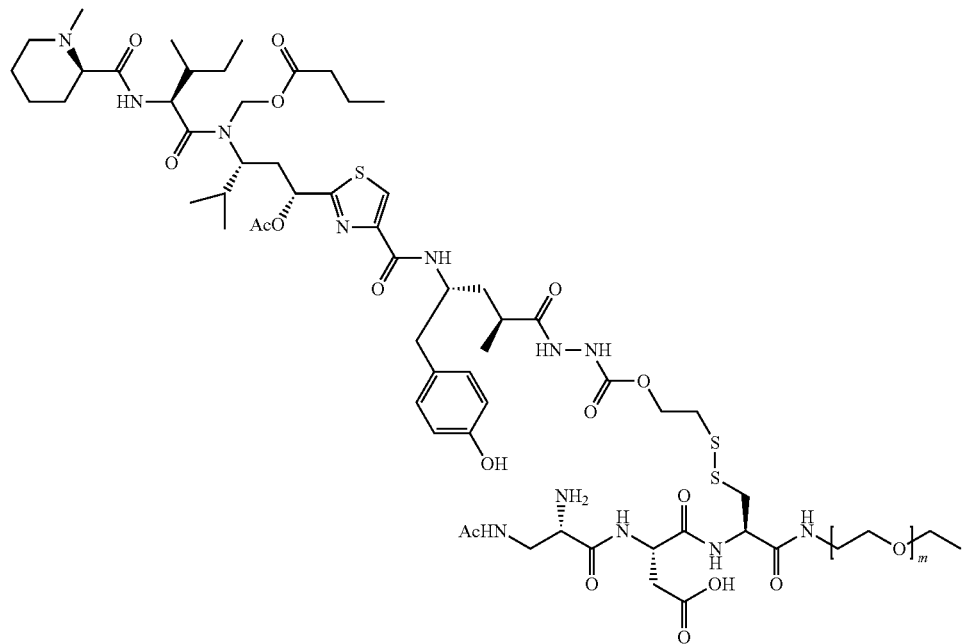
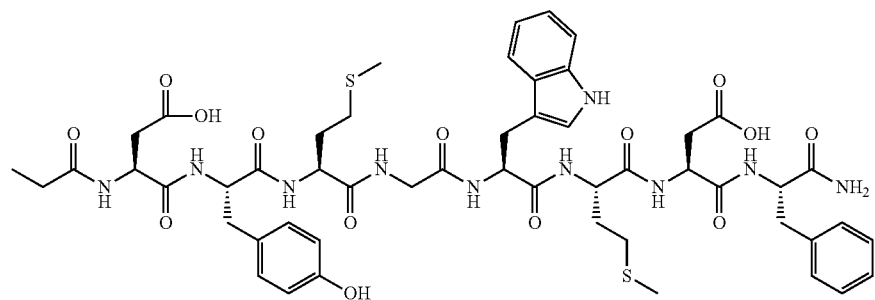
wherein m is 2.
61. The conjugate of clause 1, or a pharmaceutically acceptable salt thereof, of the formula

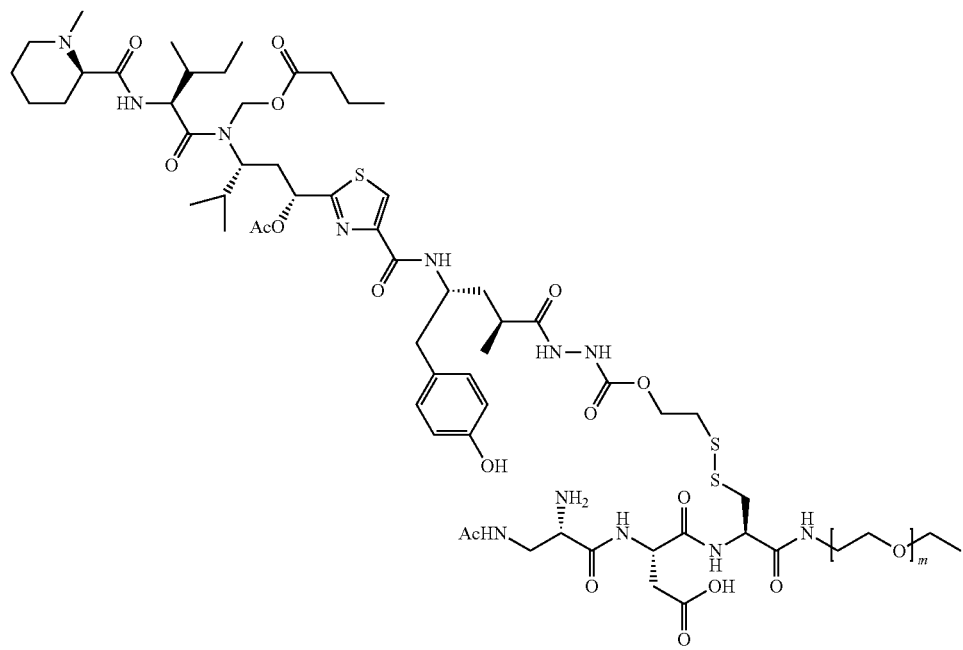
wherein m1 is 3.
62. The conjugate of clause 1, or a pharmaceutically acceptable salt thereof, of the formula
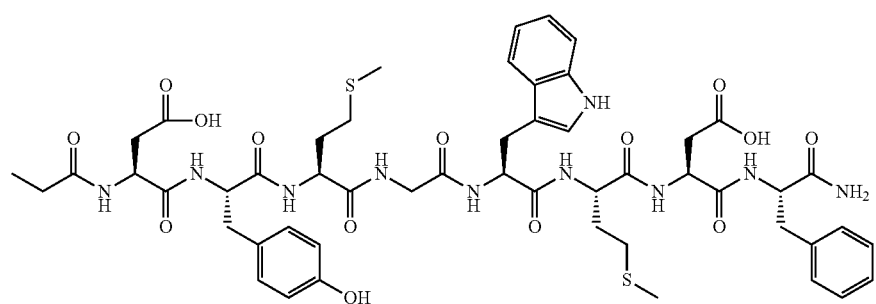

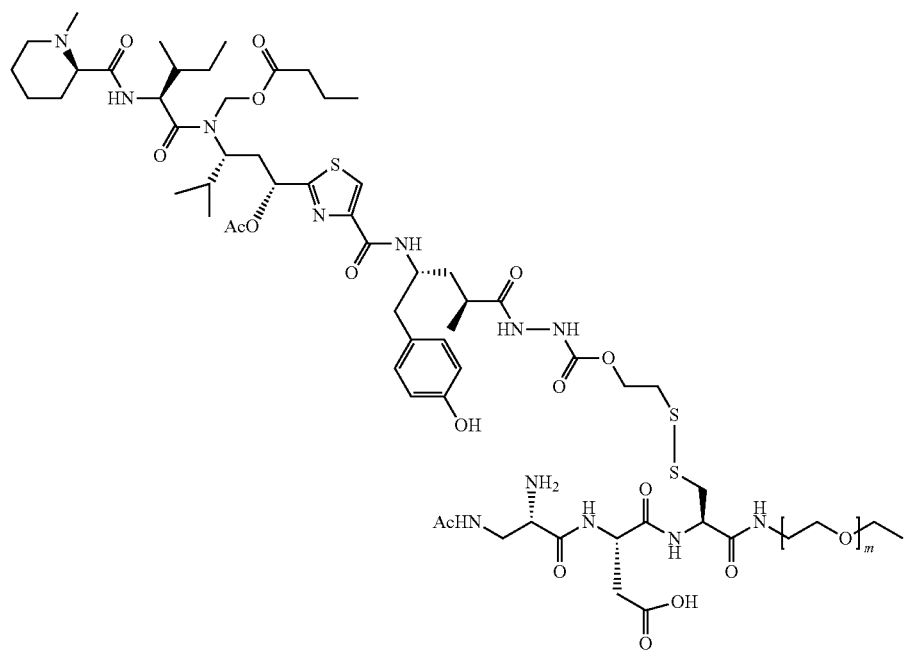
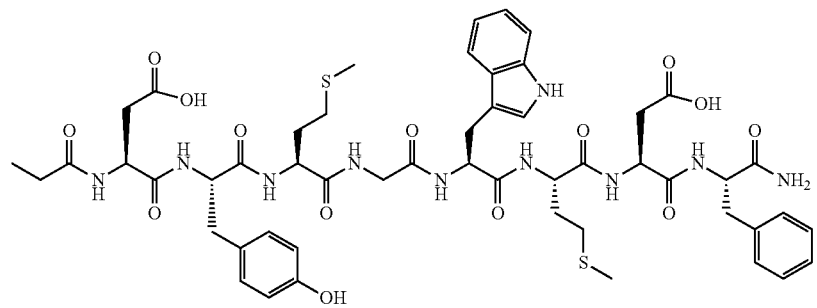
wherein m is 12.
63. The conjugate of clause 1, or a pharmaceutically acceptable salt thereof, of the formula

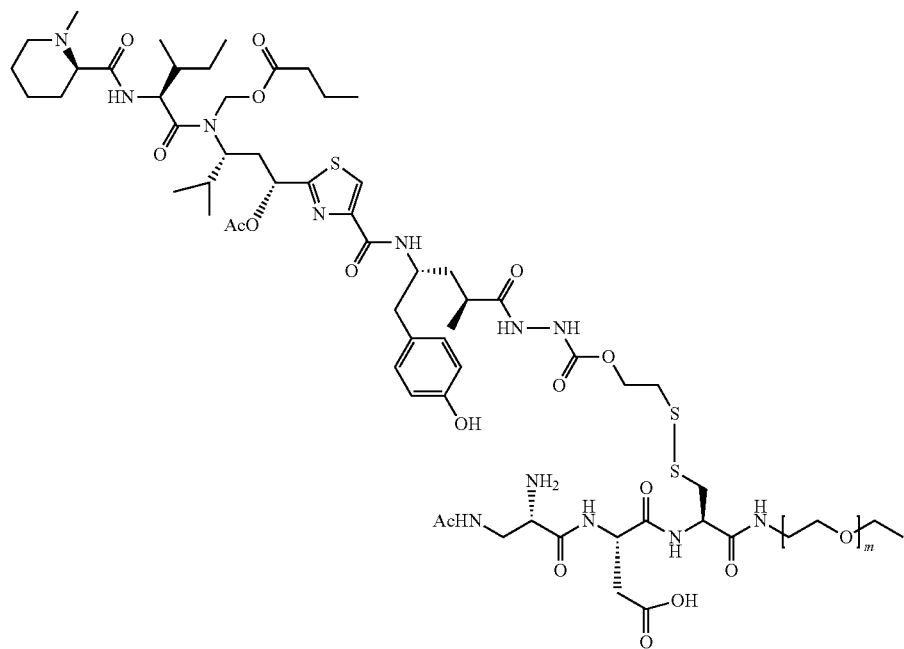
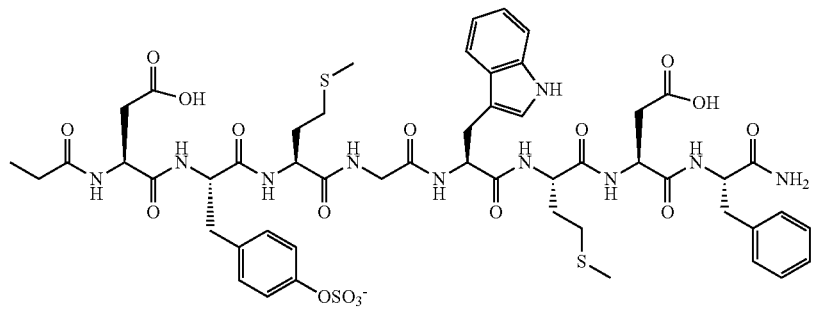
wherein m is 2.
64. The conjugate of clause 1, having the formula
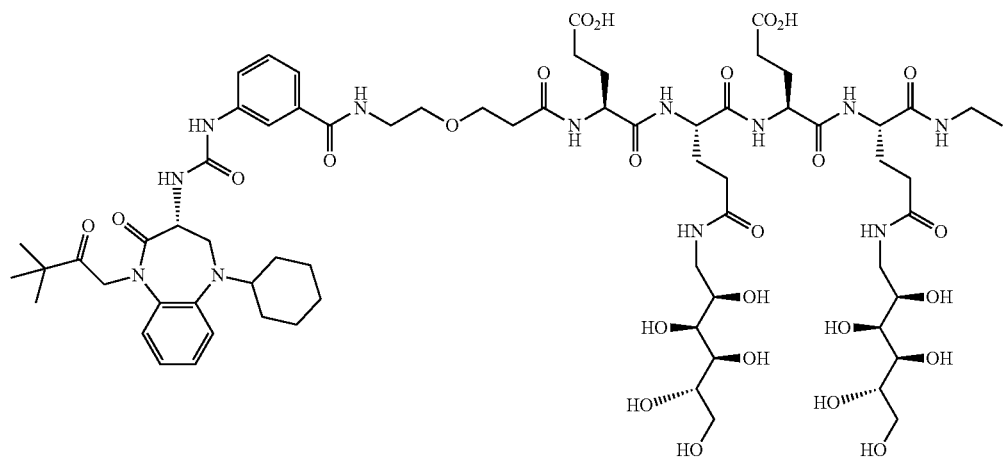

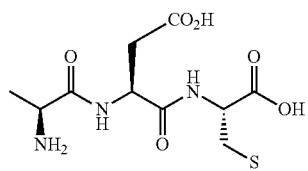
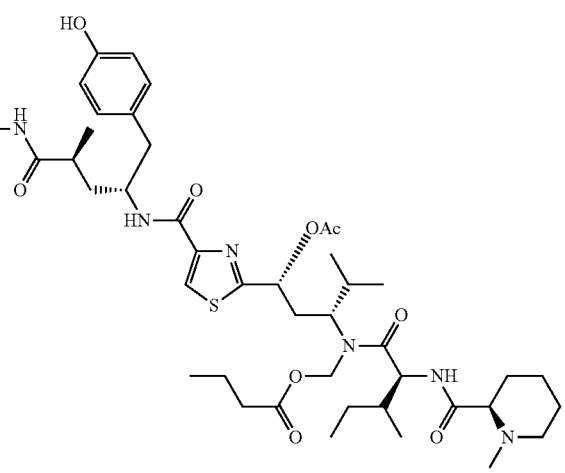
or a pharmaceutically acceptable salt thereof.
65. The conjugate of clause 1, having the formula
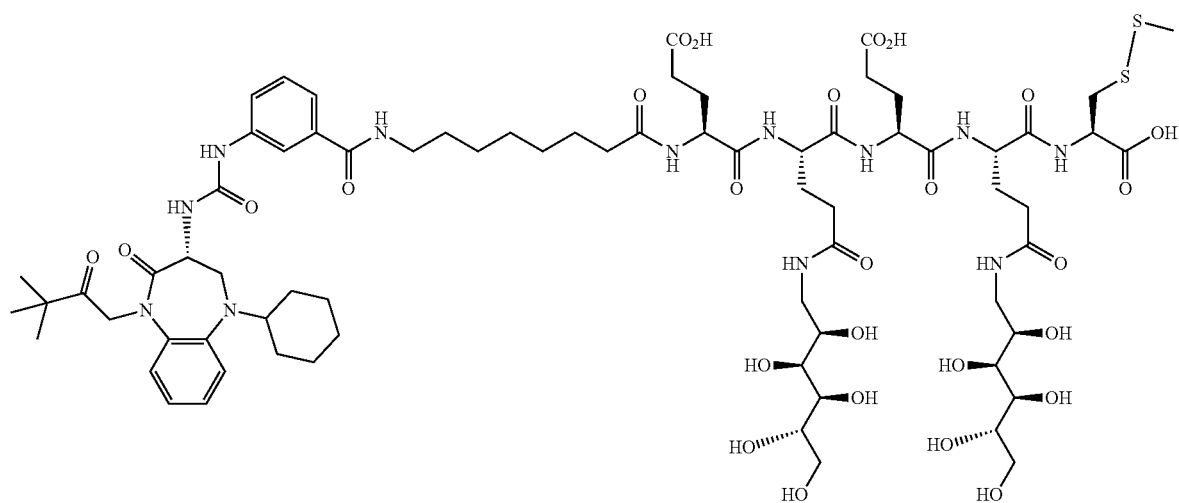
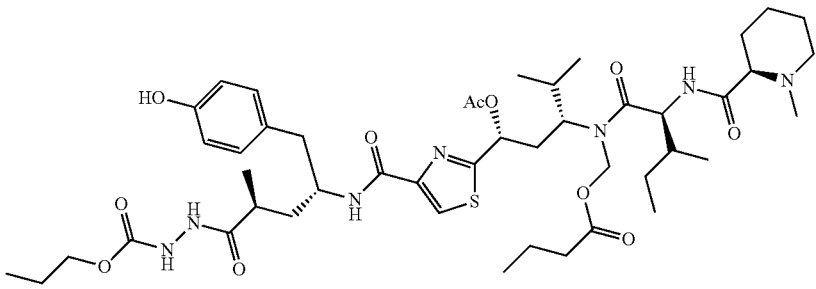
or a pharmaceutically acceptable salt thereof.

66. The conjugate of clause 1, having the formula

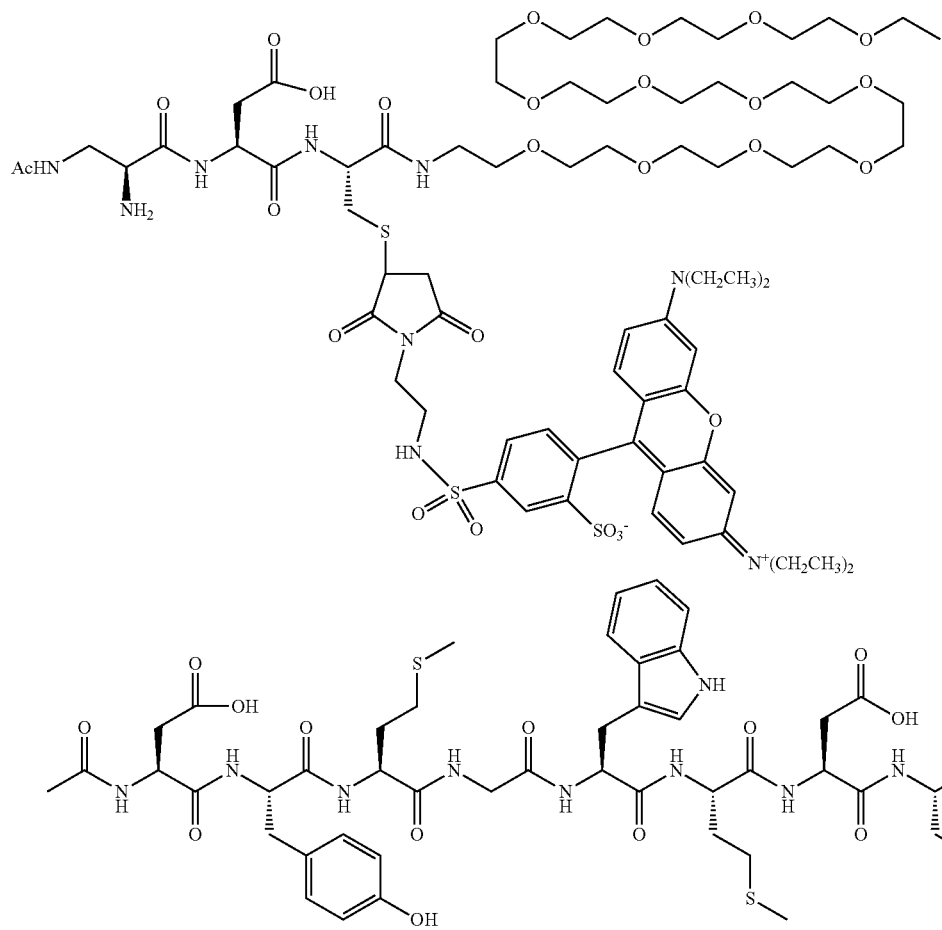

67. A pharmaceutical composition, comprising a conjugate of any one of the preceding clauses, or a pharmaceutically acceptable salt thereof, and optionally at least one excipient.

68. A method of treating abnormal cell growth in a mammal, including a human, the method comprising administering to the mammal a conjugate of any one of clauses 1-65.

69. The method of clause 68, wherein the abnormal cell growth is cancer.

70. The method of clause 69, wherein the cancer is selected from the group consisting of lung cancer, small cell lung cancer (SCLC), non-small cell lung cancer (NSCLC), bronchopulmonary carcinoid, bone cancer, pancreatic cancer, pancreatic ductal adenocarcinomas, skin cancer, cancer of the head or neck, cutaneous or intraocular melanoma, uterine cancer, ovarian cancer, rectal cancer, cancer of the anal region, stomach cancer, colon cancer, colorectal cancer, colorectal ductal adenocarcinomas, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, gastrointestinal cancer, insulinoma, ileal carcinoid, gastrointestinal stromal tumor (GIST), gastric ductal adenocarcinoma, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, cholangiocellular carcinoma, hepatocellular carcinoma, renal cell carcinoma, carcinoma of the renal pelvis, neoplasms of the central nervous system (CNS), primary CNS lymphoma, spinal axis tumors, brain stem glioma and pituitary adenoma 71. Use of a conjugate according to any one of clauses 1-65 in the preparation of a medicament for the treatment of cancer.

72. The use of clause 70, wherein the cancer is selected from the group consisting of lung cancer, small cell lung cancer (SCLC), non-small cell lung cancer (NSCLC), bronchopulmonary carcinoid, bone cancer, pancreatic cancer, pancreatic ductal adenocarcinomas, skin cancer, cancer of the head or neck, cutaneous or intraocular melanoma, uterine cancer, ovarian cancer, rectal cancer, cancer of the anal region, stomach cancer, colon cancer, colorectal cancer, colorectal ductal adenocarcinomas, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, gastrointestinal cancer, insulinoma, ileal carcinoid, gastrointestinal stromal tumor (GIST), gastric ductal adenocarcinoma, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, cholangiocellular carcinoma, hepatocellular carcinoma, renal cell carcinoma, carcinoma of the renal pelvis, neoplasms of the central nervous system (CNS), primary CNS lymphoma, spinal axis tumors, brain stem glioma and pituitary adenoma 73. A conjugate according to any one of clauses 1-65 for use in the treatment of the treatment of cancer.

74. The conjugate of clause 72, wherein the cancer is selected from the group consisting of lung cancer, small cell lung cancer (SCLC), non-small cell lung cancer (NSCLC), bronchopulmonary carcinoid, bone cancer, pancreatic cancer, pancreatic ductal adenocarcinomas, skin cancer, cancer of the head or neck, cutaneous or intraocular melanoma, uterine cancer, ovarian cancer, rectal cancer, cancer of the anal region, stomach cancer, colon cancer, colorectal cancer, colorectal ductal adenocarcinomas, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, gastrointestinal cancer, insulinoma, ileal carcinoid, gastrointestinal stromal tumor (GIST), gastric ductal adenocarcinoma, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, cholangiocellular carcinoma, hepatocellular carcinoma, renal cell carcinoma, carcinoma of the renal pelvis, neoplasms of the central nervous system (CNS), primary CNS lymphoma, spinal axis tumors, brain stem glioma and pituitary adenoma.

BRIEF DESCRIPTION OF THE DRAWINGS

FIG. 11 shows confocal microscope images of HEK-CCK2R GFP-overexpressing cells stained with EC1906.

DEFINITIONS

Figure 1:
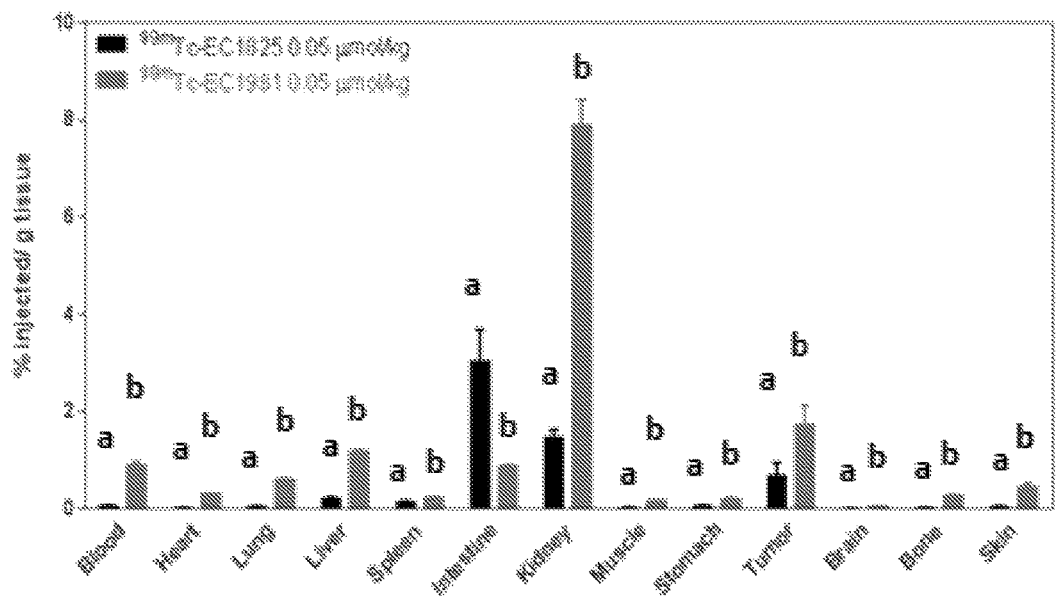
FIG. 1 shows the biodistribution of conjugates $^{99m}$Tc-EC1981 and $^{99m}$Tc-EC1825 in mice inoculated with HEK-CCK2R tumor cells, and administered 0.05 μmol/kg of $^{99m}$Tc-EC1981 and $^{99m}$Tc-EC1825. (a) $^{99m}$Tc-EC1825; (b) $^{99m}$Tc-EC1981.

As used herein, the term "alkyl" includes a chain of carbon atoms, which is optionally branched and contains from 1 to 20 carbon atoms. It is to be further understood that in certain embodiments, alkyl may be advantageously of limited length, including $C_1$-$C_{12}$, $C_1$-$C_{10}$, $C_1$-$C_9$, $C_1$-$C_8$, $C_1$-$C_7$, $C_1$-$C_6$, and $C_1$-$C_4$. Illustratively, such particularly limited length alkyl groups, including $C_1$-$C_8$, $C_1$-$C_7$, $C_1$-$C_6$, and $C_1$-$C_4$, and the like may be referred to as "lower alkyl." Illustrative alkyl groups include, but are not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, oxo, (=O), thiocarbonyl, O-carbamyl, N-carbamyl, O-thiocarbamyl, N-thiocarbamyl, C-amido, N-amido, C-carboxy, O-carboxy, nitro, and amino, or as described in the various embodiments provided herein. It will be understood that "alkyl" may be combined with other groups, such as those provided above, to form a functionalized alkyl. By way of example, the combination of an "alkyl" group, as described herein, with a "carboxy" group may be referred to as a "carboxyalkyl" group. Other non-limiting examples include hydroxyalkyl, aminoalkyl, and the like.

As used herein, the term "alkenyl" includes a chain of carbon atoms, which is optionally branched, and contains from 2 to 20 carbon atoms, and also includes at least one carbon-carbon double bond (i.e. C=C). It will be understood that in certain embodiments, alkenyl may be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkenyl groups, including $C_2$-$C_8$, $C_2$-$C_7$, $C_2$-$C_6$, and $C_2$-$C_4$ may be referred to as lower alkenyl. Alkenyl may be unsubstituted, or substituted as described for alkyl or as described in the various embodiments provided herein. Illustrative alkenyl groups include, but are not limited to, ethenyl, 1-propenyl, 2-propenyl, 1-, 2-, or 3-butenyl, and the like.

As used herein, the term "alkynyl" includes a chain of carbon atoms, which is optionally branched, and contains from 2 to 20 carbon atoms, and also includes at least one carbon-carbon triple bond (i.e. C≡C). It will be understood that in certain embodiments alkynyl may each be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkynyl groups, including $C_2$-$C_8$, $C_2$-$C_7$, $C_2$-$C_6$, and $C_2$-$C_4$ may be referred to as lower alkynyl. Alkenyl may be unsubstituted, or substituted as described for alkyl or as described in the various embodiments provided herein. Illustrative alkenyl groups include, but are not limited to, ethynyl, 1-propynyl, 2-propynyl, 1-, 2-, or 3-butynyl, and the like.

As used herein, the term "aryl" refers to an all-carbon monocyclic or fused-ring polycyclic groups of 6 to 12 carbon atoms having a completely conjugated pi-electron system. It will be understood that in certain embodiments, aryl may be advantageously of limited size such as $C_6$-$C_{10}$ aryl. Illustrative aryl groups include, but are not limited to, phenyl, naphthalenyl and anthracenyl. The aryl group may be unsubstituted, or substituted as described for alkyl or as described in the various embodiments provided herein.

As used herein, the term "cycloalkyl" refers to a 3 to 15 member all-carbon monocyclic ring, an all-carbon 5-member/6-member or 6-member/6-member fused bicyclic ring, or a multicyclic fused ring (a "fused" ring system means that each ring in the system shares an adjacent pair of carbon atoms with each other ring in the system) group where one or more of the rings may contain one or more double bonds but the cycloalkyl does not contain a completely conjugated pi-electron system. It will be understood that in certain embodiments, cycloalkyl may be advantageously of limited size such as $C_3$-$C_{13}$, $C_3$-$C_6$, $C_3$-$C_6$ and $C_4$-$C_6$. Cycloalkyl may be unsubstituted, or substituted as described for alkyl or as described in the various embodiments provided herein. Illustrative cycloalkyl groups include, but are not limited to, cyclopropyl, cyclobutyl, cyclopentyl, cyclopentenyl, cyclopentadienyl, cyclohexyl, cyclohexenyl, cycloheptyl, adamantyl, norbornyl, norbornenyl, 9H-fluoren-9-yl, and the like.

As used herein, the term "heterocycloalkyl" refers to a monocyclic or fused ring group having in the ring(s) from 3 to 12 ring atoms, in which at least one ring atom is a heteroatom, such as nitrogen, oxygen or sulfur, the remaining ring atoms being carbon atoms. Heterocycloalkyl may optionally contain 1, 2, 3 or 4 heteroatoms. Heterocycloalkyl may also have one of more double bonds, including double bonds to nitrogen (e.g. C=N or N=N) but does not contain a completely conjugated pi-electron system. It will be understood that in certain embodiments, heterocycloalkyl may be advantageously of limited size such as 3- to 7-membered heterocycloalkyl, 5- to 7-membered heterocycloalkyl, and the like. Heterocycloalkyl may be unsubstituted, or substituted as described for alkyl or as described in the various embodiments provided herein. Illustrative heterocycloalkyl groups include, but are not limited to, oxiranyl, thianaryl, azetidinyl, oxetanyl, tetrahydrofuranyl, pyrrolidinyl, tetrahydropyranyl, piperidinyl, 1,4-dioxanyl, morpholinyl, 1,4-dithianyl, piperazinyl, oxepanyl, 3,4-dihydro-2H-pyranyl, 5,6-dihydro-2H-pyranyl, 2H-pyranyl, 1, 2, 3, 4-tetrahydropyridinyl, and the like.

As used herein, the term "heteroaryl" refers to a monocyclic or fused ring group of 5 to 12 ring atoms containing one, two, three or four ring heteroatoms selected from nitrogen, oxygen and sulfur, the remaining ring atoms being carbon atoms, and also having a completely conjugated pi-electron system. It will be understood that in certain embodiments, heteroaryl may be advantageously of limited size such as 3- to 7-membered heteroaryl, 5- to 7-membered heteroaryl, and the like. Heteroaryl may be unsubstituted, or substituted as described for alkyl or as described in the various embodiments provided herein. Illustrative heteroaryl groups include, but are not limited to, pyrrolyl, furanyl, thiophenyl, imidazolyl, oxazolyl, thiazolyl, pyrazolyl, pyridinyl, pyrimidinyl, quinolinyl, isoquinolinyl, purinyl, tetrazolyl, triazinyl, pyrazinyl, tetrazinyl, quinazolinyl, quinoxalinyl, thienyl, isoxazolyl, isothiazolyl, oxadiazolyl, thiadiazolyl, triazolyl, benzimidazolyl, benzoxazolyl, benzthiazolyl, benzisoxazolyl, benzisothiazolyl and carbazoloyl, and the like.

As used herein, "hydroxy" or "hydroxyl" refers to an —OH group.

As used herein, "alkoxy" refers to both an —O-(alkyl) or an —O-(unsubstituted cycloalkyl) group. Representative examples include, but are not limited to, methoxy, ethoxy, propoxy, butoxy, cyclopropyloxy, cyclobutyloxy, cyclopentyloxy, cyclohexyloxy, and the like.

As used herein, "aryloxy" refers to an —O-aryl or an —O-heteroaryl group. Representative examples include, but are not limited to, phenoxy, pyridinyloxy, furanyloxy, thienyloxy, pyrimidinyloxy, pyrazinyloxy, and the like, and the like.

As used herein, "mercapto" refers to an —SH group.

As used herein, "alkylthio" refers to an —S-(alkyl) or an —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

As used herein, "arylthio" refers to an —S-aryl or an —S-heteroaryl group. Representative examples include, but are not limited to, phenylthio, pyridinylthio, furanylthio, thienylthio, pyrimidinylthio, and the like.

As used herein, "halo" or "halogen" refers to fluorine, chlorine, bromine or iodine.

As used herein, "trihalomethyl" refers to a methyl group having three halo substituents, such as a trifluoromethyl group.

As used herein, "cyano" refers to a —CN group.

As used herein, "sulfinyl" refers to a —S(O)$R^a$ group, where $R^a$ is any variable group as described in the various embodiments provided herein, or $R^a$ may be a hydroxyl group.

As used herein, "sulfonyl" refers to a —S(O)$_2$$R^a$ group, where $R^a$ is any variable group as described in the various embodiments provided herein, or $R^a$ may be a hydroxyl group.

As used herein, "S-sulfonamido" refers to a —S(O)$_2$NR$^a$R$^b$ group, where R$^a$ and R$^b$ are any variable group as described in the various embodiments provided herein.

As used herein, "N-sulfonamido" refers to a —NR$^a$S(O)$_2$R$^b$ group, where R$^a$ and R$^b$ are any variable group as described in the various embodiments provided herein.

As used herein, "O-carbamyl" refers to a —OC(O)NR$^a$R$^b$ group, where R$^a$ and R$^b$ are any variable group as described in the various embodiments provided herein.

As used herein, "N-carbamyl" refers to an R$^a$OC(O)NR$^b$— group, where R$^a$ and R$^b$ are any variable group as described in the various embodiments provided herein.

As used herein, "O-thiocarbamyl" refers to a —OC(S)NR$^a$R$^b$ group, where R$^a$ and R$^b$ are any variable group as described in the various embodiments provided herein.

As used herein, "N-thiocarbamyl" refers to a R$^a$OC(S)NR$^b$— group, where R$^a$ and R$^b$ are any variable group as described in the various embodiments provided herein.

As used herein, "amino" refers to an —NR$^a$R$^b$ group, where R$^a$ and R$^b$ are any variable group as described in the various embodiments provided herein.

As used herein, "C-amido" refers to a —C(O)NR$^a$R$^b$ group, where R$^a$ and R$^b$ are any variable group as described in the various embodiments provided herein.

As used herein, "N-amido" refers to a R$^a$C(O)NR$^b$— group, where R$^a$ and R$^b$ are any variable group as described in the various embodiments provided herein.

As used herein, "nitro" refers to a —NO$_2$ group.

As used herein, "bond" refers to a covalent bond.

As used herein, "optional" or "optionally" means that the subsequently described event or circumstance may but need not occur, and that the description includes instances where the event or circumstance occurs and instances in which it does not. For example, "heterocycle group optionally substituted with an alkyl group" means that the alkyl may but need not be present, and the description includes situations where the heterocycle group is substituted with an alkyl group and situations where the heterocycle group is not substituted with the alkyl group.

As used herein, "independently" means that the subsequently described event or circumstance is to be read on its own relative to other similar events or circumstances. For example, in a circumstance where several equivalent hydrogen groups are optionally substituted by another group described in the circumstance, the use of "independently optionally" means that each instance of a hydrogen atom on the group may be substituted by another group, where the groups replacing each of the hydrogen atoms may be the same or different. Or for example, where multiple groups exist all of which can be selected from a set of possibilities, the use of "independently" means that each of the groups can be selected from the set of possibilities separate from any other group, and the groups selected in the circumstance may be the same or different.

As used herein, the term "pharmaceutically acceptable salt" refers to those salts which counter ions which may be used in pharmaceuticals. Such salts include:

(1) acid addition salts, which can be obtained by reaction of the free base of the parent conjugate with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methane sulfonic acid, ethanesulfonic acid, p-toluenesulfonic acid, salicylic acid, tartaric acid, citric acid, succinic acid or malonic acid and the like; or (2) salts formed when an acidic proton present in the parent conjugate either is replaced by a metal ion, e.g., an alkali metal ion, an alkaline earth ion, or an aluminum ion; or coordinates with an organic base such as ethanolamine, diethanolamine, triethanolamine, trimethamine, N-methylglucamine, and the like.

Pharmaceutically acceptable salts are well known to those skilled in the art, and any such pharmaceutically acceptable salt may be contemplated in connection with the embodiments described herein As used herein, "amino acid" (a.k.a. "AA") means any molecule that includes an alpha-carbon atom covalently bonded to an amino group and an acid group. The acid group may include a carboxyl group. "Amino acid" may include molecules having one of the formulas:

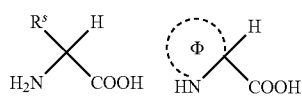

wherein R$^s$ is a side group and Φ includes at least 3 carbon atoms. "Amino acid" includes stereoisomers such as the D-amino acid and L-amino acid forms. Illustrative amino acid groups include, but are not limited to, the twenty endogenous human amino acids and their derivatives, such as lysine (Lys), asparagine (Asn), threonine (Thr), serine (Ser), isoleucine (Ile), methionine (Met), proline (Pro), histidine (His), glutamine (Gln), arginine (Arg), glycine (Gly), aspartic acid (Asp), glutamic acid (Glu), alanine (Ala), valine (Val), phenylalanine (Phe), leucine (Leu), tyrosine (Tyr), cysteine (Cys), tryptophan (Trp), phosphoserine (PSER), sulfo-cysteine, arginosuccinic acid (ASA), hydroxyproline, phosphoethanolamine (PEA), sarcosine (SARC), taurine (TAU), carnosine (CARN), citrulline (CIT), anserine (ANS), 1,3-methyl-histidine (ME-HIS), alpha-amino-adipic acid (AAA), beta-alanine (BALA), ethanolamine (ETN), gamma-amino-butyric acid (GABA), beta-amino-isobutyric acid (BAIA), alpha-amino-butyric acid (BABA), L-allo-cystathionine (cystathionine-A; CYSTA-A), L-cystathionine (cystathionine-B; CYSTA-B), cystine, allo-isoleucine (ALLO-ILE), DL-hydroxylysine (hydroxylysine (I)), DL-allo-hydroxylysine (hydroxylysine (2)), ornithine (ORN), homocystine (HCY), 3-amino-L-alanine (L-2,3-diaminopropionic acid or Dap) and derivatives thereof. It will be appreciated that each of these examples are also contemplated in connection with the present disclosure in the D-configuration as noted above. Specifically, for example, D-lysine (D-Lys), D-asparagine (D-Asn), D-threonine (D-Thr), D-serine (D-Ser), D-isoleucine (D-Ile), D-methionine (D-Met), D-proline (D-Pro), D-histidine (D-His), D-glutamine (D-Gln), D-arginine (D-Arg), D-glycine (D-Gly), D-aspartic acid (D-Asp), D-glutamic acid (D-Glu), D-alanine (D-Ala), D-valine (D-Val), D-phenylalanine (D-Phe), D-leucine (D-Leu), D-tyrosine (D-Tyr), D-cysteine (D-Cys), D-tryptophan (D-Trp), D-citrulline (D-CIT), D-carnosine (D-CARN), and the like. In connection with the embodiments described herein, amino acids can be covalently attached to other portions of the conjugates described herein through their alpha-amino and carboxy functional groups (i.e. in a peptide bond configuration), or through their side chain functional groups (such as the side chain carboxy group in glutamic acid) and either their alpha-amino or carboxy functional groups. It will be understood that amino acids, when used in connection with the conjugates described herein, may exist as zwitterions in a conjugate in which they are incorporated.

As used herein, "prodrug" refers to a compound that can be administered to a subject in a pharmacologically inactive form which then can be converted to a pharmacologically active form through a normal metabolic process, such as hydrolysis of an oxazolidine. It will be understood that the metabolic processes through which a prodrug can be converted to an active drug include, but are not limited to, one or more spontaneous chemical reaction(s), enzyme-catalyzed chemical reaction(s), and/or other metabolic chemical reaction(s), or a combination thereof. It will be appreciated that understood that a variety of metabolic processes are known in the art, and the metabolic processes through which the prodrugs described herein are converted to active drugs are non-limiting. A prodrug can be a precursor chemical compound of a drug that has a therapeutic effect on a subject.

As used herein, the term "therapeutically effective amount" refers to an amount of a drug or pharmaceutical agent that elicits the biological or medicinal response in a subject (i.e. a tissue system, animal or human) that is being sought by a researcher, veterinarian, medical doctor or other clinician, which includes, but is not limited to, alleviation of the symptoms of the disease or disorder being treated. In one aspect, the therapeutically effective amount is that amount of an active which may treat or alleviate the disease or symptoms of the disease at a reasonable benefit/risk ratio applicable to any medical treatment. In another aspect, the therapeutically effective amount is that amount of an inactive prodrug which when converted through normal metabolic processes to produce an amount of active drug capable of eliciting the biological or medicinal response in a subject that is being sought.

It is also appreciated that the dose, whether referring to monotherapy or combination therapy, is advantageously selected with reference to any toxicity, or other undesirable side effect, that might occur during administration of one or more of the conjugates described herein. Further, it is appreciated that the co-therapies described herein may allow for the administration of lower doses of conjugates that show such toxicity, or other undesirable side effect, where those lower doses are below thresholds of toxicity or lower in the therapeutic window than would otherwise be administered in the absence of a cotherapy.

As used herein, "administering" includes all means of introducing the conjugates and compositions described herein to the host animal, including, but are not limited to, oral (po), intravenous (iv), intramuscular (im), subcutaneous (sc), transdermal, inhalation, buccal, ocular, sublingual, vaginal, rectal, and the like. The conjugates and compositions described herein may be administered in unit dosage forms and/or formulations containing conventional nontoxic pharmaceutically-acceptable carriers, adjuvants, and/or vehicles.

As used herein, "pharmaceutical composition" or "composition" refers to a mixture of one or more of the conjugates described herein, or pharmaceutically acceptable salts, solvates, hydrates thereof, with other chemical components, such as pharmaceutically acceptable excipients. The purpose of a pharmaceutical composition is to facilitate administration of a conjugate to a subject. Pharmaceutical compositions suitable for the delivery of conjugates described and methods for their preparation will be readily apparent to those skilled in the art. Such compositions and methods for their preparation may be found, for example, in 'Remington's Pharmaceutical Sciences', 19th Edition (Mack Publishing Company, 1995).

A "pharmaceutically acceptable excipient" refers to an inert substance added to a pharmaceutical composition to further facilitate administration of a conjugate such as a diluent or a carrier.

As used herein, "counter-ion" refers to any ion that accompanies an ionic species in order to maintain electric neutrality that is known in the art. Suitable counter-ions can be metal ions such as Na$^+$, Mg$^{++}$, K$^+$ and the like, or organic ions (e.g. lipophilic cations), such as quaterary ammonium cations, such as tetramethylammonium, tetraethylammonium, tetrabuylammonium, and the like. It will be appreciated that the exact nature or identity of a counter-ion suitable for use in connection with the present disclosure is not particularly limited.

DETAILED DESCRIPTION

In each of the foregoing and each of the following embodiments, it is to be understood that the formulae include and represent not only all pharmaceutically acceptable salts of the conjugates, but also include any and all hydrates and/or solvates of the conjugate formulae. It is appreciated that certain functional groups, such as the hydroxy, amino, and like groups form complexes and/or coordination conjugates with water and/or various solvents, in the various physical forms of the conjugates. Accordingly, the above formulae are to be understood to include and represent those various hydrates and/or solvates. It is also to be understood that the non-hydrates and/or non-solvates of the conjugate formulae are described by such formula, as well as the hydrates and/or solvates of the conjugate formulae.

As used herein, the term cell surface receptor binding ligand (aka a "binding ligand"), generally refers to compounds that bind to and/or target receptors that are found on cell surfaces, and in particular those that are found on, over-expressed by, and/or preferentially expressed on the surface of pathogenic cells. Binding ligands include, but are not limited to, those that target CCK2R. Examples of CCK2R binding ligands include non-peptidic agonists and antagonists of CCK2R that have been described in the literature (See for example, Wayua, C. et al., *J. Nucl. Med.*, 56, 1, 113-9 (2015)), and peptidic agonists and antagonists of CCK2R.

In the case of non-peptidic CCK2R binding ligands, the binding ligand can be of the type described in United Stated Patent Publication US2012/0010401A1. Such non-peptidic binding ligands include those described by the formula

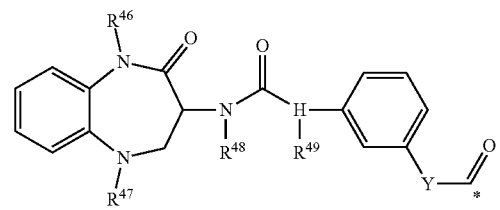

wherein
Y is a bond or a $C_1$-$C_6$ alkyl;
each of $R^{46}$, $R^{47}$, $R^{48}$ and $R^{49}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —OR$^{50}$, —OC(O)R$^{50}$, —OC(O)NR$^{50}$R$^{50'}$, —OS(O)R$^{50}$, —OS(O)$_2$R$^{50}$, —SR$^{50'}$, —S(O)R$^{50}$, —S(O)$_2$R$^{50}$, —S(O)NR$^{50}$R$^{50'}$, —S(O)$_2$NR$^{50}$R$^{50'}$, —OS(O)NR$^{50}$R$^{50'}$, —OS(O)$_2$NR$^{50}$R$^{50'}$, —NR$^{50}$R$^{50'}$, —NR$^{50}$C(O)R$^{51}$, —NR$^{50}$C(O)OR$^{51}$, —NR$^{50}$C(O)NR$^{51}$R$^{51'}$, —NR$^{50}$S(O)R$^{51}$, —NR$^{50}$S(O)$_2$R$^{51}$, —NR$^{50}$S(O)NR$^{51}$R$^{51'}$, —NR$^{50}$S(O)$_2$NR$^{51}$R$^{51'}$, —C(O)R$^{50}$, —C(O)OR$^{50}$ or —C(O)NR$^{50}$R$^{50}$; and
each $R^{50}$, $R^{50'}$, $R^{51}$ and $R^{51'}$ is independently H, $C_1$-$C_6$ alkyl, $C_2$-$C_6$ alkenyl, $C_2$-$C_6$ alkynyl or $C_3$-$C_6$ cycloalkyl.

In some embodiments, the CCK2R binding ligand is a compound of the formula

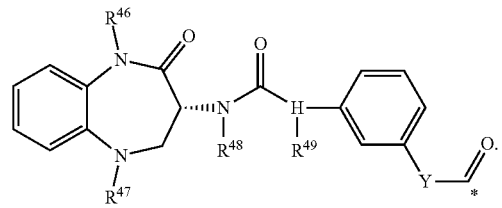

In some embodiments, $R^{46}$ is —CH$_2$C(O)C(CH$_3$)$_3$. In some embodiments, $R^{47}$ is cyclohexyl. In some embodiments, $R^{48}$ and $R^{49}$ are H. In some embodiments, Y is a bond. In some embodiments, $R^{46}$ is —CH$_2$C(O)C(CH$_3$)$_3$, $R^{47}$ is cyclohexyl, $R^{48}$ and $R^{49}$ are H; and Y is a bond.

In the case of peptidic CCK2R binding ligands, the sequence of the binding ligand can be any sequence capable of recognizing and sequestering the CCK2R receptor. Such peptidic binding ligands include those having unnatural amino acids in the sequence. For example, peptidic binding ligands can include one or more amino acids having a D-configuration. In addition, such peptidic binding ligands can include one or more amino acids having an unnatural or derivitized side chain group, such as a sulfated side chain.

In some embodiments, peptidic binding ligands useful in connection with the present disclosure can be peptides of from 6 to 10 amino acids in length capable of binding to CCK2R. In some embodiments, peptidic binding ligands useful in connection with the present disclosure can be peptides of from 6 to 10 amino acids in length where the amino acids are each independently selected from the group consisting of methionine (Met), glycine (Gly), aspartic acid (Asp), phenylalanine (Phe), tyrosine (Tyr) and tryptophan (Trp). In some embodiments, peptidic binding ligands useful in connection with the present disclosure include an amino acid sequence of Met-Gly-Trp-Met-Asp-Phe. In some embodiments, peptidic binding ligands useful in connection with the present disclosure include an amino acid sequence of Tyr-Met-Gly-Trp-Met-Asp-Phe. In some embodiments, peptidic binding ligands useful in connection with the present disclosure include an amino acid sequence of Tyr-Met-Gly-Trp-Met-Asp-Phe, wherein one or more of the amino acids in the sequence are an unnatural amino acid. In some embodiments, peptidic binding ligands useful in connection with the present disclosure include an amino acid sequence of Tyr-Met-Gly-Trp-Met-Asp-Phe, wherein one or more of the amino acids in the sequence have an unnatural or derivitized side chain group, such as a sulfated side chain. In some embodiments, peptidic binding ligands useful in connection with the present disclosure include an amino acid sequence of Asp-Tyr-Met-Gly-Trp-Met-Asp-Phe. In some embodiments, peptidic binding ligands useful in connection with the present disclosure include an amino acid sequence of Asp-Tyr-Met-Gly-Trp-Met-Asp-Phe, wherein one or more of the amino acids in the sequence are an unnatural amino acid. In some embodiments, peptidic binding ligands useful in connection with the present disclosure include an amino acid sequence of Asp-Tyr-Met-Gly-Trp-Met-Asp-Phe, wherein one or more of the amino acids in the sequence have an unnatural or derivitized side chain group, such as a sulfated side chain.

In some embodiments, the binding ligand can be of the formula

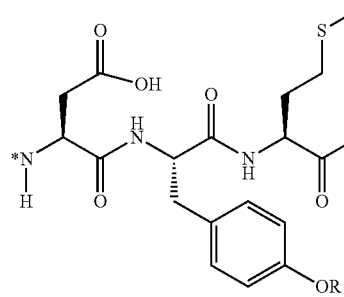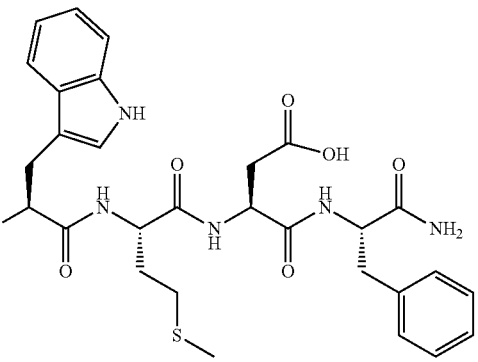

wherein R is H, —SO$_3^-$ or —SO$_3$M, wherein M is a counter-ion, and wherein * is a covalent bond attaching the binding ligand to a linker as described herein.

In some embodiments, L is a releasable linker. In some embodiments L comprises one or more of the moieties L$^1$, L$^2$ and L$^3$, as defined herein. In some embodiments, L further comprises at least one amino acid (AA) as defined herein. As used herein, the term "releasable linker" refers to a linker that includes at least one bond that can be broken under physiological conditions, such as a pH-labile, acid-labile, base-labile, oxidatively labile, metabolically labile, biochemically labile, or enzyme-labile bond (a "releasable moiety" or "cleavable bond"). It is appreciated that such physiological conditions resulting in bond breaking do not necessarily include a biological or metabolic process, and instead may include a standard chemical reaction, such as a hydrolysis reaction, for example, at physiological pH, or as a result of compartmentalization into a cellular organelle such as an endosome having a lower pH than cytosolic pH.

It is understood that a cleavable bond can connect two adjacent atoms within the releasable linker and/or connect other linkers, B or D, as described herein, at either or both ends of the releasable linker. In the case where a cleavable bond connects two adjacent atoms within the releasable linker, following breakage of the bond, the releasable linker is broken into two or more fragments. Alternatively, in the case where a cleavable bond is between the releasable linker and another moiety, such as another linker, a drug or binding ligand, the releasable linker becomes separated from the other moiety following breaking of the bond.

The lability of the cleavable bond can be adjusted by, for example, substituents at or near the cleavable bond, such as including alpha-branching adjacent to a cleavable disulfide bond.

In some embodiments, releasable linkers described herein include one or more cleavable functional groups, such as a disulfide, a carbonate, a carbamate, a hydrazine, an amide, an ester, and the like. Illustrative cleavable functional group included in the releasable linkers described herein include hemiacetals and sulfur variations thereof, acetals and sulfur variations thereof, hemiaminals, aminals, and the like, and can be formed from methylene fragments substituted with at least one heteroatom, 1-alkoxy alkylene, 1-alkoxycycloalkylene, 1-alkoxyalkylenecarbonyl, 1-alkoxycycloalkylene-carbonyl, and the like. Illustrative releasable linkers described herein include linkers that include carbonylarylcarbonyl, carbonyl(carboxyaryl)carbonyl, carbonyl(biscarboxyaryl) carbonyl, haloalkylenecarbonyl, and the like. Illustrative releasable linkers described herein include linkers that include alkylene(dialkylsilyl), alkylene(alkylarylsilyl), alkylene(diarylsilyl), (dialkylsilyl)aryl, (alkylarylsilyl)aryl, (diarylsilyl)aryl, and the like. Illustrative releasable linkers described herein include oxycarbonyloxy, oxycarbonyloxyalkyl, sulfonyloxy, oxysulfonylalkyl, and the like. Illustrative releasable linkers described herein include functional groups that include iminoalkylidenyl, carbonylalkylideniminyl, iminocycloalkylidenyl, carbonylcycloalkyliden-iminyl, and the like. Illustrative releasable linkers described herein include functional groups that include alkylenethio, alkylenearylthio, and carbonylalkylthio, and the like.

In some embodiments, the conjugates described herein comprise more than one cleavable functional group. It will be appreciated that when the conjugates described herein comprise more than one cleavable functional group, the cleavable functional groups may be the same. It will be further appreciated that when the conjugates described herein comprise more than one cleavable functional group, the cleavable functional groups may be different. In some embodiments, the conjugates described herein comprise more than one cleavable functional group, wherein at least one cleavable functional group comprises is a disulfide bond.

In some embodiments, L comprises a moiety $L^1$ of the formula selected from the group consisting of

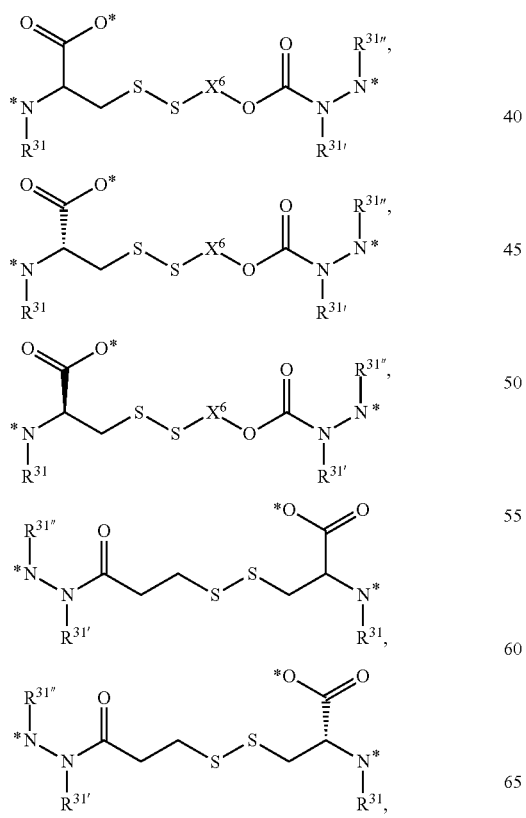
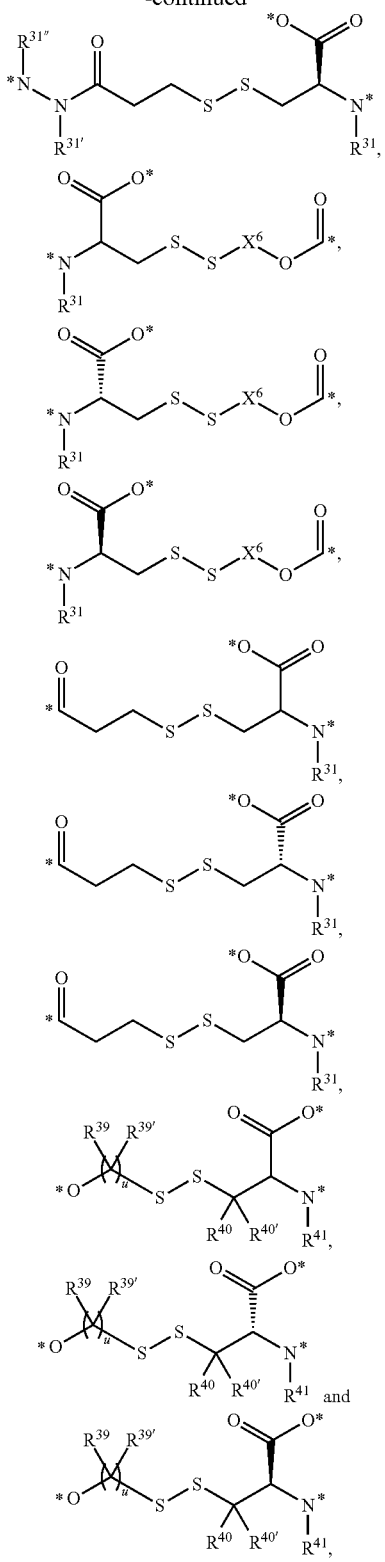

wherein
each $R^{31}$, $R^{31'}$ and $R^{31''}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{32}$, $OC(O)R^{32}$, —$OC(O)NR^{32}R^{32'}$, —$OS(O)R^{32}$, —$OS(O)_2R^{32}$, —$SR^{32}$, —$S(O)R^{32}$, —$S(O)_2R^{32}$, —$S(O)NR^{32}R^{32'}$, —$S(O)_2NR^{32}R^{32'}$, —$OS(O)NR^{32}R^{32'}$, —$OS(O)_2NR^{32}R^{32'}$, —$NR^{32}R^{32'}$, —$NR^{32}C(O)R^{33}$, —$NR^{32}C(O)OR^{33}$, —$NR^{32}C(O)NR^{33}R^{33'}$, —$NR^{32}S(O)R^{33}$, —$NR^{32}S(O)_2R^{33}$, —$NR^{32}S(O)NR^{33}R^{33'}$, —$NR^{32}S(O)_2NR^{33}R^{33'}$, —$C(O)R^{32}$, —$C(O)OR^{32}$ or —$C(O)NR^{32}R^{32'}$;

each $X^6$ is independently $C_1$-$C_6$ alkyl or $C_6$-$C_{10}$ aryl($C_1$-$C_6$ alkyl), wherein each hydrogen atom in $C_1$-$C_6$ alkyl and $C_6$-$C_{10}$ aryl($C_1$-$C_6$ alkyl) is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{34}$, —$OC(O)R^{34}$, —$OC(O)NR^{34}R^{34'}$, —$OS(O)R^{34}$, —$OS(O)_2R^{34}$, —$SR^{34}$, —$S(O)R^{34}$, —$S(O)_2R^{34}$, —$S(O)NR^{34}R^{34'}$, —$S(O)_2NR^{34}R^{34'}$, —$OS(O)NR^{34}R^{34'}$, —$OS(O)_2NR^{34}R^{34'}$, —$NR^{34}R^{34'}$, —$NR^{34}C(O)R^{35}$, —$NR^{34}C(O)OR^{35}$, —$NR^{34}C(O)NR^{35}R^{35'}$, —$NR^{34}S(O)R^{35}$, —$NR^{34}S(O)_2R^{35}$, —$NR^{34}S(O)NR^{35}R^{35'}$, —$NR^{34}S(O)_2NR^{35}R^{35'}$, —$C(O)R^{34}$, —$C(O)OR^{34}$ or —$C(O)NR^{34}R^{34'}$;

each $R^{32}$, $R^{32'}$, $R^{33}$, $R^{33'}$, $R^{34}$, $R^{34'}$, $R^{35}$ and $R^{35'}$ is independently selected from the group consisting of H, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl;

each $R^{39}$, $R^{39'}$, $R^{40}$ and $R^{40'}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{44}$, —$OC(O)R^{44}$, —$OC(O)NR^{44}R^{44'}$, —$OS(O)R^{44}$, —$OS(O)_2R^{44}$, —$SR^{44}$, —$S(O)R^{44}$, —$S(O)_2R^{44}$, —$S(O)NR^{44}R^{44'}$, —$S(O)_2NR^{44}R^{44'}$, —$OS(O)NR^{44}R^{44'}$, —$OS(O)_2NR^{44}R^{44'}$, —$NR^{44}R^{44'}$, —$NR^{44}C(O)R^{45}$, $NR^{44}C(O)OR^{45}$, —$NR^{44}C(O)NR^{45}R^{45'}$, —$NR^{44}S(O)R^{45}$, —$NR^{44}S(O)_2R^{45}$, —$NR^{44}S(O)NR^{45}R^{45'}$, —$NR^{44}S(O)_2NR^{45}R^{45'}$, —$C(O)R^{44}$, —$C(O)OR^{44}$ or —$C(O)NR^{44}R^{44'}$;

each $R^{41}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{42}$, $OC(O)R^{42}$, —$OC(O)NR^{42}R^{42'}$, —$OS(O)R^{42}$, —$OS(O)_2R^{42}$, —$SR^{42}$, —$S(O)R^{42}$, —$S(O)_2R^{42}$, —$S(O)NR^{42}R^{42'}$, —$S(O)_2NR^{42}R^{42'}$, —$OS(O)NR^{42}R^{42'}$, —$OS(O)_2NR^{42}R^{42'}$, —$NR^{42}R^{42'}$, —$NR^{42}C(O)R^{43}$, —$NR^{42}C(O)OR^{43}$, —$NR^{42}C(O)NR^{43}R^{43'}$, —$NR^{42}S(O)R^{43}$, —$NR^{42}S(O)_2R^{43}$, —$NR^{42}S(O)NR^{43}R^{43'}$, —$NR^{42}S(O)_2NR^{43}R^{43'}$, —$C(O)R^{42}$, —$C(O)OR^{42}$ or —$C(O)NR^{42}R^{42'}$;

each $R^{42}$, $R^{42'}$, $R^{43}$, $R^{43'}$, $R^{44}$, $R^{44'}$, $R^{45}$, and $R^{45'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl; and u is 1, 2, 3 or 4;

wherein * is a covalent bond.

In some embodiments, L comprises a moiety $L^1$ of the formula selected from the group consisting of

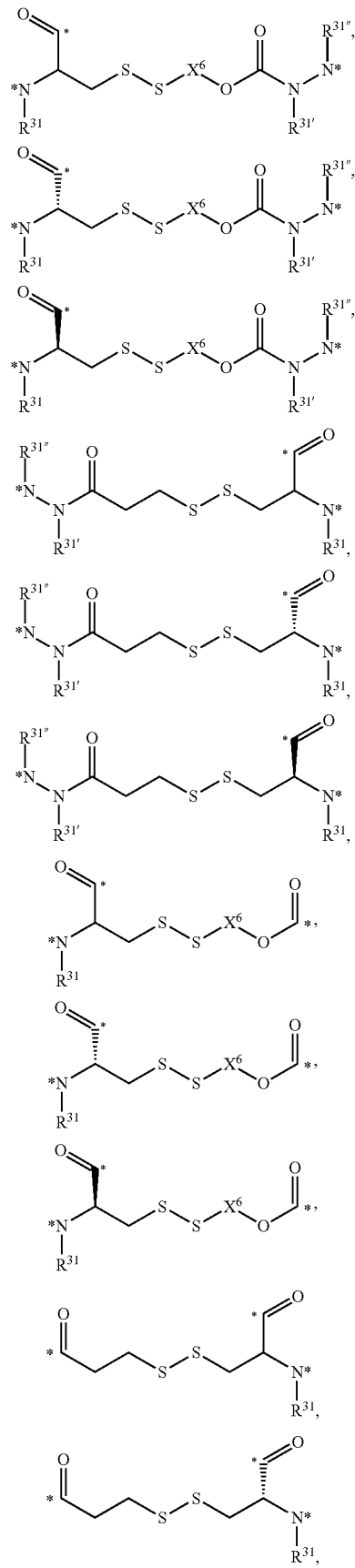

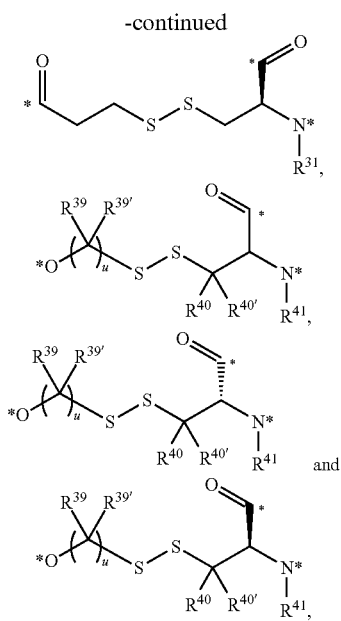

wherein each $R^{31}$, $R^{31'}$ and $R^{31''}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{32}$, $OC(O)R^{32}$, —$OC(O)NR^{32}R^{32'}$, —$OS(O)R^{32}$, —$OS(O)_2R^{32}$, —$SR^{32}$, —$S(O)R^{32}$, —$S(O)_2R^{32}$, —$S(O)NR^{32}R^{32'}$, —$S(O)_2NR^{32}R^{32'}$, —$OS(O)NR^{32}R^{32'}$, —$OS(O)_2NR^{32}R^{32'}$, —$NR^{32}R^{32'}$, —$NR^{32}C(O)R^{33}$, —$NR^{32}C(O)OR^{33}$, —$NR^{32}C(O)NR^{33}R^{33'}$, —$NR^{32}S(O)R^{33}$, —$NR^{32}S(O)_2R^{33}$, —$NR^{32}S(O)NR^{33}R^{33'}$, —$NR^{32}S(O)_2NR^{33}R^{33'}$, —$C(O)R^{32}$, —$C(O)OR^{32}$ or —$C(O)NR^{32}R^{32'}$;

each $X^6$ is independently $C_1$-$C_6$ alkyl or $C_6$-$C_{10}$ aryl($C_1$-$C_6$ alkyl), wherein each hydrogen atom in $C_1$-$C_6$ alkyl and $C_6$-$C_{10}$ aryl($C_1$-$C_6$ alkyl) is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{34}$, —$OC(O)R^{34}$, —$OC(O)NR^{34}R^{34'}$, —$OS(O)R^{34}$, —$OS(O)_2R^{34}$, —$SR^{34}$, —$S(O)R^{34}$, —$S(O)_2R^{34}$, —$S(O)NR^{34}R^{34'}$, —$S(O)_2NR^{34}R^{34'}$, —$OS(O)NR^{34}R^{34'}$, —$OS(O)_2NR^{34}R^{34'}$, —$NR^{34}R^{34'}$, —$NR^{34}C(O)R^{35}$, $NR^{34}C(O)OR^{35}$, —$NR^{34}C(O)NR^{35}R^{35'}$, —$NR^{34}S(O)R^{35}$, —$NR^{34}S(O)_2R^{35}$, —$NR^{34}S(O)NR^{35}R^{35'}$, —$NR^{34}S(O)_2NR^{35}R^{35'}$, —$C(O)R^{34}$, —$C(O)OR^{34}$ or —$C(O)NR^{34}R^{34'}$;

each $R^{32}$, $R^{32'}$, $R^{33}$, $R^{33'}$, $R^{34}$, $R^{34'}$, $R^{35}$ and $R^{35'}$ is independently selected from the group consisting of H, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl;

each $R^{39}$, $R^{39'}$, $R^{40}$ and $R^{40'}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{44}$, —$OC(O)R^{44}$, —$OC$
(O)$NR^{44}R^{44'}$, —$OS(O)R^{44}$, —$OS(O)_2R^{44}$, —$SR^{44}$, —$S(O)R^{44}$, —$S(O)_2R^{44}$, —$S(O)NR^{44}R^{44'}$, —$S(O)_2NR^{44}R^{44'}$, —$OS(O)NR^{44}R^{44'}$, —$OS(O)_2NR^{44}R^{44'}$, —$NR^{44}R^{44'}$, —$NR^{44}C(O)R^{45}$, $NR^{44}C(O)OR^{45}$, —$NR^{44}C(O)NR^{45}R^{45'}$, —$NR^{44}S(O)R^{45}$, —$NR^{44}S(O)_2R^{45}$, —$NR^{44}S(O)NR^{45}R^{45'}$, —$NR^{44}S(O)_2NR^{45}R^{45'}$, —$C(O)R^{44}$, —$C(O)OR^{44}$ or —$C(O)NR^{44}R^{44'}$;

each $R^{41}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{42}$, $OC(O)R^{42}$, —$OC(O)NR^{42}R^{42'}$, —$OS(O)R^{42}$, —$OS(O)_2R^{42}$, —$SR^{42}$, —$S(O)R^{42}$, —$S(O)_2R^{42}$, —$S(O)NR^{42}R^{42'}$, —$S(O)_2NR^{42}R^{42'}$, —$OS(O)NR^{42}R^{42'}$, —$OS(O)_2NR^{42}R^{42'}$, —$NR^{42}R^{42'}$, —$NR^{42}C(O)R^{43}$, —$NR^{42}C(O)OR^{43}$, —$NR^{42}C(O)NR^{43}R^{43'}$, —$NR^{42}S(O)R^{43}$, —$NR^{42}S(O)_2R^{43}$, —$NR^{42}S(O)NR^{43}R^{43'}$, —$NR^{42}S(O)_2NR^{43}R^{43'}$, —$C(O)R^{42}$, —$C(O)OR^{42}$ or —$C(O)NR^{42}R^{42'}$;

each $R^{42}$, $R^{42'}$, $R^{43}$, $R^{43'}$, $R^{44}$, $R^{44'}$, $R^{45}$, and $R^{45'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl; and u is 1, 2, 3 or 4;

wherein * is a covalent bond.

In some embodiments, L comprises a moiety of the formula selected from the group consisting of

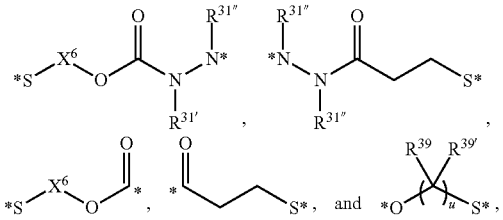

wherein each $R^{31'}$ and $R^{31''}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{32}$, $OC(O)R^{32}$, —$OC(O)NR^{32}R^{32'}$, —$OS(O)R^{32}$, —$OS(O)_2R^{32}$, —$SR^{32}$, —$S(O)R^{32}$, —$S(O)_2R^{32}$, —$S(O)NR^{32}R^{32'}$, —$S(O)_2NR^{32}R^{32'}$, —$OS(O)NR^{32}R^{32'}$, —$OS(O)_2NR^{32}R^{32'}$, —$NR^{32}R^{32'}$, —$NR^{32}C(O)R^{33}$, —$NR^{32}C(O)OR^{33}$, —$NR^{32}C(O)NR^{33}R^{33'}$, —$NR^{32}S(O)R^{33}$, —$NR^{32}S(O)_2R^{33}$, —$NR^{32}S(O)NR^{33}R^{33'}$, —$NR^{32}S(O)_2NR^{33}R^{33'}$, —$C(O)R^{32}$, —$C(O)OR^{32}$ or —$C(O)NR^{32}R^{32'}$;

each $X^6$ is independently $C_1$-$C_6$ alkyl or $C_6$-$C_{10}$ aryl($C_1$-$C_6$ alkyl), wherein each hydrogen atom in $C_1$-$C_6$ alkyl and $C_6$-$C_{10}$ aryl($C_1$-$C_6$ alkyl) is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{34}$, —$OC(O)R^{34}$, —$OC(O)NR^{34}R^{34'}$, —$OS(O)R^{34}$, —$OS(O)_2R^{34}$, —$SR^{34}$, —$S(O)R^{34}$, —$S(O)_2R^{34}$, —$S(O)NR^{34}R^{34'}$, —S(O)$_2$NR$^{34}$R$^{34'}$, —OS(O)NR$^{34}$R$^{34'}$, —OS(O)$_2$NR$^{34}$R$^{34'}$, —NR$^{34}$R$^{34'}$, —NR$^{34}$C(O)R$^{35}$, NR$^{34}$C(O)OR$^{35}$, —NR$^{34}$C(O)NR$^{35}$R$^{35'}$, —NR$^{34}$S(O)R$^{35}$, —NR$^{34}$S(O)$_2$R$^{35}$, —NR$^{34}$S(O)NR$^{35}$R$^{35'}$, —NR$^{34}$S(O)$_2$NR$^{35}$R$^{35'}$, —C(O)R$^{34}$, —C(O)OR$^{34}$ or —C(O)NR$^{34}$R$^{34'}$;

each R$^{32}$, R$^{32'}$, R$^{33}$, R$^{33'}$, R$^{34}$, R$^{34'}$, R$^{35}$ and R$^{35'}$ is independently selected from the group consisting of H, C$_1$-C$_7$ alkyl, C$_2$-C$_7$ alkenyl, C$_2$-C$_7$ alkynyl, C$_3$-C$_6$ cycloalkyl, 3- to 7-membered heterocycloalkyl, C$_6$-C$_{10}$ aryl, and 5- to 7-membered heteroaryl;

each R$^{39}$ and R$^{39'}$ is independently selected from the group consisting of H, C$_1$-C$_6$ alkyl, C$_2$-C$_6$ alkenyl, C$_2$-C$_6$ alkynyl and C$_3$-C$_6$ cycloalkyl, wherein each hydrogen atom in C$_1$-C$_6$ alkyl, C$_2$-C$_6$ alkenyl, C$_2$-C$_6$ alkynyl and C$_3$-C$_6$ cycloalkyl is independently optionally substituted by halogen, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{44}$, OC(O)R$^{44}$, —OC(O)NR$^{44}$R$^{44'}$, —OS(O)R$^{44}$, —OS(O)$_2$R$^{44}$, —SR$^{44}$, —S(O)R$^{44}$, —S(O)$_2$R$^{44}$, —S(O)NR$^{44}$R$^{44'}$, —S(O)$_2$NR$^{44}$R$^{44'}$, —OS(O)NR$^{44}$R$^{44'}$, —OS(O)$_2$NR$^{44}$R$^{44'}$, —NR$^{44}$R$^{44'}$, —NR$^{44}$C(O)R$^{45}$, —NR$^{44}$C(O)OR$^{45}$, —NR$^{44}$C(O)NR$^{45}$R$^{45'}$, —NR$^{44}$S(O)R$^{45}$, —NR$^{44}$S(O)$_2$R$^{45}$, —NR$^{44}$S(O)NR$^{45}$R$^{45'}$, —NR$^{44}$S(O)$_2$NR$^{45}$R$^{45'}$, —C(O)R$^{44}$, —C(O)OR$^{44}$ or —C(O)NR$^{44}$R$^{44'}$;

each R$^{44}$, R$^{44'}$, R$^{45}$, and R$^{45'}$ is independently selected from the group consisting of H, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl and 5- to 7-membered heteroaryl; and u is 1, 2, 3 or 4;

wherein * is a covalent bond.

In some embodiments, L comprises one or more additional linker moieties L$^2$ of the formula

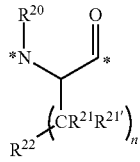

wherein

R$^{20}$ is selected from the group consisting of H, C$_1$-C$_6$ alkyl, C$_2$-C$_6$ alkenyl, C$_2$-C$_6$ alkynyl, —C(O)R$^{23}$, —C(O)OR$^{23}$ and —C(O)NR$^{23}$R$^{23'}$, wherein each hydrogen atom in C$_1$-C$_6$ alkyl, C$_2$-C$_6$ alkenyl and C$_2$-C$_6$ alkynyl is independently optionally substituted by halogen, C$_1$-C$_6$ alkyl, C$_2$-C$_6$ alkenyl, and C$_2$-C$_6$ alkynyl, —OR$^{24}$, —OC(O)R$^{24}$, —OC(O)NR$^{24}$R$^{24'}$, —OS(O)R$^{24}$, —OS(O)$_2$R$^{24}$, —SR$^{24}$, —S(O)R$^{24}$, —S(O)$_2$R$^{24}$, —S(O)NR$^{24}$R$^{24'}$, —S(O)$_2$NR$^{24}$R$^{24'}$, —OS(O)NR$^{24}$R$^{24'}$, —OS(O)$_2$NR$^{24}$R$^{24'}$, —NR$^{24}$R$^{24'}$, —NR$^{24}$C(O)R$^{25}$, —NR$^{24}$C(O)OR$^{25}$, —NR$^{24}$C(O)NR$^{25}$R$^{25'}$, —NR$^{24}$S(O)R$^{25}$, —NR$^{24}$S(O)$_2$R$^{25}$, —NR$^{24}$S(O)NR$^{25}$R$^{25'}$, —NR$^{24}$S(O)$_2$NR$^{25}$R$^{25'}$, C(O)R$^{24}$, —C(O)OR$^{24}$, or —C(O)NR$^{24}$R$^{24'}$;

each R$^{21}$ and R$^{21'}$ is independently selected from the group consisting of H, halogen, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{24}$, OC(O)R$^{24}$, —OC(O)NR$^{24}$R$^{24'}$, —OS(O)R$^{24}$, —OS(O)$_2$R$^{24}$, —SR$^{24}$, —S(O)R$^{24}$, —S(O)$_2$R$^{24}$, —S(O)NR$^{24}$R$^{24'}$, —S(O)$_2$NR$^{24}$R$^{24'}$, —OS(O)NR$^{24}$R$^{24'}$, —OS(O)$_2$NR$^{24}$R$^{24'}$, —NR$^{24}$R$^{24'}$, —NR$^{24}$C(O)R$^{25}$, —NR$^{24}$C(O)OR$^{25}$, —NR$^{24}$C(O)NR$^{25}$R$^{25'}$, —NR$^{24}$S(O)R$^{25}$, —NR$^{24}$S(O)$_2$R$^{25}$, —NR$^{24}$S(O)NR$^{25}$R$^{25'}$, —NR$^{24}$S(O)$_2$NR$^{25}$R$^{25'}$, —C(O)R$^{24}$, —C(O)OR$^{24}$ and —C(O)NR$^{24}$R$^{24'}$, wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl and 5- to 7-membered heteroaryl is independently optionally substituted by halogen, C$_1$-C$_6$ alkyl, C$_2$-C$_6$ alkenyl, C$_2$-C$_6$ alkynyl, C$_3$-C$_6$ cycloalkyl, —OR$^{24}$, —OC(O)R$^{24}$, —OC(O)NR$^{24}$R$^{24'}$, —OS(O)R$^{24}$, —OS(O)$_2$R$^{24}$, —SR$^{24}$, —S(O)R$^{24}$, —S(O)$_2$R$^{24}$, —S(O)NR$^{24}$R$^{24'}$, —S(O)$_2$NR$^{24}$R$^{24'}$, —OS(O)NR$^{24}$R$^{24'}$, —OS(O)$_2$NR$^{24}$R$^{24'}$, —NR$^{24}$R$^{24'}$, —NR$^{24}$C(O)R$^{25}$, —NR$^{24}$C(O)OR$^{25}$, —NR$^{24}$C(O)NR$^{25}$R$^{25'}$, —NR$^{24}$S(O)R$^{25}$, —NR$^{24}$S(O)$_2$R$^{25}$, —NR$^{24}$S(O)NR$^{25}$R$^{25'}$, —NR$^{24}$S(O)$_2$NR$^{25}$R$^{25'}$, —C(O)R$^{24}$, —C(O)OR$^{24}$ and —C(O)NR$^{24}$R$^{24'}$, wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl and 5- to 7-membered heteroaryl is independently optionally substituted by halogen, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{24}$, —OC(O)R$^{24}$, —OC(O)NR$^{24}$R$^{24'}$, —OS(O)R$^{24}$, —OS(O)$_2$R$^{24}$, —SR$^{24}$, —S(O)R$^{24}$, —S(O)$_2$R$^{24}$, —S(O)NR$^{24}$R$^{24'}$, —S(O)$_2$NR$^{24}$R$^{24'}$, —OS(O)NR$^{24}$R$^{24'}$, —OS(O)$_2$NR$^{24}$R$^{24'}$, —NR$^{24}$R$^{24'}$, —NR$^{24}$C(O)R$^{25}$, —NR$^{24}$C(O)OR$^{25}$, NR$^{24}$C(O)NR$^{25}$R$^{25'}$, —NR$^{24}$S(O)R$^{25}$, —NR$^{24}$S(O)$_2$R$^{25}$, —NR$^{24}$S(O)NR$^{25}$R$^{25'}$, —NR$^{24}$S(O)$_2$NR$^{25}$R$^{25'}$, —C(O)R$^{24}$, —C(O)OR$^{24}$ or —C(O)NR$^{24}$R$^{24'}$;

R$^{22}$ is selected from the group consisting of H, D, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{26}$, —OC(O)R$^{26}$, —OC(O)NR$^{26}$R$^{26'}$, —OS(O)R$^{26}$, —OS(O)$_2$R$^{26}$, —SR$^{26}$, —S(O)R$^{26}$, —S(O)$_2$R$^{26}$, —S(O)NR$^{26}$R$^{26'}$, —S(O)$_2$NR$^{26}$R$^{26'}$, —OS(O)NR$^{26}$R$^{26'}$, —OS(O)$_2$NR$^{26}$R$^{26'}$, —NR$^{26}$R$^{26'}$, —NR$^{26}$C(O)R$^{27}$, —NR$^{26}$C(O)OR$^{27}$, —NR$^{26}$C(O)NR$^{27}$R$^{27'}$, NR$^{26}$C(=NR$^{26''}$)NR$^{27}$R$^{27'}$, —NR$^{26}$S(O)R$^{27}$, —NR$^{26}$S(O)$_2$R$^{27}$, —NR$^{26}$S(O)NR$^{27}$R$^{27'}$, —NR$^{26}$S(O)$_2$NR$^{27}$R$^{27'}$, —C(O)R$^{26}$, —C(O)OR$^{26}$ and —C(O)NR$^{26}$R$^{26'}$, wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl and 5- to 7-membered heteroaryl is independently optionally substituted by halogen, C$_1$-C$_6$ alkyl, C$_2$-C$_6$ alkenyl, —(CH$_2$)$_p$OR$^{28}$, —(CH$_2$)$_p$(OCH$_2$)$_q$OR$^{28}$, —(CH$_2$)$_p$(OCH$_2$CH$_2$)$_q$OR$^{28}$, —OR$^{29}$, —OC(O)R$^{29}$, —OC(O)NR$^{29}$R$^{29'}$, —OS(O)R$^{29}$, —OS(O)$_2$R$^{29}$, —(CH$_2$)$_p$OS(O)$_2$OR$^{29}$, —OS(O)$_2$OR$^{29}$, —SR$^{29}$, —S(O)R$^{29}$, —S(O)$_2$R$^{29}$, —S(O)NR$^{29}$R$^{29'}$, —S(O)$_2$NR$^{29}$R$^{29'}$, —OS(O)NR$^{29}$R$^{29'}$, —OS(O)$_2$NR$^{29}$R$^{29'}$, —NR$^{29}$R$^{29'}$, —NR$^{29}$C(O)R$^{30}$, NR$^{29}$C(O)OR$^{30}$, —NR$^{29}$C(O)NR$^{30}$R$^{30'}$, —NR$^{29}$S(O)R$^{30}$, —NR$^{29}$S(O)$_2$R$^{30}$, —NR$^{29}$S(O)NR$^{30}$R$^{30'}$, —NR$^{29}$S(O)$_2$NR$^{30}$R$^{30'}$, —C(O)R$^{29}$, —C(O)OR$^{29}$ or —C(O)NR$^{29}$R$^{29'}$;

each R$^{24}$, R$^{24'}$, R$^{25}$, R$^{25'}$, R$^{26}$, R$^{26'}$, R$^{26''}$, R$^{29}$, R$^{29'}$, R$^{30}$ and R$^{30'}$ is independently selected from the group consisting of H, D, C$_1$-C$_7$ alkyl, C$_2$-C$_7$ alkenyl, C$_2$-C$_7$ alkynyl, C$_3$-C$_6$ cycloalkyl, 3- to 7-membered heterocycloalkyl, C$_6$-C$_{10}$ aryl and 5- to 7-membered heteroaryl, wherein each hydrogen atom in C$_1$-C$_7$ alkyl, C$_2$-C$_7$ alkenyl, C$_2$-C$_7$ alkynyl, C$_3$-C$_6$ cycloalkyl, 3- to 7-membered heterocycloalkyl, C$_6$-C$_{10}$ aryl, or 5- to 7-membered heteroaryl is independently optionally substituted by halogen, —OH, —SH, —NH$_2$ or —CO$_2$H;

R$^{27}$ and R$^{27'}$ are each independently selected from the group consisting of H, C$_1$-C$_9$ alkyl, C$_2$-C$_9$ alkenyl, C$_2$-C$_9$ alkynyl, C$_3$-C$_6$ cycloalkyl, —(CH$_2$)$_p$(sugar), —(CH$_2$)$_p$(OCH$_2$CH$_2$)$_q$-(sugar) and —(CH$_2$)$_p$(OCH$_2$CH$_2$CH$_2$)$_q$(sugar);

$R^{28}$ is H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, 5- to 7-membered heteroaryl or sugar;

n is 1, 2, 3, 4 or 5;

p is 1, 2, 3, 4 or 5;

q is 1, 2, 3, 4 or 5; and

* is a covalent bond.

In some embodiments, L comprises a moiety $L^2$ of the formula

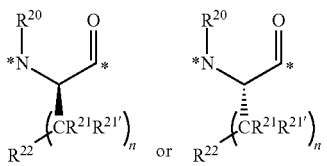

wherein $R^{20}$, $R^{21}$, $R^{21'}$, $R^{22}$ and n are as defined herein.

In some embodiments, L comprises a moiety $L^2$ of the formula

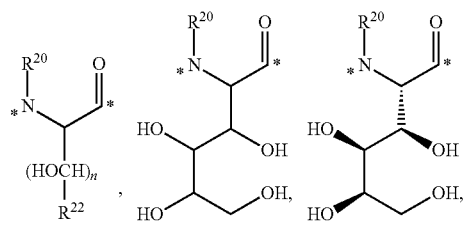

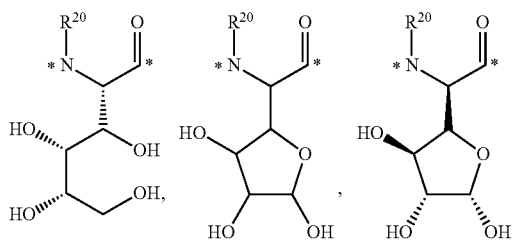

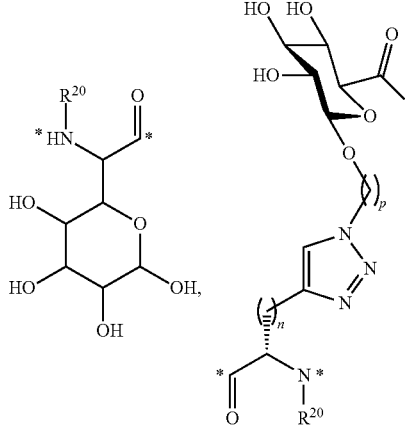

-continued

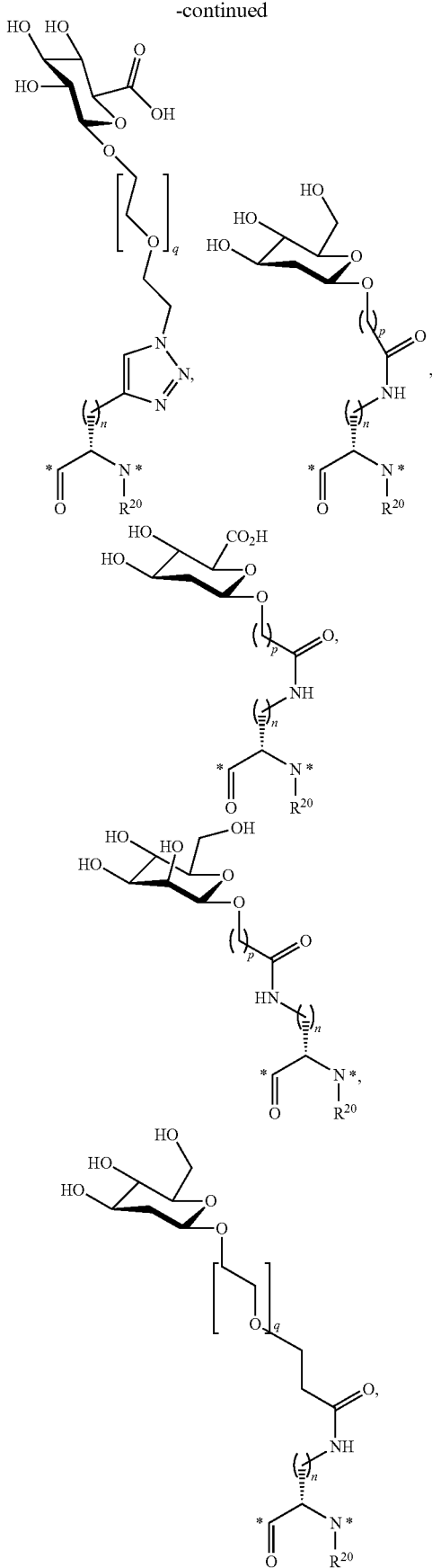

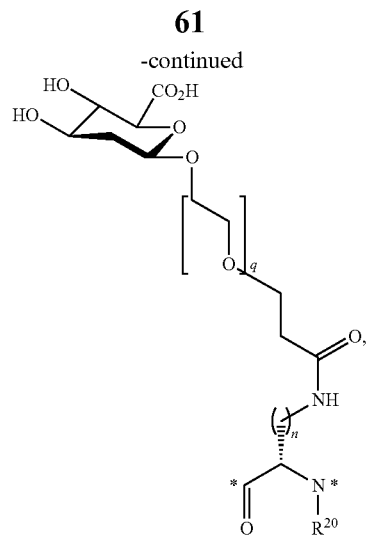

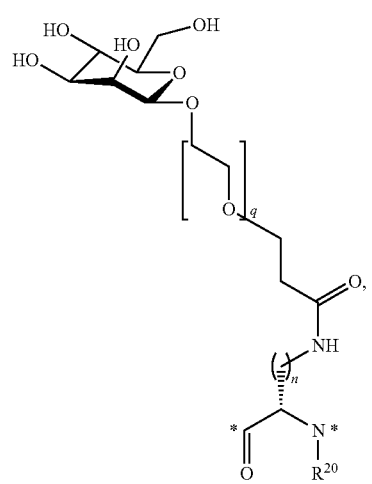

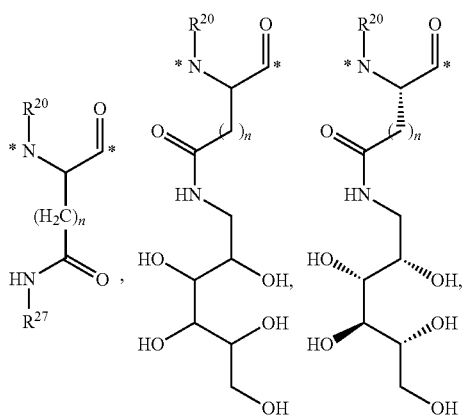

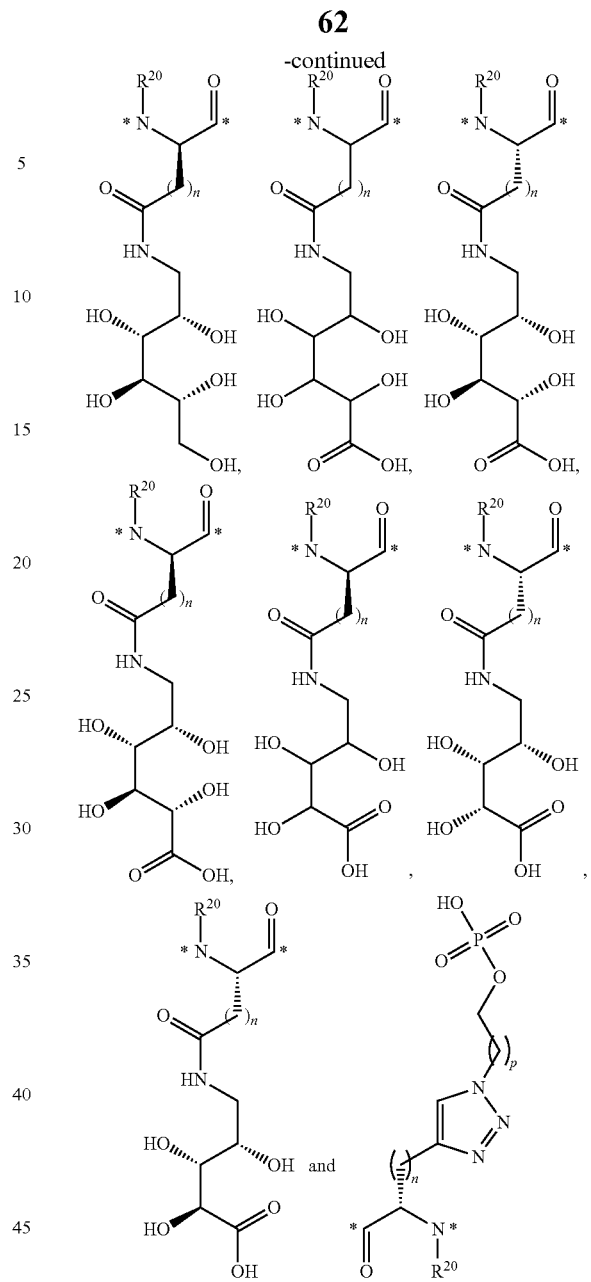

wherein $R^{20}$, $R^{27}$, n, p and q are as defined herein.

In some embodiments, L comprises additional groups such as polymers, such as polyolefins, polyethers, polyamides, copolymers, and the like, long-chain alkyl groups, peptides, and the like. In some embodiments, L comprises a polymer comprising from about 2 to about 200 monomer units. In some embodiments, L comprises a polymer comprising from about 2 to about 100 monomer units. In some embodiments, the polymer comprises from about 2 to about 20 monomer units. In some embodiments, L comprises a polyether. In some embodiments, L comprises a polyethylene glycol (PEG). In some embodiments, L comprises a polyethylene glycol (PEG) comprising from about 2 to about 200 monomer units. In some embodiments, L comprises a polyethylene glycol (PEG) comprising from about 2 to about 100 monomer units. In some embodiments, L comprises a polyethylene glycol (PEG) comprising from about 2 to about 50 monomer units. It will be appreciated that a range such as about 2 to 200, about 2 to about 100, about 2 to about 50, about 2 to about 20, and the like, contemplates all sub-ranges included therein. For example, the range about 2 to about 20, includes ranges such as 2 to 20, 2 to 15, 2 to 12, 2 to 10, 2 to 5, 3 to 20, 3 to 15, 3 to 12, 3 to 10, 3 to 5, and the like including all possible ranges. In some embodiments, L comprises a polyethylene glycol (PEG) comprising two monomer units. In some embodiments, L comprises a polyethylene glycol (PEG) comprising three monomer units. In some embodiments, L comprises a polyethylene glycol (PEG) comprising 6 monomer units. In some embodiments, L comprises a polyethylene glycol (PEG) comprising 10 monomer units. In some embodiments, L comprises a polyethylene glycol (PEG) comprising 12 monomer units.

In some embodiments, L comprises a moiety $L^3$ of the formula

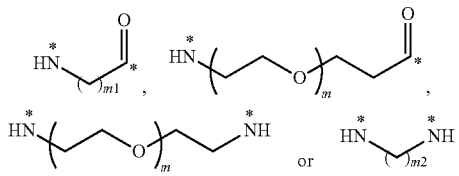

wherein m is an integer from 1 to about 50, m1 is an integer from 1 to about 30, m2 is an integer from 1 to 20, and each * represents a covalent bond to the rest of the conjugate.

In some embodiments, L comprises one or more amino acids (AA) as described herein. It will be appreciated that where L comprises one or more amino acids, the amino acids can be directly in the chain of atoms that connect D to B or ancillary to the chain of atoms that connect D to B. It will be further appreciated that where L comprises more than one amino acid, the amide bond may or may not be cleaved under physiological conditions. For example, in the case where L comprises a dipeptide directly in the chain of atoms that connect B to D, the amide bond in the dipeptide may be cleavable under physiological conditions to release B from D.

It will be further appreciated that where L comprises one or more amino acids, such amino acids can be naturally occurring amino acids of unnatural amino acids. It will be further appreciated that where L comprises one or more amino acids, such amino acids can be derivatized with one or more functional groups or protecting groups as are commonly known in the art.

In some embodiments, L further comprises one or more amino acids selected from the group consisting of lysine (Lys), asparagine (Asn), threonine (Thr), serine (Ser), isoleucine (Ile), methionine (Met), proline (Pro), histidine (His), glutamine (Gln), arginine (Arg), glycine (Gly), aspartic acid (Asp), glutamic acid (Glu), alanine (Ala), valine (Val), phenylalanine (Phe), leucine (Leu), tyrosine (Tyr), cysteine (Cys), tryptophan (Trp), phosphoserine (PSER), sulfo-cysteine, arginosuccinic acid (ASA), hydroxyproline, phosphoethanolamine (PEA), sarcosine (SARC), taurine (TAU), carnosine (CARN), citrulline (CIT), anserine (ANS), 1,3-methyl-histidine (ME-HIS), alpha-amino-adipic acid (AAA), beta-alanine (BALA), ethanolamine (ETN), gamma-amino-butyric acid (GABA), beta-amino-isobutyric acid (BAIA), alpha-amino-butyric acid (BABA), L-allo-cystathionine (cystathionine-A; CYSTA-A), L-cystathionine (cystathionine-B; CYSTA-B), cystine, allo-isoleucine (ALLO-ILE), DL-hydroxylysine (hydroxylysine (I)), DL-allo-hydroxylysine (hydroxylysine (2)), ornithine (ORN), and homocystine (HCY).

In some embodiments, L comprises one or more amino acids selected from the group consisting of L-asparagine, L-arginine, L-glycine, L-aspartic acid, L-glutamic acid, L-glutamine, L-cysteine, L-alanine, L-valine, L-leucine, L-isoleucine, 3-amino-L-alanine, D-asparagine, D-arginine, D-glycine, D-aspartic acid, D-glutamic acid, D-glutamine, D-cysteine, D-alanine, D-valine, D-leucine, D-isoleucine and 3-amino-D-alanine. In some embodiments, L comprises at least two amino acids selected from the group consisting of L-asparagine, L-arginine, L-glycine, L-aspartic acid, L-glutamic acid, L-glutamine, L-cysteine, L-alanine, L-valine, L-leucine, L-isoleucine and 3-amino-L-alanine. In some embodiments, L comprises at least two amino acids selected from the group consisting of L-asparagine, L-arginine, L-glycine, L-aspartic acid, L-glutamic acid, L-glutamine, L-cysteine, L-alanine, L-valine, L-leucine, L-isoleucine and 3-amino-L-alanine, wherein at least one amino acid is derivatized with a functional group or a protecting group as commonly known in the art.

It will be appreciated that the parts of L (e.g. $L^1$, $L^2$, $L^3$, AA, and the like) can be combined in various arrangements to provide different embodiments of the present disclosure. In some embodiments, L is of the formula -$L^3$-AA-$L^2$-AA-$L^2$-$L^1$-. In some embodiments, L is of the formula -$L^3$-AA-$L^2$-AA-$L^2$-AA-AA-$L^1$-. In some embodiments, L comprises a group of the formula AA-AA-AA-$L^3$-. In some embodiments, L comprises a group of the formula AA-AA-$L^1$-$L^3$-. In some embodiments, L comprises a group of the formula AA-AA-AA-$L^3$-. In some embodiments, L comprises a group of the formula AA-AA-$L^3$-. In some embodiments, L comprises a group of the formula AA-$L^3$-. In some embodiments, L comprises a group of the formula AA-$(L^3)_2$-. In some embodiments, L comprises a group of the formula -$L^1$-AA-AA-$L^3$-. In some embodiments, L comprises a group of the formula $L^3$. In some embodiments, L comprises a group of the formula $(L^3)_2$.

In some embodiments, L is of the formula

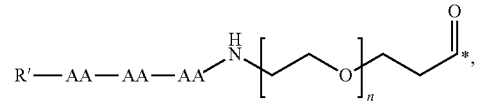

wherein AA is an amino acid, R' is selected from the group consisting of H, $C_1$-$C_6$ alkyl, and —C(O)R", R" is selected from the group consisting of H, $C_1$-$C_6$ alkyl, $C_2$-$C_6$ alkenyl, $C_2$-$C_6$ alkynyl $C_3$-$C_6$ cycloalkyl and $C_6$-$C_{10}$ aryl, n is an integer between 1 and 15, and * is a covalent bond, wherein one AA is covalently bound to B or D.

In some embodiments, L is of the formula

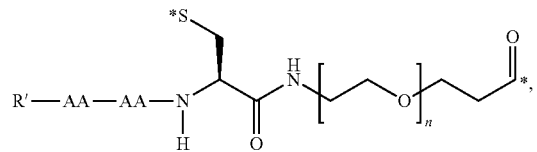

wherein AA is an amino acid, R' is selected from the group consisting of H, $C_1$-$C_6$ alkyl, and —C(O)R", R" is selected from the group consisting of H, $C_1$-$C_6$ alkyl, $C_2$-$C_6$ alkenyl, $C_2$-$C_6$ alkynyl $C_3$-$C_6$ cycloalkyl and $C_6$-$C_{10}$ aryl, n is an integer between 1 and 15, and * is a covalent bond.

In some embodiments, L is of the formula

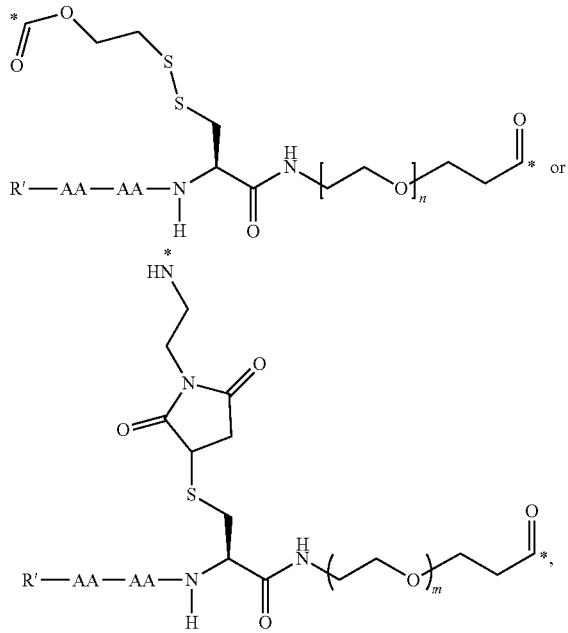

wherein AA is an amino acid, R' is selected from the group consisting of H, $C_1$-$C_6$ alkyl, and —C(O)R", R" is selected from the group consisting of H, $C_1$-$C_6$ alkyl, $C_2$-$C_6$ alkenyl, $C_2$-$C_6$ alkynyl $C_3$-$C_6$ cycloalkyl and $C_6$-$C_{10}$ aryl, n is an integer between 1 and 15, and * is a covalent bond.

In some embodiments, L is of the formula

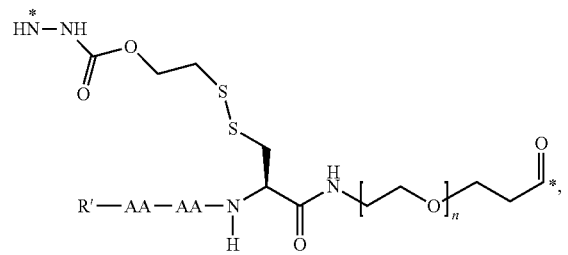

wherein AA is an amino acid, R' is selected from the group consisting of H, $C_1$-$C_6$ alkyl, and —C(O)R", R" is selected from the group consisting of H, $C_1$-$C_6$ alkyl, $C_2$-$C_6$ alkenyl, $C_2$-$C_6$ alkynyl $C_3$-$C_6$ cycloalkyl and $C_6$-$C_{10}$ aryl, n is an integer between 1 and 15, and * is a covalent bond.

In some embodiments, L is of the formula

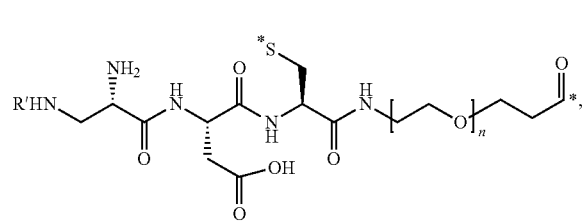

wherein R' is selected from the group consisting of H, $C_1$-$C_6$ alkyl, and —C(O)R", R" is selected from the group consisting of H, $C_1$-$C_6$ alkyl, $C_2$-$C_6$ alkenyl, $C_2$-$C_6$ alkynyl $C_3$-$C_6$ cycloalkyl and $C_6$-$C_{10}$ aryl, n is an integer between 1 and 15, and * is a covalent bond.

In some embodiments, L is of the formula

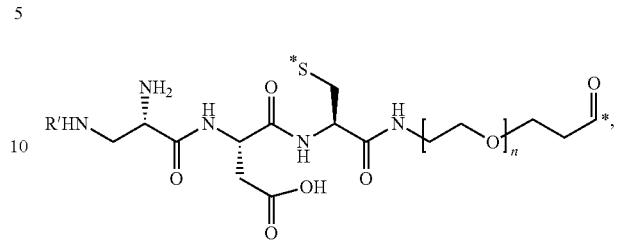

wherein R' is selected from the group consisting of H, $C_1$-$C_6$ alkyl, and —C(O)R", R" is selected from the group consisting of H, $C_1$-$C_6$ alkyl, $C_2$-$C_6$ alkenyl, $C_2$-$C_6$ alkynyl $C_3$-$C_6$ cycloalkyl and $C_6$-$C_{10}$ aryl, n is an integer between 1 and 15, and * is a covalent bond.

In some embodiments, L is of the formula

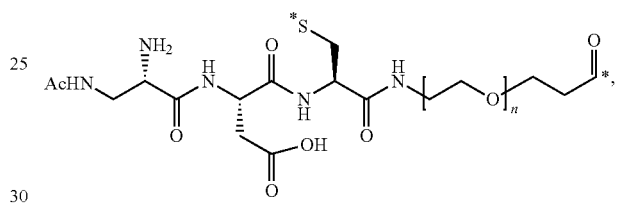

wherein n is an integer between 1 and 15, and * is a covalent bond.

In some embodiments, L is of the formula

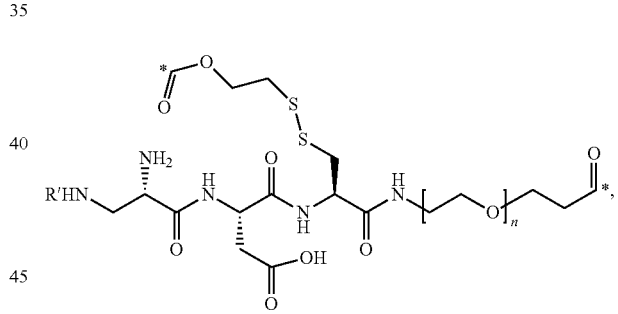

wherein R' is selected from the group consisting of H, $C_1$-$C_6$ alkyl, and —C(O)R", R" is selected from the group consisting of H, $C_1$-$C_6$ alkyl, $C_2$-$C_6$ alkenyl, $C_2$-$C_6$ alkynyl $C_3$-$C_6$ cycloalkyl and $C_6$-$C_{10}$ aryl, n is an integer between 1 and 15, and * is a covalent bond.

In some embodiments, L is of the formula

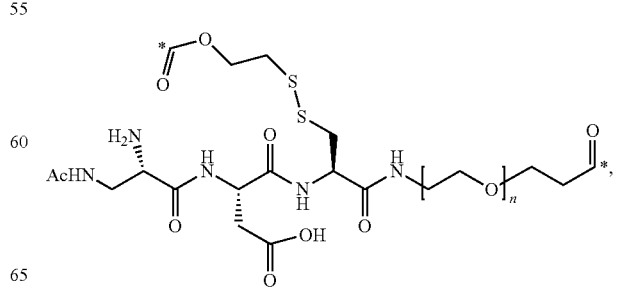

wherein n is an integer between 1 and 15, and * is a covalent bond.

In some embodiments, L is of the formula

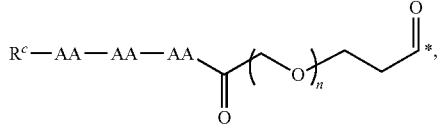

wherein $R^c$ is a functional group, selected from the group consisting of hydroxyl, $C_1$-$C_6$ alkoxy, $C_1$-$C_6$ alkyl, amino, mercapto, $C_1$-$C_6$ alkylthio, sulfinyl, sulfonyl, S-sulfonamido, N-sulfonamido, O-carbamyl, N-carbamyl, O-thiocarbamyl, and N-thiocarbamyl, n is an integer between 1 and 15, and * is a covalent bond, wherein one AA is covalently bound to B or D.

In some embodiments, L is of the formula

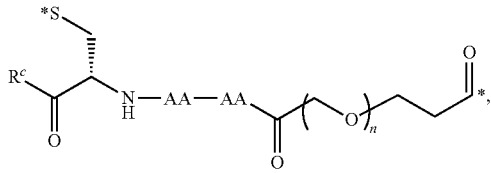

wherein $R^c$ is a functional group, selected from the group consisting of hydroxyl, $C_1$-$C_6$ alkoxy, $C_1$-$C_6$ alkyl, amino, mercapto, $C_1$-$C_6$ alkylthio, sulfinyl, sulfonyl, S-sulfonamido, N-sulfonamido, O-carbamyl, N-carbamyl, O-thiocarbamyl, and N-thiocarbamyl, n is an integer between 1 and 15, and * is a covalent bond.

In some embodiments, L is of the formula

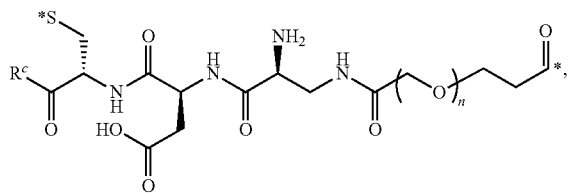

wherein $R^c$ is a functional group, selected from the group consisting of hydroxyl, $C_1$-$C_6$ alkoxy, $C_1$-$C_6$ alkyl, amino, mercapto, $C_1$-$C_6$ alkylthio, sulfinyl, sulfonyl, S-sulfonamido, N-sulfonamido, O-carbamyl, N-carbamyl, O-thiocarbamyl, and N-thiocarbamyl, n is an integer between 1 and 15, and * is a covalent bond.

In some embodiments, L is of the formula

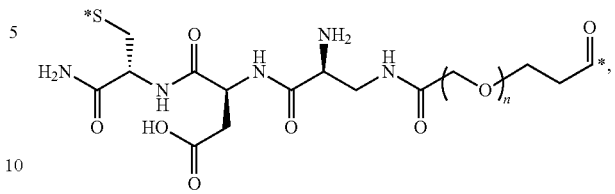

wherein n is an integer between 1 and 15, and * is a covalent bond.

In some embodiments, L is of the formula

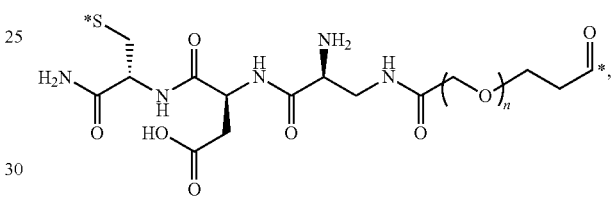

wherein n is an integer between 1 and 15, and * is a covalent bond.

In some embodiments, L is of the formula

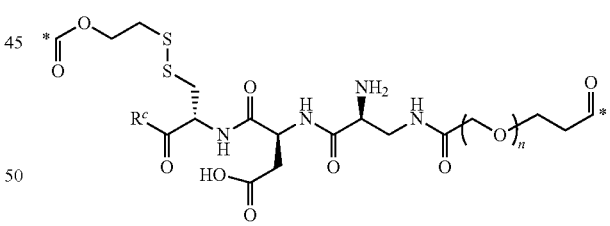

wherein $R^c$ is a functional group, selected from the group consisting of hydroxyl, $C_1$-$C_6$ alkoxy, $C_1$-$C_6$ alkyl, amino, mercapto, $C_1$-$C_6$ alkylthio, sulfinyl, sulfonyl, S-sulfonamido, N-sulfonamido, O-carbamyl, N-carbamyl, O-thiocarbamyl, and N-thiocarbamyl, n is an integer between 1 and 15, and * is a covalent bond.

In some embodiments, L is of the formula

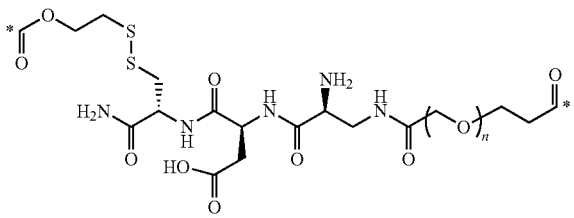

wherein n is an integer between 1 and 15, and * is a covalent bond.

The drug (also known herein as D) used in connection with any of the conjugates described herein can be any molecule capable of modulating or otherwise modifying cell function, including pharmaceutically active compounds. Suitable molecules can include, but are not limited to peptides, oligopeptides, retro-inverso oligopeptides, proteins, protein analogs in which at least one non-peptide linkage replaces a peptide linkage, apoproteins, glycoproteins, enzymes, coenzymes, enzyme inhibitors, amino acids and their derivatives, receptors and other membrane proteins; antigens and antibodies thereto; haptens and antibodies thereto; hormones, lipids, phospholipids, liposomes; toxins; antibiotics; analgesics; bronchodilators; beta-blockers; antimicrobial agents; antihypertensive agents; cardiovascular agents including antiarrhythmics, cardiac glycosides, antianginals and vasodilators; central nervous system agents including stimulants, psychotropics, antimanics, and depressants; antiviral agents; antihistamines; cancer drugs including chemotherapeutic agents; tranquilizers; anti-depressants; H-2 antagonists; anticonvulsants; antinauseants; prostaglandins and prostaglandin analogs; muscle relaxants; anti-inflammatory substances; stimulants; decongestants; antiemetics; diuretics; antispasmodics; antiasthmatics; anti-Parkinson agents; expectorants; cough suppressants; mucolytics; and mineral and nutritional additives.

Further, the D can be any drug known in the art which is cytotoxic, enhances tumor permeability, inhibits tumor cell proliferation, promotes apoptosis, decreases anti-apoptotic activity in target cells, is used to treat diseases caused by infectious agents, enhances an endogenous immune response directed to the pathogenic cells, or is useful for treating a disease state caused by any type of pathogenic cell. Drugs suitable for use in accordance with the conjugates described herein include adrenocorticoids and corticosteroids, alkylating agents, antiandrogens, antiestrogens, androgens, aclamycin and aclamycin derivatives, estrogens, antimetabolites such as cytosine arabinoside, purine analogs, pyrimidine analogs, and methotrexate, busulfan, carboplatin, chlorambucil, cisplatin and other platinum compounds, tamoxiphen, taxol, paclitaxel, paclitaxel derivatives, Taxotere®, cyclophosphamide, daunomycin, daunorubicin, doxorubicin, rhizoxin, T2 toxin, plant alkaloids, prednisone, hydroxyurea, teniposide, mitomycins, discodermolides, microtubule inhibitors, epothilones, tubulysin, cyclopropyl benz[e]indolone, seco-cyclopropyl benz[e]indolone, O—Ac-seco-cyclopropyl benz[e]indolone, bleomycin and any other antibiotic, nitrogen mustards, nitrosureas, vincristine, vinblastine, analogs and derivative thereof such as deacetylvinblastine monohydrazide, and other vinca alkaloids, including those described in PCT international publication No. WO 2007/022493, the disclosure of which is incorporated herein by reference, colchicine, colchicine derivatives, allocolchicine, thiocolchicine, trityl cysteine, Halicondrin B, dolastatins such as dolastatin 10, amanitins such as α-amanitin, camptothecin, irinotecan, and other camptothecin derivatives thereof, maytansines, geldanamycin and geldanamycin derivatives, estramustine, nocodazole, MAP4, colcemid, inflammatory and proinflammatory agents, peptide and peptidomimetic signal transduction inhibitors, and any other art-recognized drug or toxin. Other drugs that can be used as D in conjugates described herein include penicillins, cephalosporins, vancomycin, erythromycin, clindamycin, rifampin, chloramphenicol, aminoglycoside antibiotics, gentamicin, amphotericin B, acyclovir, trifluridine, ganciclovir, zidovudine, amantadine, ribavirin, and any other art-recognized antimicrobial compound.

In other embodiments, the D is a drug selected from the group consisting of a vinca alkaloid, such as DAVLBH, a cryptophycin, bortezomib, thiobortezomib, a tubulysin, aminopterin, rapamycin, paclitaxel, docetaxel, doxorubicin, daunorubicin, everolimus, α-amanatin, verucarin, didemnin B, geldanamycin, purvalanol A, ispinesib, budesonide, dasatinib, an epothilone, a maytansine, and a tyrosine kinase inhibitor, including analogs and derivatives of the foregoing.

In some embodiments, D can be a tubulysin. Tubulysins are a class of cytostatic tetrapeptides originally isolated from several strains of myxobacteria, noteworthy for their picomolar cytotoxicity against mammalian cells and nanomolar cytotoxicity in multidrug resistant cell lines. Natural tubulysins are generally linear tetrapeptides consisting of N-methyl pipecolic acid (Mep), isoleucine (Ile), an unnatural amino acid called tubuvaline (Tuv), and either an unnatural amino acid called tubutyrosine (Tut, an analog of tyrosine) or an unnatural amino acid called tubuphenylalanine (Tup, an analog of phenylalanine).

In some embodiments, D is a tetrapeptide of the formula I

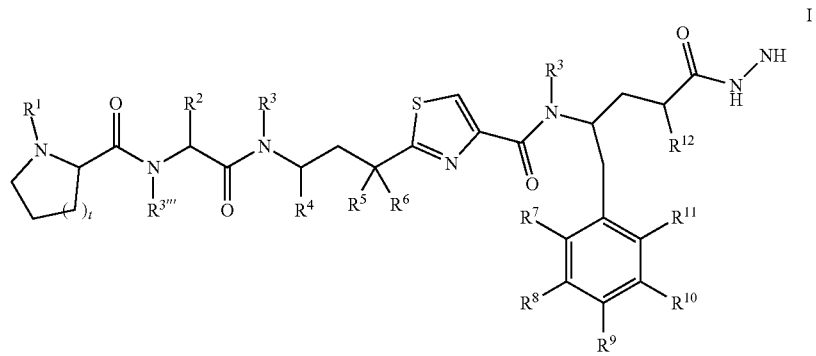

wherein $R^1$, $R^3$, $R^{3'}$ and $R^{3'''}$ are each independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{13}$, —$OC(O)R^{13}$, —OC(O)$NR^{13}R^{13'}$, —$OS(O)R^{13}$, —$OS(O)_2R^{13}$, —$SR^{13}$, —SC(O)$R^{13}$, —$S(O)R^{13}$, —$S(O)_2R^{13}$, —$S(O)_2OR^{13}$, —S(O)$NR^{13}R^{13'}$, —$S(O)_2NR^{13}R^{13'}$, —OS(O)$NR^{13}R^{13'}$, —$OS(O)_2NR^{13}R^{13'}$, —$NR^{13}R^{13'}$, —N $R^{13}C(O)R^{14}$, —$NR^{13}C(O)OR^{14}$, —$NR^{13}C(O)NR^{14}R^{14'}$, —$NR^{13}S(O)R^{14}$, —$NR^{13}S(O)_2R^{14}$, —$NR^{13}S(O)NR^{13}R^{14'}$, —$NR^{13}S(O)_2NR^{14}R^{14'}$, —$P(O)(OR^{13})_2$, —$C(O)R^{13}$, —$C(O)OR^{13}$, or —C(O)$NR^{13}R^{13'}$;

$R^2$, $R^4$ and $R^{12}$ are each independently selected from the group consisting of H, $C_1$-$C_6$ alkyl, $C_2$-$C_6$ alkenyl, $C_2$-$C_6$ alkynyl;

$R^5$ and $R^6$ are each independently selected from the group consisting of H, halogen, $C_1$-$C_6$ alkyl, $C_2$-$C_6$ alkenyl, $C_2$-$C_6$ alkynyl, —$OR^{15}$, —$SR^{15}$, —$OC(O)R^{15}$, —OC(O)$NR^{15}R^{15'}$, and —$NR^{15}R^{15'}$, wherein each hydrogen atom in $C_1$-$C_6$ alkyl, $C_2$-$C_6$ alkenyl and $C_2$-$C_6$ alkynyl is independently optionally substituted by halogen, —$OR^{16}$, —$SR^{16}$, —$NR^{16}R^{16'}$, C(O)$R^{16}$, —C(O)$OR^{16}$ or —C(O)$NR^{16}R^{16'}$; or $R^5$ and $R^6$ taken together with the carbon atom to which they are attached form a —C(O)—;

each $R^7$, $R^8$, $R^9$, $R^{10}$ and $R^{11}$ is independently selected from the group consisting of H, halogen, $C_1$-$C_6$ alkyl, $C_2$-$C_6$ alkenyl, $C_2$-$C_6$ alkynyl, —CN, —$NO_2$, —NCO, —$OR^{17}$, —$SR^{17}$, —$S(O)_2OR^{17}$, —$NR^{17}R^{17'}$, —$P(O)(OR^{17})_2$, —$C(O)R^{17}$, —$C(O)OR^{17}$ and —C(O)$NR^{17}R^{17'}$, wherein each hydrogen atom in $C_1$-$C_6$ alkyl, $C_2$-$C_6$ alkenyl and $C_2$-$C_6$ alkynyl is independently optionally substituted by halogen, —$OR^{18}$, —$SR^{18}$, —$NR^{18}R^{18'}$, —$C(O)R^{18}$, —C(O)$OR^{18}$ or —C(O)$NR^{18}R^{18'}$;

each $R^{13}$, $R^{13'}$, $R^{14}$, $R^{14'}$, $R^{15}$, $R^{15'}$, $R^{16}$, $R^{16'}$, $R^{17}$ and $R^{17'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by halogen, —OH, —SH, —$NH_2$ or —$CO_2H$;

each $R^{18}$ and $R^{18'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl —$C(O)R^{19}$, —$P(O)(OR^{19})_2$, and —$S(O)_2OR^{19}$;

each $R^{19}$ is independently selected from H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl; and t is 1, 2 or 3, wherein * is a covalent bond.

In some embodiments, D is a tetrapeptide of the formula

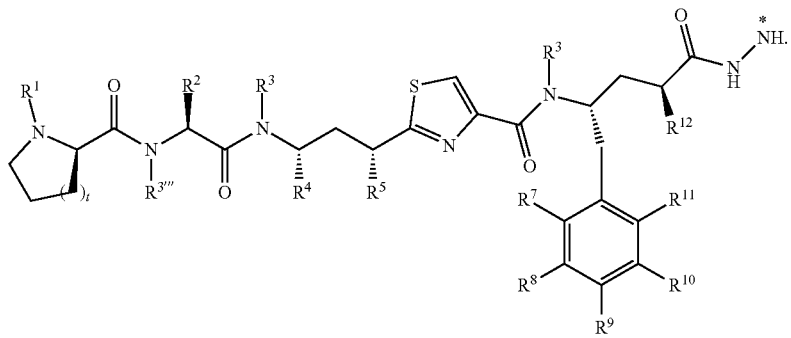

wherein $R^1$, $R^2$, $R^3$, $R^{3'}$, $R^{3''}$, $R^4$, $R^5$, $R^7$, $R^8$, $R^9$, $R^{10}$, $R^{11}$, $R^{12}$ and t are as defined herein, and * is a covalent bond.

In some embodiments, D is a tetrapeptide of the formula

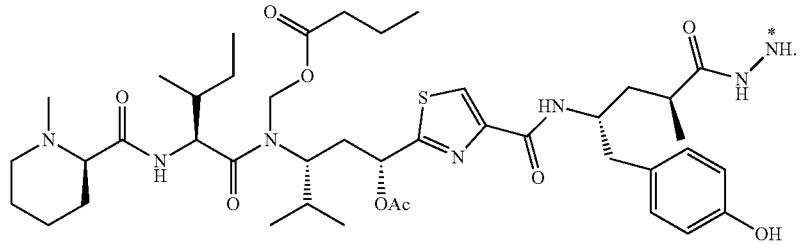

wherein * is a covalent bond.

In some embodiments, D is a tetrapeptide of the formula I

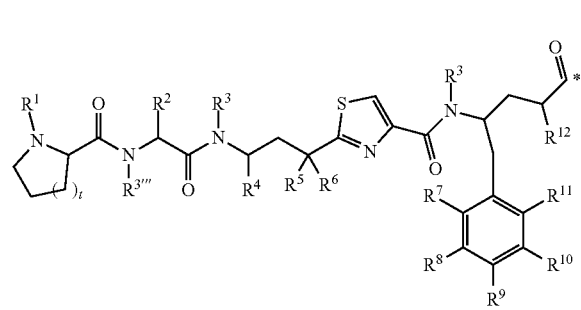

wherein $R^1$, $R^3$, $R^{3'}$ and $R^{3'''}$ are each independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{13}$, —$OC(O)R^{13}$, —$OC(O)NR^{13}R^{13'}$, —$OS(O)R^{13}$, —$OS(O)_2R^{13}$, —$SR^{13}$, —$SC(O)R^{13}$, —$S(O)R^{13}$, —$S(O)_2R^{13}$, —$S(O)_2OR^{13}$, —$S(O)NR^{13}R^{13'}$, —$S(O)_2NR^{13}R^{13'}$, —$OS(O)NR^{13}R^{13'}$, —$OS(O)_2NR^{13}R^{13'}$, —$NR^{13}R^{13'}$, —$NR^{13}C(O)R^{14}$, —$NR^{13}C(O)OR^{14}$, —$NR^{13}C(O)NR^{14}R^{14'}$, —$NR^{13}S(O)R^{14}$, —$NR^{13}S(O)_2R^{14}$, —$NR^{13}S(O)NR^{13}R^{14'}$, —$NR^{13}S(O)_2NR^{14}R^{14'}$, —$P(O)(OR^{13})_2$, —$C(O)R^{13}$, —$C(O)OR^{13}$ or —$C(O)NR^{13}R^{13'}$;

$R^2$, $R^4$ and $R^{12}$ are each independently selected from the group consisting of H, $C_1$-$C_6$ alkyl, $C_2$-$C_6$ alkenyl, $C_2$-$C_6$ alkynyl;

$R^5$ and $R^6$ are each independently selected from the group consisting of H, halogen, $C_1$-$C_6$ alkyl, $C_2$-$C_6$ alkenyl, $C_2$-$C_6$ alkynyl, —$OR^{15}$, —$SR^{15}$, —$OC(O)R^{15}$, —$OC(O)NR^{15}R^{15'}$, and —$NR^{15}R^{15'}$, wherein each hydrogen atom in $C_1$-$C_6$ alkyl, $C_2$-$C_6$ alkenyl and $C_2$-$C_6$ alkynyl is independently optionally substituted by halogen, —$OR^{16}$, —$SR^{16}$, —$NR^{16}R^{16'}$, $C(O)R^{16}$, —$C(O)OR^{16}$ or —$C(O)NR^{16}R^{16'}$; or $R^5$ and $R^6$ taken together with the carbon atom to which they are attached form a —$C(O)$—;

each $R^7$, $R^8$, $R^9$, $R^{10}$ and $R^{11}$ is independently selected from the group consisting of H, halogen, $C_1$-$C_6$ alkyl, $C_2$-$C_6$ alkenyl, $C_2$-$C_6$ alkynyl, —CN, —$NO_2$, —NCO, —$OR^{17}$, —$SR^{17}$, —$S(O)_2OR^{17}$, —$NR^{17}R^{17'}$, —$P(O)(OR^{17})_2$, —$C(O)R^{17}$, —$C(O)OR^{17}$ and —$C(O)NR^{17}R^{17'}$, wherein each hydrogen atom in $C_1$-$C_6$ alkyl, $C_2$-$C_6$ alkenyl and $C_2$-$C_6$ alkynyl is independently optionally substituted by halogen, —$OR^{18}$, —$SR^{18}$, —$NR^{18}R^{18'}$, —$C(O)R^{18}$, —$C(O)OR^{18}$ or —$C(O)NR^{18}R^{18'}$;

each $R^{13}$, $R^{13'}$, $R^{14}$, $R^{14'}$, $R^{15}$, $R^{15'}$, $R^{16}$, $R^{16'}$, $R^{17}$ and $R^{17'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by halogen, —OH, —SH, —$NH_2$ or —$CO_2H$;

each $R^{18}$ and $R^{18'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl —$C(O)R^{19}$, —$P(O)(OR^{19})_2$, and —$S(O)_2OR^{19}$;

each $R^{19}$ is independently selected from H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl; and t is 1, 2 or 3, wherein * is a covalent bond.

In some embodiments, D is a tetrapeptide of the formula

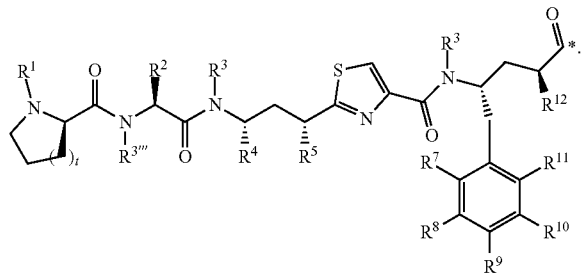

wherein $R^1$, $R^2$, $R^3$, $R^{3'}$, $R^{3''}$, $R^4$, $R^5$, $R^7$, $R^8$, $R^9$, $R^{10}$, $R^{11}$, $R^{12}$ and t are as defined herein, and * is a covalent bond.

In some embodiments, D is a tetrapeptide of the formula

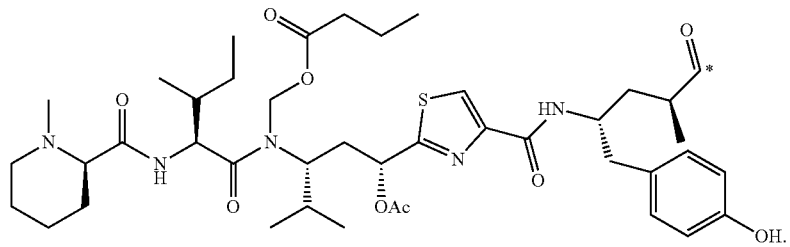

wherein * is a covalent bond.

The imaging agent (also referred to herein as I) can be any molecule capable of providing a measurable signal for imaging or visualized cells or tissues. Suitable molecules useful as imaging agents include, but are not limited to, dyes, such as rhodamine dyes and fluorescein dyes, PET imaging agents, or radiolabeled agents, and the like. Examples of rhodamine dyes include, but are not limited to, 5-carboxytetramethylrhodamine (5-TAMRA), rhodamine B, rhodamine 6G, TRITC, Texas Red, rhodamine 123, sulforhodamine 101, and the like. Examples of fluorescein dyes include but are not limited to fluorescein, 5-amino-fluorescein, 6-amino-fluorescein, fluorescein isocyanate (FITC), NHS-fluorescein, Oregon Green, Tokyo Green, Singapore Green, Philadelphia Green, and the like. It will be appreciated that upon conjugation to a linker as described herein to provide a conjugate of the disclosure, the functional group at the point of covalent attachment to the linker may be transformed into a new functional group. For example, one of skill in the art will appreciate that conjugation of FITC to provide a FITC conjugate of the invention can involve attachment of a linker to the isothiocyanate functional group through an amine containing linker, the isothiocyanate group is transformed into a thiourea functional group.

In some embodiments, the present disclosure provides methods for imaging a population of cell or tissue, either in vitro or in vivo. It will be appreciated that such in vitro methods can be carried out by any method known in the art. In some embodiments, in vitro imaging methods described herein can include a. contacting a population of cells with a conjugate as described herein that is suitable for imaging to provide the conjugate bound to cells expressing a CCK2R protein, and b. visualizing the conjugate bound to cells by irradiation with light. It will be appreciated that visualizing the conjugate bound to cells by irradiation with light can include irradiation at an excitation wavelength and detection at an emission wavelength. Thus, in some embodiments, in vitro imaging methods described herein can include a. contacting a population of cells with a conjugate as described herein that is suitable for imaging to provide the conjugate bound to cells expressing a CCK2R protein, b. irradiating the conjugate bound to cells expressing a CCK2R protein with an excitation wavelength light, and c. detecting light emitted from the cancer cells at an emission wavelength.

In some embodiments, tissues, such as cancerous tumors, can be imaged according to the methods described herein. For example, in some embodiments, in vivo imaging methods described herein can include a. administering to the patient a conjugate as described herein that is suitable for imaging; or a pharmaceutically acceptable salt thereof, to provide the conjugate bound to cells expressing a CCK2R protein; and b. visualizing the conjugate bound to cells expressing a CCK2R protein by irradiation with light. It will be appreciated that visualizing the conjugate bound to cells by irradiation with light can include irradiation at an excitation wavelength and detection at an emission wavelength. Thus, in some embodiments, in vivo imaging methods described herein can include a. administering to the patient a conjugate as described herein that is suitable for imaging; or a pharmaceutically acceptable salt thereof, to provide the conjugate bound to cells expressing a CCK2R protein; b. irradiating the conjugate bound to cells expressing a CCK2R protein with an excitation wavelength light; and c. detecting light emitted from the cancer cells at an emission wavelength. It will be appreciated that visualizing the conjugate bound to cells by irradiation with light can be carried out using any known imaging techniques (diagnostic or otherwise) or instrumentation known in the art.

The conjugates described herein can be used for both human clinical medicine and veterinary applications. Thus, the host animal harboring the population of pathogenic cells and treated with the conjugates described herein can be human or, in the case of veterinary applications, can be a laboratory, agricultural, domestic, or wild animal. The conjugates described herein can be applied to host animals including, but not limited to, humans, laboratory animals such rodents (e.g., mice, rats, hamsters, etc.), rabbits, monkeys, chimpanzees, domestic animals such as dogs, cats, and rabbits, agricultural animals such as cows, horses, pigs, sheep, goats, and wild animals in captivity such as bears, pandas, lions, tigers, leopards, elephants, zebras, giraffes, gorillas, dolphins, and whales.

The conjugate, compositions, methods, and uses described herein are useful for treating diseases caused at least in part by populations of pathogenic cells, which may cause a variety of pathologies in host animals. As used herein, the term "pathogenic cells" or "population of pathogenic cells" generally refers to cancer cells, infectious agents such as bacteria and viruses, bacteria- or virus-infected cells, inflammatory cells, activated macrophages capable of causing a disease state, and any other type of pathogenic cells that uniquely express, preferentially express, or overexpress cell surface receptors or cell surface antigens that may be bound by or targeted by the conjugates described herein. Pathogenic cells can also include any cells causing a disease state for which treatment with the conjugates described herein results in reduction of the symptoms of the disease. For example, the pathogenic cells can be host cells that are pathogenic under some circumstances such as cells of the immune system that are responsible for graft versus host disease, but not pathogenic under other circumstances. Thus, the population of pathogenic cells can be a cancer cell population that is tumorigenic, including benign tumors and malignant tumors, or it can be non-tumorigenic. The cancer cell population can arise spontaneously or by such processes as mutations present in the germline of the host animal or somatic mutations, or it can be chemically-, virally-, or radiation-induced. The conjugates described herein can be utilized to treat such cancers as adenocarcinomas, carcinomas, sarcomas, lymphomas, Hodgekin's disease, melanomas, mesotheliomas, Burkitt's lymphoma, nasopharyngeal carcinomas, leukemias, and myelomas. In some embodiments, conjugates described herein can be used in the treatment of cancers including, but not limited to, lung cancer, small cell lung cancer (SCLC), non-small cell lung cancer (NSCLC), bronchopulmonary carcinoid, bone cancer, pancreatic cancer, pancreatic ductal adenocarcinomas, skin cancer, cancer of the head or neck, cutaneous or intraocular melanoma, uterine cancer, ovarian cancer, rectal cancer, cancer of the anal region, stomach cancer, colon cancer, colorectal cancer, colorectal ductal adenocarcinomas, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, gastrointestinal cancer, insulinoma, ileal carcinoid, gastrointestinal stromal tumor (GIST), gastric ductal adenocarcinoma, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, cholangiocellular carcinoma, hepatocellular carcinoma, renal cell carcinoma, carcinoma of the renal pelvis, neoplasms of the central nervous system (CNS), primary CNS lymphoma, spinal axis tumors, brain stem glioma and pituitary adenoma. The cancer cell population can include, but is not limited to, oral, thyroid, endocrine, skin, gastric, esophageal, laryngeal, pancreatic, colon, bladder, bone, ovarian, cervical, uterine, breast, testicular, prostate, rectal, kidney, liver, and lung cancers. The conjugates described herein can be utilized to treat cancers including, but not limited to, gastrointestinal cancer, including insulinoma, ileal carcinoid, gastrointestinal stromal tumor (GIST), gastric ductal adenocarcinoma, colorectal ductal adenocarcinoma, pancreatic ductal adenocarcinoma, cholangiocellular carcinoma, and hepatocellular carcinoma, and lung cancer, including small cell lung cancer (SCLC), non-small cell lung cancer (NSCLC) and bronchopulmonary carcinoid.

The disclosure includes all pharmaceutically acceptable isotopically-labelled conjugates, and their Drug(s) incorporated therein, wherein one or more atoms are replaced by atoms having the same atomic number, but an atomic mass or mass number different from the atomic mass or mass number which predominates in nature.

Examples of isotopes suitable for inclusion in the conjugates, and their Drug(s) incorporated therein, include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$.

Certain isotopically-labelled conjugates, and their Drug(s) incorporated therein, for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, and $^{13}N$, can be useful in Positron Emission Topography (PET) studies for examining substrate receptor occupancy. Isotopically-labeled conjugates, and their Drug(s) incorporated therein, can generally be prepared by conventional techniques known to those skilled in the art or by processes analogous to those described in the accompanying Examples using an appropriate isotopically-labeled reagents in place of the non-labeled reagent previously employed.

The conjugates and compositions described herein may be administered orally. Oral administration may involve swallowing, so that the conjugate or composition enters the gastrointestinal tract, or buccal or sublingual administration may be employed by which the conjugate or composition enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The conjugates and compositions described herein may also be used in fast-dissolving, fast-disintegrating dosage forms such as those described in Expert Opinion in Therapeutic Patents, 11 (6), 981-986, by Liang and Chen (2001). For tablet dosage forms, depending on dose, the conjugate may make up from 1 weight % to 80 weight % of the dosage form, more typically from 5 weight % to 60 weight % of the dosage form. In addition to the conjugates and compositions described herein, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colorants, flavoring agents, preservatives and taste-masking agents. Exemplary tablets contain up to about 80% drug, from about 10 weight % to 25 about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tableting. The final formulation may comprise one or more layers and may be coated or uncoated; it may even be encapsulated. The formulation of tablets is discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a conjugate as described herein, a film-forming polymer, a binder, a solvent, a humectant, a plasticizer, a stabilizer or emulsifier, a viscosity-modifying agent and a solvent. Some components of the formulation may perform more than one function.

Solid formulations for oral administration may be formulated to be immediate and/or modified release. Modified release formulations include delayed-, sustained-, pulsed-, controlled-, targeted and programmed release. Suitable modified release formulations for the purposes of the disclosure are described in U.S. Pat. No. 6,106,864. Details of other suitable release technologies such as high energy dispersions and osmotic and coated particles are to be found in Pharmaceutical Technology On-line, 25(2), 1-14, by Verma et al (2001). The use of chewing gum to achieve controlled release is described in WO 00/35298.

The conjugates described herein can also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous.

Suitable devices for parenteral administration include needle (including micro-needle) injectors, needle-free injectors and infusion techniques. Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art. The solubility of conjugates described herein used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus conjugates described herein can be formulated as a solid, semi-solid, or thixotropic liquid for administration as an implanted depot providing modified release of the active compound. Examples of such formulations include drug-coated stents and poly(lactic-coglycolic)acid (PGLA) microspheres. The conjugates described herein can also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated— see, for example, J. Pharm Sci, 88 (10), 955-958 by Finnin and Morgan (October 1999). Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release. The conjugates described herein can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin. The pressurized container, pump, spray, atomizer, or nebulizer contains a solution or suspension of the conjugates(s) of the present disclosure comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid. Prior to use in a dry powder or suspension formulation, the conjugate is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying. Capsules (made, for example, from gelatin or hydroxypropylmethylcellulose), blisters and cartridges for use in an inhaler or insufflator may be formulated to contain a powder mix of the conjugate described herein, a suitable powder base such as lactose or starch and a performance modifier such as Iso-leucine, mannitol, or magnesium stearate.

The lactose may be anhydrous or in the form of the monohydrate, preferably the latter. Other suitable excipients include dextran, glucose, maltose, sorbitol, xylitol, fructose, sucrose and trehalose. A typical formulation may comprise a conjugate of the present disclosure, propylene glycol, sterile water, ethanol and sodium chloride. Alternative solvents which may be used instead of propylene glycol include glycerol and polyethylene glycol.

The conjugates described here can be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in International Patent Applications Nos. WO 91/11172, WO 94/02518 and WO 98/55148.

Inasmuch as it may desirable to administer a combination of active compounds, for example, for the purpose of treating a particular disease or condition, it is within the scope of the present disclosure that two or more pharmaceutical compositions, at least one of which contains a conjugate as described herein, may conveniently be combined in the form of a kit suitable for co-administration of the compositions. Thus the kit of the present disclosure comprises two or more separate pharmaceutical compositions, at least one of which contains a conjugate as described herein, and means for separately retaining said compositions, such as a container, divided bottle, or divided foil packet. An example of such a kit is the familiar blister pack used for the packaging of tablets, capsules and the like. The kit of the present disclosure is particularly suitable for administering different dosage forms, for example parenteral, for administering the separate compositions at different dosage intervals, or for titrating the separate compositions against one another. To assist compliance, the kit typically comprises directions for administration and may be provided with a so-called memory aid.

EXAMPLES

Chemistry Examples

Example 1: Synthesis of Fmoc-Asp(O$^t$Bu)-Tyr($^t$Bu)-Met-Gly-Trp(Boc)-Met-Asp(O$^t$Bu)-Phe-Resin (Protected CCK8-Resin) (1)

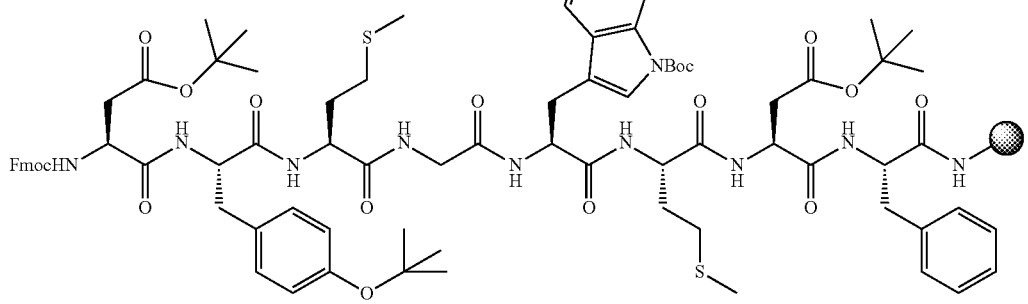

Fmoc-Sieber-resin (1.0 g, 0.69 mmol) was placed in a peptide synthesis vessel, and washed with DMF (3×10 mL). Initial Fmoc deprotection was performed using 20% piperidine in DMF (3×10 mL) solution for 10 mins per cycle. The resin was further washed with DMF (3×10 mL) and i-PrOH (3×10 mL), and a Kaiser test was conducted to determine that the reaction was complete. The resin was washed again with DMF wash (3×10 mL), and a solution of Fmoc-Phe-OH (0.57 g, 1.38 mmol, 2.0 eq.) in DMF, PyBOP (0.72 g, 1.38 mmol, 2.0 eq.) and DIPEA (0.37 mL, 2.07 mmol, 3.0 eq.) were added to the vessel. The resulting solution was bubbled with Argon for 1 hour. The coupling solution was filtered, the resin was washed with DMF (3×10 mL) and i-PrOH (3×10 mL), and a Kaiser test was conducted to determine that the reaction was complete. The process was repeated for each additional coupling according to the reagent amounts listed in Table 1.

TABLE 1

| Compound (All Compounds in this column are commercially available) | mmol | Equivalent | Molecular Weight | Quantity (grams) |
|---|---|---|---|---|
| Fmoc-Sieber-Resin (Loading ~0.69 mmol/g) | 0.69 | 1 | | 1.00 |
| Fmoc-Phe-OH | 1.38 | 2 | 387 | 0.53 |
| Fmoc-Asp(O$^t$Bu)—OH | 1.38 | 2 | 411.5 | 0.57 |
| Fmoc-Met-OH | 1.38 | 2 | 371.5 | 0.51 |
| Fmoc-Trp(Boc)-OH | 1.38 | 2 | 526.6 | 0.73 |
| Fmoc-Gly-OH | 1.38 | 2 | 297 | 0.41 |
| Fmoc-Met-OH | 1.38 | 2 | 371.5 | 0.51 |
| Fmoc-Tyr($^t$Bu)—OH | 1.38 | 2 | 459.5 | 0.63 |
| Fmoc-Asp(O$^t$Bu)—OH | 1.38 | 2 | 411.5 | 0.57 |
| PyBOP | 1.38 | 2 | 520.31 | 0.72 |
| i-Pr$_2$Net | 2.07 | 3 | 129.24 (d = 0.742) | 0.27 |

Example 2: Synthesis of Dap(Ac)-Asp-Cys-PEG$_2$-Asp-Tyr-Met-Gly-Trp-Met-Asp-Phe-NH$_2$ (2)

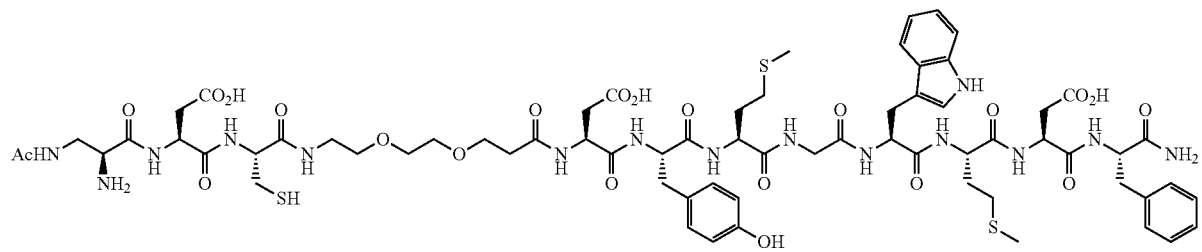

EC 1825

C$_{68}$H$_{93}$N$_{15}$O$_{22}$S$_3$
Exact Mass: 1567.58
Mol. Wt.: 1568.75

Resin bound-protected CCK8 peptide, 1, (0.8 g, 0.28 mmol) was placed in a peptide synthesis vessel, and was subjected to solid phase synthesis as described in Example 1 for the coupling of Fmoc-AEEP-OH (Fmoc-9-amino-4,7-dioxanonanoic acid), Fmoc-Cys(Trt)-OH, Fmoc-Asp(O$^t$Bu)-OH, Boc-Dap(Fmoc)-OH (N$_\alpha$-Boc-N$_\beta$-Fmoc-L-2,3-diaminopropionic acid) and Ac$_2$O using to the reagent amounts shown in Table 2. Resin cleavage was performed with a cocktail of 94% CF$_3$CO$_2$H, 2.5% EDT, 2.0% triisopropylsilane and 1.5% H$_2$O. The cleavage cocktail (10 mL) was poured onto the resin and bubbled with Argon for 30 mins, followed by filtration into a clean flask. Further cleavage was performed two times with fresh cleavage cocktail and 10 mins of Argon bubbling. The combined filtrate was poured onto cold diethyl ether, and the precipitate that formed was collected by centrifugation at 4000 rpm for 5 mins (3×). The precipitate was obtained following decanting and drying of the solid under vacuum; the product was then purified by preparative HPLC (mobile phase A=10 mM Ammonium acetate, pH=5; Organic phase B=Acetonitrile; Method; 10% B to 100% B in 30 mins) to yield EC1825 (2) (30 mg, 7%).

$^1$H NMR (500 MHz DMSO-d$_6$) Pivotal signals: δ 7.49 (d, J=7.9 Hz, 1H), 7.31 (d, J=8.1 Hz, 1H), 7.23-7.14 (m, 5H), 7.13 (s, 1H), 7.03 (t, J=7.6 Hz, 1H), 6.96-6.89 (m, 2H), 6.60 (d, J=8.4 Hz, 2H), 4.50 (dt, J=9.1, 6.6 Hz, 2H), 4.42-4.33 (m, 2H), 4.28 (td, J=9.8, 8.8, 4.7 Hz, 2H), 4.23 (dd, J=8.7, 5.2 Hz, 2H), 4.17 (dd, J=9.0, 5.0 Hz, 1H), 1.95 (s, 3H), 1.95 (s, 3H), 1.82 (s, 3H).

[M+H]$^+$=Calculated 1567.6, found 1569.3.

TABLE 2

| Compound (All Compounds in this column are commercially available) | mmol | Equivalent | Molecular Weight | Quantity (grams) |
|---|---|---|---|---|
| Protected-CCK8-Sieber-Resin (Loading ~0.35 mmol/g) | 0.28 | 1 | | 0.80 |
| Fmoc-AEEP-OH | 0.56 | 2 | 399.4 | 0.22 |
| Fmoc-Cys(Trt)-OH | 0.56 | 2 | 585.7 | 0.33 |
| Fmoc-Asp(O$^t$Bu)—OH | 0.56 | 2 | 411.5 | 0.23 |
| Boc-Dap(Fmoc)—OH | 0.56 | 2 | 426.48 | 0.24 |
| PyBOP | 0.56 | 2 | 520.31 | 0.29 |
| i-Pr$_2$Net | 0.84 | 3 | 129.24 (d = 0.742) | 0.11 |
| Ac$_2$O | 11.2 | 40 | 102.09 (d = 1.08) | 1.14 |
| i-Pr$_2$Net | 11.2 | 40 | 129.24 (d = 0.742) | 1.45 |

Example 3: Synthesis of Dap(Ac)-Asp-Cys-PEG$_3$-Asp-Tyr-Met-Gly-Trp-Met-Asp-Phe-NH$_2$ (3)

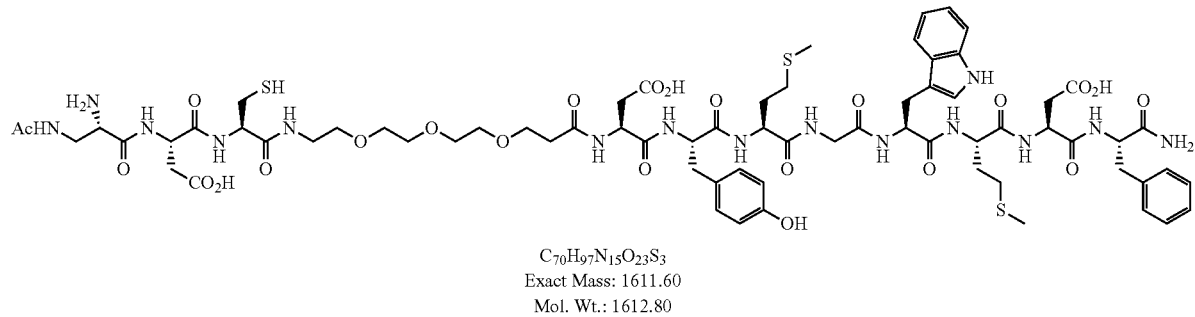

EC 1850

$C_{70}H_{97}N_{15}O_{23}S_3$
Exact Mass: 1611.60
Mol. Wt.: 1612.80

The general procedure described in Example 2 was followed for the coupling of Fmoc-NH-PEG$_3$-CH$_2$CH$_2$COOH, Fmoc-Cys(Trt)-OH, Fmoc-Asp(O$^t$Bu)-OH, Boc-Dap(Fmoc)-OH and Ac$_2$O to resin bound-protected CCK8 peptide, 1, except that Fmoc-NH-PEG$_3$-CH$_2$CH$_2$COOH was substituted for Fmoc-AEEP-OH. Resin cleavage and purification were performed as described in Example 2 to yield desired peptide EC1850 (3) (53 mg, 9.5%).

$^1$H NMR (500 MHz DMSO-d$_6$) Pivotal signals: δ 7.49 (d, J=7.9 Hz, 1H), 7.31 (d, J=8.1 Hz, 1H), 7.24-7.13 (m, 5H), 7.13 (s, 1H), 7.03 (t, J=7.5 Hz, 1H), 6.94 (d, J=8.7 Hz, 2H), 6.91 (d, J=7.5 Hz, 1H), 6.60 (d, J=8.4 Hz, 2H), 4.50 (dt, J=9.1, 6.6 Hz, 2H), 4.42-4.34 (m, 2H), 4.28 (td, J=9.8, 8.8, 4.7 Hz, 2H), 4.23 (dd, J=8.8, 5.2 Hz, 2H), 4.17 (dd, J=9.0, 5.0 Hz, 1H), 1.95 (s, 3H), 1.95 (s, 3H).

[M+H]$^+$=Calculated 1612.8, found 1613.41.

Example 4: Synthesis of Dap(Ac)-Asp-Cys-PEG$_{12}$-Asp-Tyr-Met-Gly-Trp-Met-Asp-Phe-NH$_2$ (4)

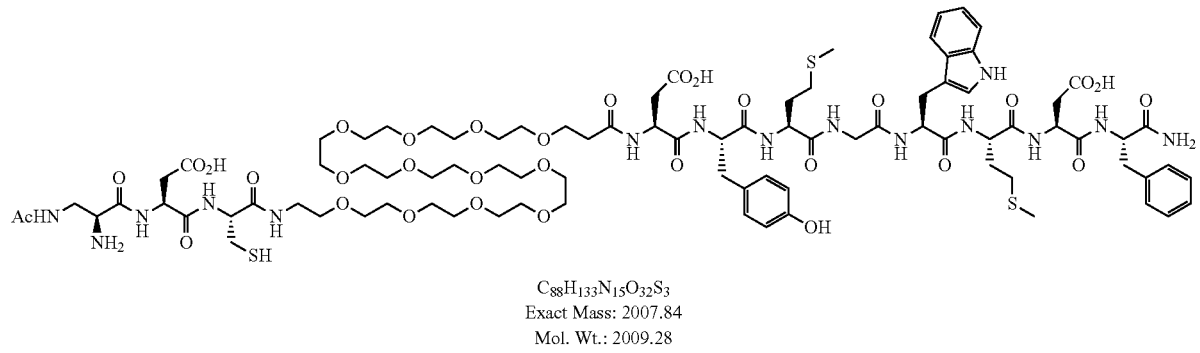

EC 1872

$C_{88}H_{133}N_{15}O_{32}S_3$
Exact Mass: 2007.84
Mol. Wt.: 2009.28

The general procedure described in Example 2 was followed was followed for the coupling of Fmoc-NH-PEG$_{12}$-CH$_2$CH$_2$COOH, Fmoc-Cys(Trt)-OH, Fmoc-Asp(O$^t$Bu)-OH, Boc-Dap(Fmoc)-OH and Ac$_2$O to resin bound-protected CCK8 peptide, 1, except that Fmoc-NH-PEG$_{12}$-CH$_2$CH$_2$COOH was substituted for Fmoc-AEEP-OH. Resin cleavage and purification were performed as described in Example 2 to yield desired peptide EC1872 (4) (50 mg, 9%).

$^1$H NMR (500 MHz DMSO-d$_6$) Pivotal signals: δ 7.49 (d, J=7.9 Hz, 1H), 7.31 (d, J=8.1 Hz, 1H), 7.23-7.14 (m, 5H), 7.13 (s, 1H), 7.03 (t, J=7.6 Hz, 1H), 6.96-6.89 (m, 2H), 6.60 (d, J=8.4 Hz, 2H), 4.50 (dt, J=9.1, 6.6 Hz, 2H), 4.42-4.33 (m, 2H), 4.28 (td, J=9.8, 8.8, 4.7 Hz, 2H), 4.23 (dd, J=8.7, 5.2 Hz, 2H), 4.17 (dd, J=9.0, 5.0 Hz, 1H), 1.95 (s, 3H), 1.95 (s, 3H), 1.82 (s, 3H).

([M+2H]$^+$)/2=Calculated 1004.9, found 1005.9.

Example 5: Synthesis of Boc-Dap-Asp-Cys-NH$_2$ (5)

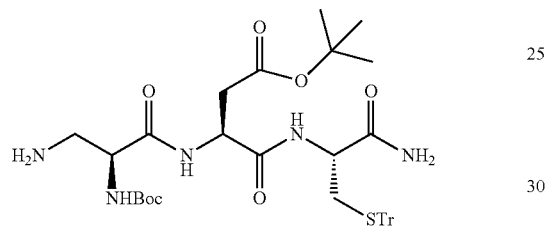

Fmoc-Sieber-resin (2.0 g, 1.38 mmol) was placed in a peptide synthesis vessel, and standard solid phase synthesis steps were performed as described in Example 1 for the coupling of Fmoc-Cys(Trt)-OH, Fmoc-Asp(O$^t$Bu)-OH, and Boc-Dap(Fmoc)-OH according to the reagents listed in Table 3. The final Fmoc deprotection was performed using 20% piperidine in DMF (3×10 mL) solution for 10 mins per cycle. The resin was washed with DMF (3×10 mL) and i-PrOH (3×10 mL), and a Kaiser test was conducted to determine that the reaction was complete. The resin was bubbled with Argon in a cleavage cocktail of 2% CF$_3$CO$_2$H in dichloromethane (3×10 mL) for 10 mins per cycle, followed by filtration and removal of solvent under vacuum to yield crude tripeptide (5) (0.685 g, 69%).

[M+H]$^+$=Calculated 719.34, found 720.71.

TABLE 3

| Compound (All Compounds in this column are commercially available) | mmol | Equivalent | Molecular Weight | Quantity (grams) |
|---|---|---|---|---|
| Fmoc-Sieber-Resin (Loading ~0.69 mmol/g) | 1.38 | 1 | | 2.00 |
| Fmoc-Cys(Trt)-OH | 2.76 | 2 | 585.7 | 1.62 |
| Fmoc-Asp(O$^t$Bu)—OH | 2.76 | 2 | 411.5 | 1.14 |
| Boc-Dap(Fmoc)—OH | 2.76 | 2 | 426.48 | 1.18 |
| PyBOP | 2.76 | 2 | 520.31 | 1.43 |
| i-Pr$_2$NEt | 4.14 | 3 | 129.24 (d = 0.742) | 0.54 |

Example 6: Synthesis of Cys-Asp-βDap-PEG$_4$-Asp-Tyr-Met-Gly-Trp-Met-Asp-Phe-NH$_2$ (6)

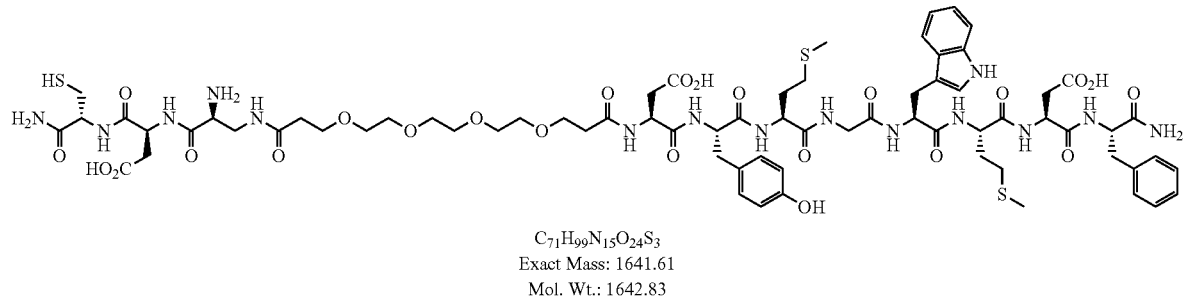

EC 1981

$C_{71}H_{99}N_{15}O_{24}S_3$
Exact Mass: 1641.61
Mol. Wt.: 1642.83

The general procedure described in Example 2 was followed for the coupling of HOOC-PEG$_3$-COOH and tripeptide (5) to resin bound-protected CCK8 peptide, 1, except 2 equivalents of HOOC-PEG$_3$-COOH and tripeptide (5) were used instead of Fmoc-AEEP-OH, Fmoc-Cys(Trt)-OH, Fmoc-Asp(O$^t$Bu)-OH, Boc-Dap(Fmoc)-OH and Ac$_2$O. Resin cleavage and purification were performed as described in Example 2 to yield desired peptide EC1981 (6) (20 mg, 3%).

[M+H]$^+$=Calculated 1641.6, found 1643.

Example 7: Synthesis of Dap(Ac)-Asp-Cys-PEG$_2$-Asp-Tyr(SO$_3^-$)-Met-Gly-Trp-Met-Asp-Phe-NH$_2$ (7)

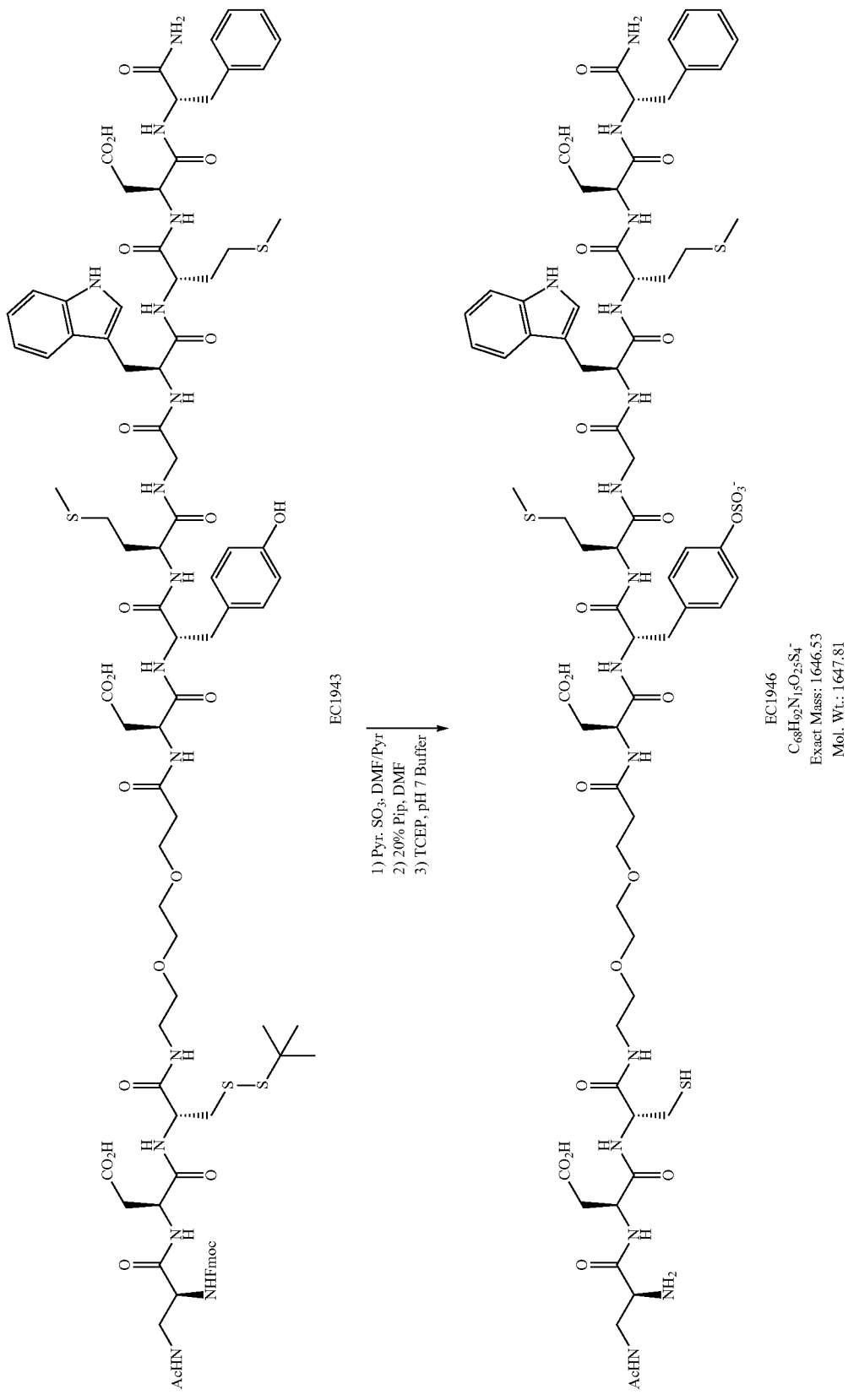

Step 1: The general procedure described in Example 2 was followed for the coupling of Fmoc-AEEP-OH, Fmoc-Cys(S$^t$Bu)-OH, Fmoc-Asp(O$^t$Bu)-OH, and Fmoc-Dap(Ac)—OH to protected CCK8-Resin, 1. Resin cleavage and deprotection were performed under cleavage and purification conditions described in Example 2 to yield partially protected peptide, EC1943.

Step 2: In a dry flask, EC1943 (125 mg, 0.067 mmol, 1.0 eq.) was dissolved in a 1:1 solution of pyridine:DMF and placed under Argon. A large excess of Pyr SO$_3$ (40 eq) was added to the solution and stirred at room temperature overnight. The reaction was quenched by the addition of water and was purified by preparative HPLC (mobile phase A=50 mM Ammonium Bicarbonate, pH=7; Organic phase B=Acetonitrile; Method; 10% B to 100% B in 30 mins) to yield sulfated product (70 mg, 54%) that was carried to the next step without further purification.

Step 3: The sulfated product of step 2 (55 mg, 0.028 mmol) was dissolved in using 20% piperidine in DMF, and stirred for an hour. Upon completion of Fmoc deprotection, the DMF solution was diluted with and excess of H$_2$O, and the desired amine product was purified using preparative HPLC (pH 7 buffer).

Step 4: The fractions containing the desired amine product of step 3 were combined, and the organic solvent was removed under reduced pressure. TCEP (5 eq) was added to the remaining buffer solution and stirred for 30 mins, and monitored for disulfide cleavage. Upon completion, the reaction mixture was purified using preparative HPLC (mobile phase A=50 mM Ammonium Bicarbonate, pH=7; Organic phase B=Acetonitrile; Method; 10% B to 100% B in 30 mins) to yield EC1946 (7) (40 mg, 86%).

$^1$H NMR (500 MHz DMSO-d$_6$) Pivotal signals: δ 7.47 (d, J=7.8 Hz, 1H), 7.29 (d, J=8.1 Hz, 1H), 7.22-7.15 (m, 4H), 7.14-7.09 (m, 2H), 7.06 (d, J=8.3 Hz, 2H), 7.04-6.96 (m, 3H), 6.91 (t, J=7.5 Hz, 1H), 4.46 (t, J=6.7 Hz, 1H), 4.44-4.40 (m, 1H), 4.38 (dd, J=8.7, 5.1 Hz, 1H), 4.31 (t, J=6.8 Hz, 1H), 4.28-4.19 (m, 3H), 1.93 (s, 3H), 1.93 (s, 3H), 1.80 (s, 3H).

[M+H]$^+$=Calculated 1647.5, found 1648.

Example 8: Synthesis of EC1826 (8)

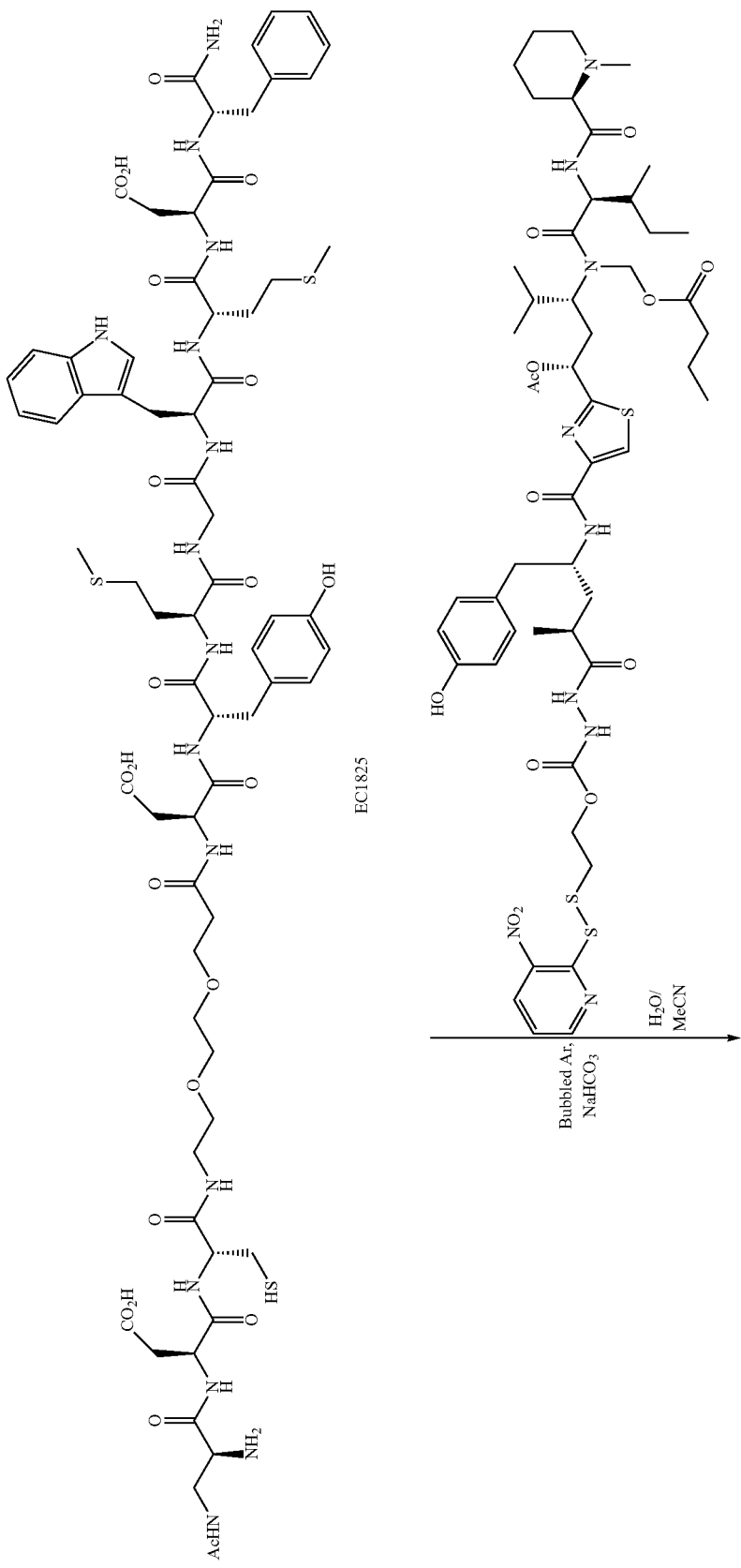

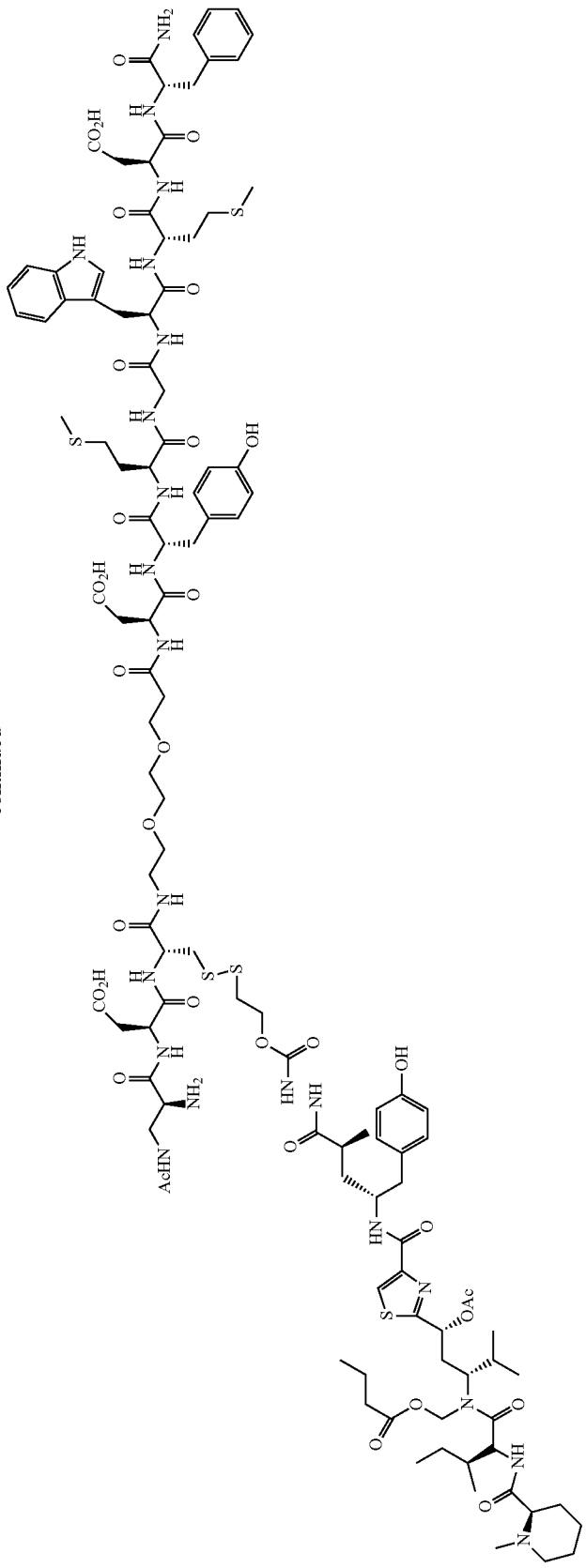
EC1826

Peptide (2) (8 mg, 5.1 µmol) was dissolved in 2 mL of deionized H₂O, and sparged with Argon. A solution of EC1428* (5.6 mg, 5.1 µmol) in 2 mL acetonitrile was added to the sparging solution, and the pH was adjusted to 7 using a saturated NaHCO₃ solution. Upon completion the reaction mixture was diluted with deionized H₂O and 10% acetonitrile in H₂O, and purified by preparative HPLC (mobile phase A=50 mM Ammonium Bicarbonate, pH=7; Organic phase B=Acetonitrile; Method; 10% B to 100% B in 30 mins) to yield EC1826 (8) (3.2 mg, 25%)

$^1$H NMR (500 MHz DMSO-$d_6$) Pivotal signals: δ 8.09 (s, 1H), 7.47 (d, J=7.9 Hz, 1H), 7.30 (d, J=8.1 Hz, 1H), 7.24-7.15 (m, 4H), 7.15-7.08 (m, 2H), 7.02 (t, J=7.6 Hz, 1H), 6.93 (td, J=13.9, 12.9, 7.6 Hz, 5H), 6.60 (d, J=8.5 Hz, 2H), 6.57 (d, J=8.2 Hz, 2H), 6.15 (s, 1H), 5.67 (d, J=11.5 Hz, 1H), 5.21 (d, J=12.0 Hz, 1H), 2.06 (s, 3H), 1.92 (s, 3H), 1.91 (s, 3H), 1.80 (s, 3H).

([M+2H]⁺)/2=Calculated 1257.5, found 1258.2.

*EC1428 was prepared according to following scheme and the procedures set forth in US20140107316, incorporated herein by reference for those portions related to the preparation of EC1428.

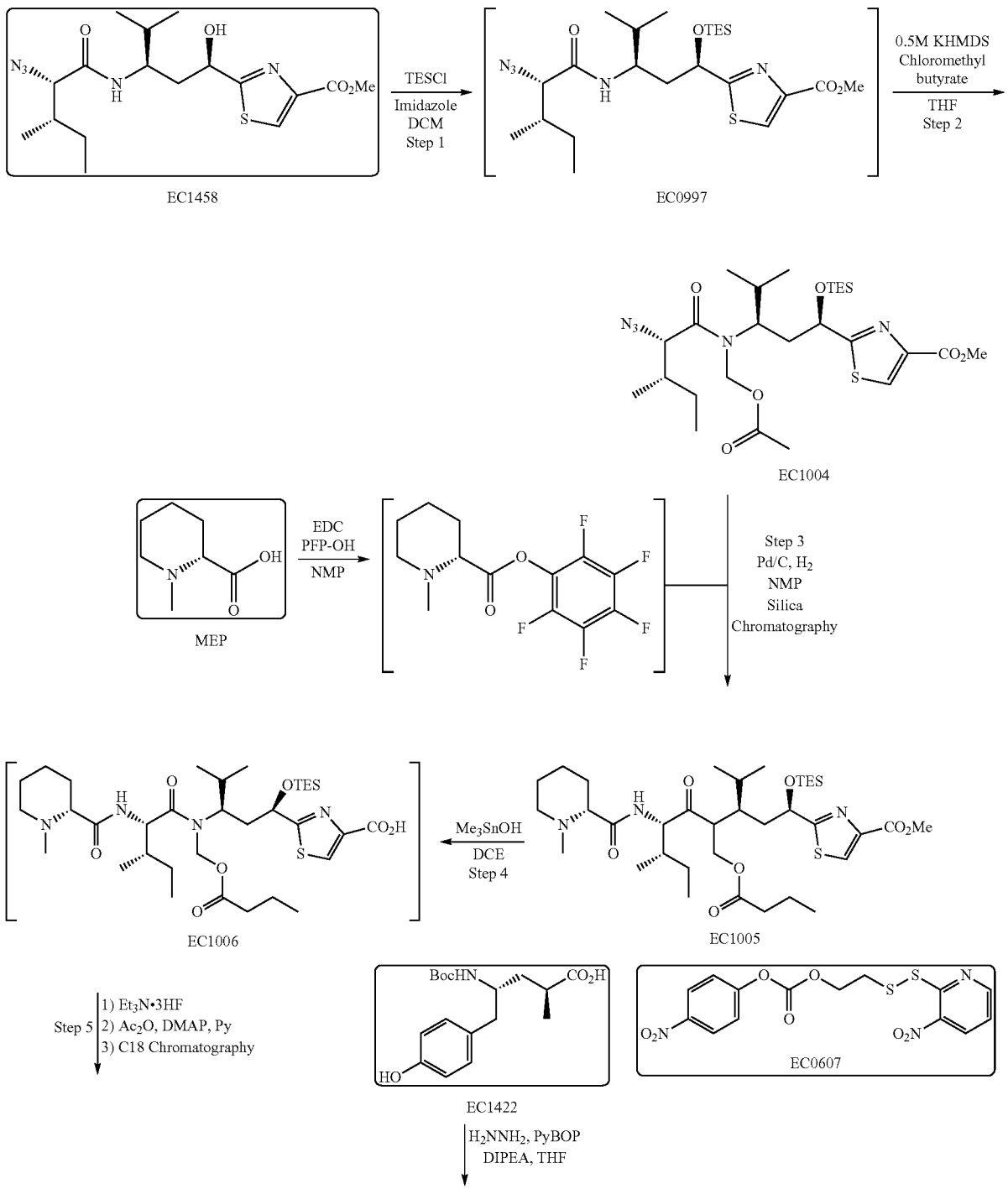

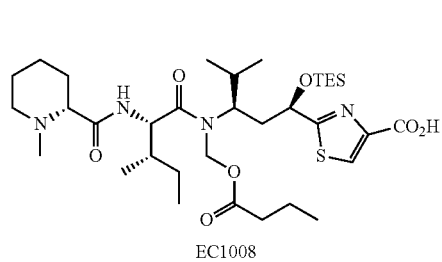
EC1008
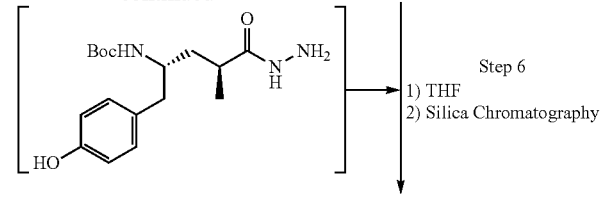
-continued
Step 6
1) THF
2) Silica Chromatography
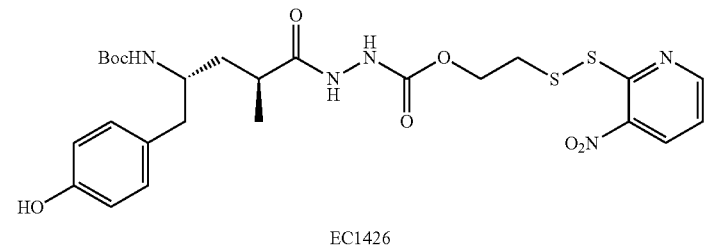
EC1426
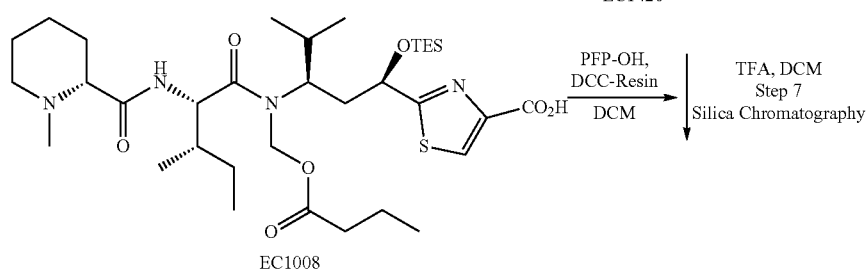
EC1008
PFP-OH, DCC-Resin
DCM
TFA, DCM
Step 7
Silica Chromatography
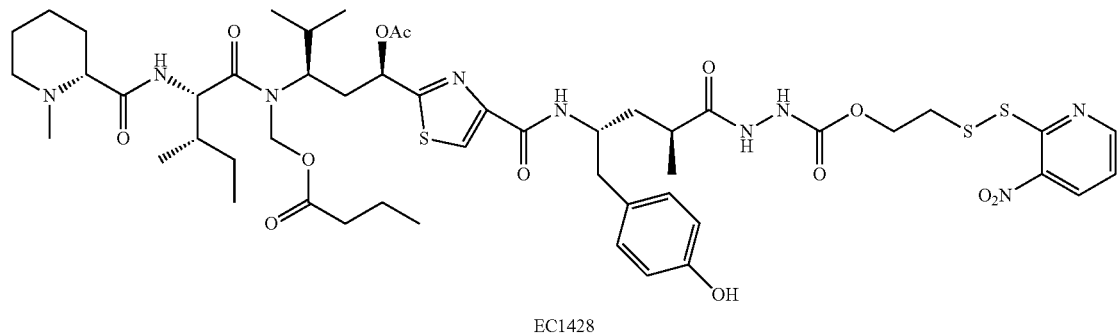
EC1428
EC0607 was prepared according to the methods described in WO2013/149185, incorporated herein by reference for those portions of the disclosure that relate to the preparation of EC0607.
Example 9: Synthesis of EC1868 (9)

EC 1868
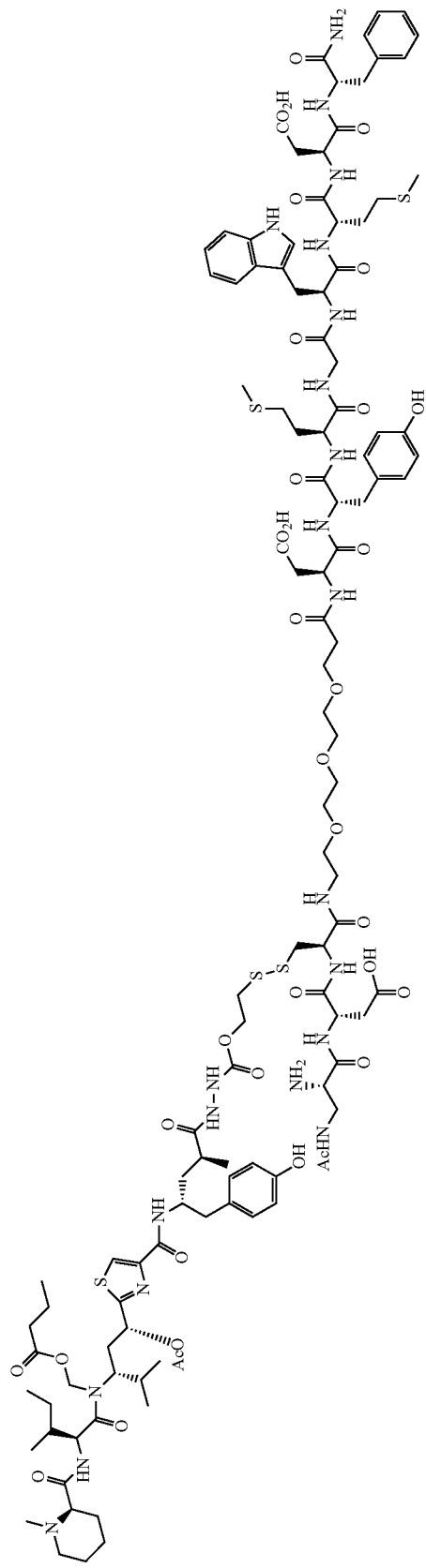
$C_{115}H_{164}N_{22}O_{34}S_5$
Exact Mass: 2557.04
Mol. Wt.: 2558.99

EC1868 was synthesized according to the procedure described in Example 8 for the synthesis and purification of EC1826 (8) in 16% yield.

$^1$H NMR (500 MHz DMSO-d$_6$) Pivotal signals: δ 8.11 (s, 1H), 7.48 (d, J=7.9 Hz, 1H), 7.31 (d, J=8.1 Hz, 1H), 7.20 (d, J=6.0 Hz, 4H), 7.16-7.09 (m, 2H), 7.03 (t, J=7.6 Hz, 1H), 6.99-6.86 (m, 5H), 6.60 (d, J=8.4 Hz, 2H), 6.58 (d, J=8.3 Hz, 2H), 6.16 (s, 1H), 5.68 (d, J=11.3 Hz, 1H), 5.22 (d, J=12.0 Hz, 1H), 2.07 (s, 3H), 2.02 (s, 3H), 1.93 (s, 3H), 1.92 (s, 3H).

([M+2H]$^+$)/2=Calculated 1279.5, found 1280.5.

Example 10: Synthesis of EC1873 (10)

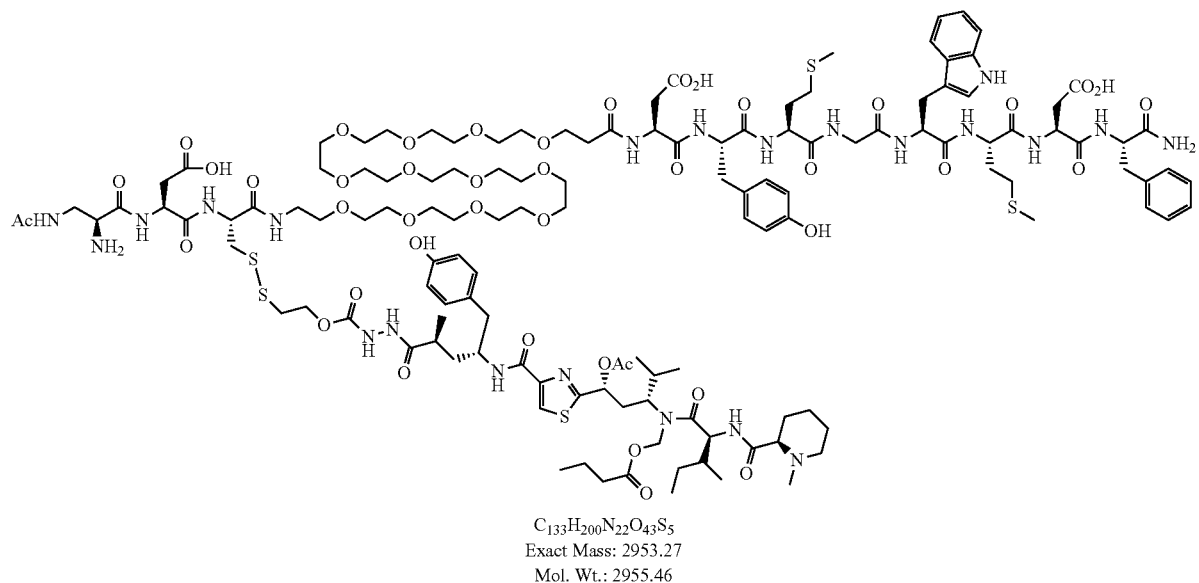

EC 1873

$C_{133}H_{200}N_{22}O_{43}S_5$
Exact Mass: 2953.27
Mol. Wt.: 2955.46

EC1873 was synthesized according to the procedure described in Example 8 for the synthesis and purification of EC1826 (8) in 16% yield.

$^1$H NMR (500 MHz DMSO-d$_6$) Pivotal signals: δ 8.08 (s, 1H), 7.46 (d, J=8.0 Hz, 1H), 7.30 (d, J=8.1 Hz, 1H), 7.23-7.15 (m, 4H), 7.15-7.11 (m, 1H), 7.11 (s, 1H), 7.05-7.00 (m, 1H), 6.99-6.89 (m, 5H), 6.60 (d, J=8.5 Hz, 2H), 6.57 (d, J=8.2 Hz, 2H), 6.15 (s, 1H), 5.67 (d, J=11.3 Hz, 1H), 5.21 (d, J=12.0 Hz, 1H), 2.06 (s, 3H), 1.98 (s, 3H), 1.91 (s, 6H), 1.67 (s, 3H).

([M+2H]$^+$)/2=Calculated 1478.2, found 1479.2.

Example 11: Synthesis of EC1947 (11)

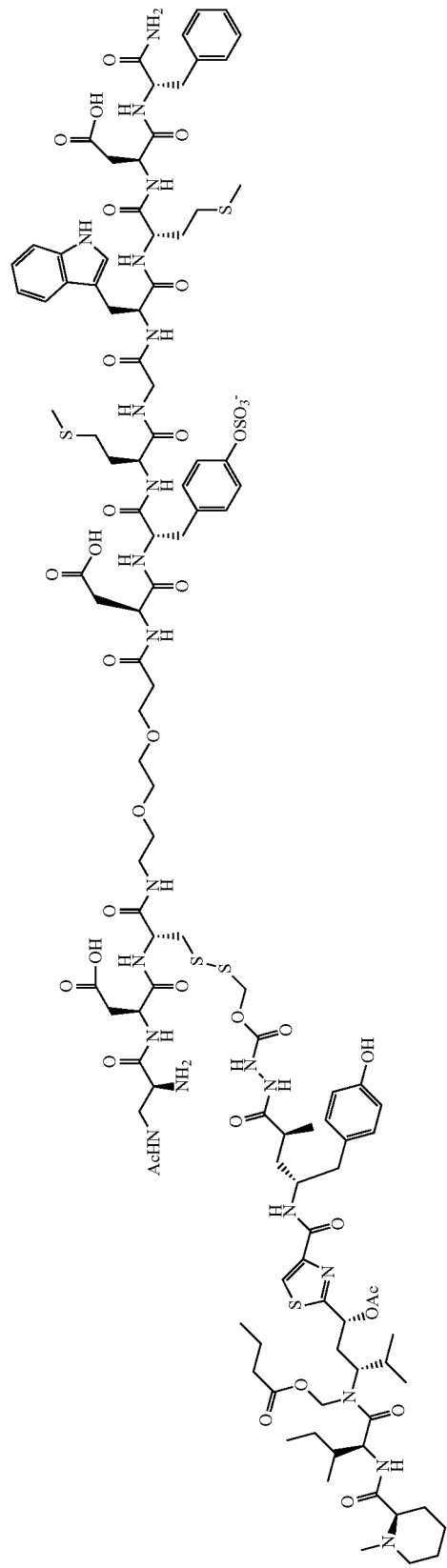

EC1947 was synthesized according to the procedure described in Example 8 for the synthesis and purification of EC1826 (8) in 16% yield.

$^1$H NMR (500 MHz DMSO-$d_6$) Pivotal signals: δ 8.14 (s, 1H), 7.49 (d, J=7.9 Hz, 1H), 7.31 (d, J=8.1 Hz, 1H), 7.21 (d, J=4.3 Hz, 4H), 7.16-7.10 (m, 2H), 7.10-7.05 (m, 2H), 7.05-7.00 (m, 3H), 6.97 (d, J=8.0 Hz, 2H), 6.92 (t, J=7.5 Hz, 1H), 6.59 (d, J=8.2 Hz, 2H), 6.17 (d, J=12.1 Hz, 1H), 5.70 (dd, J=11.1, 2.2 Hz, 1H), 5.24 (d, J=12.1 Hz, 1H), 2.08 (s, 3H), 2.03 (s, 3H), 1.96 (s, 3H), 1.95 (s, 3H), 1.81 (s, 3H). ([M+2H]$^+$)/2=Calculated 1295.9, found 1296.9.

Example 12: Synthesis of EC1785 (12)

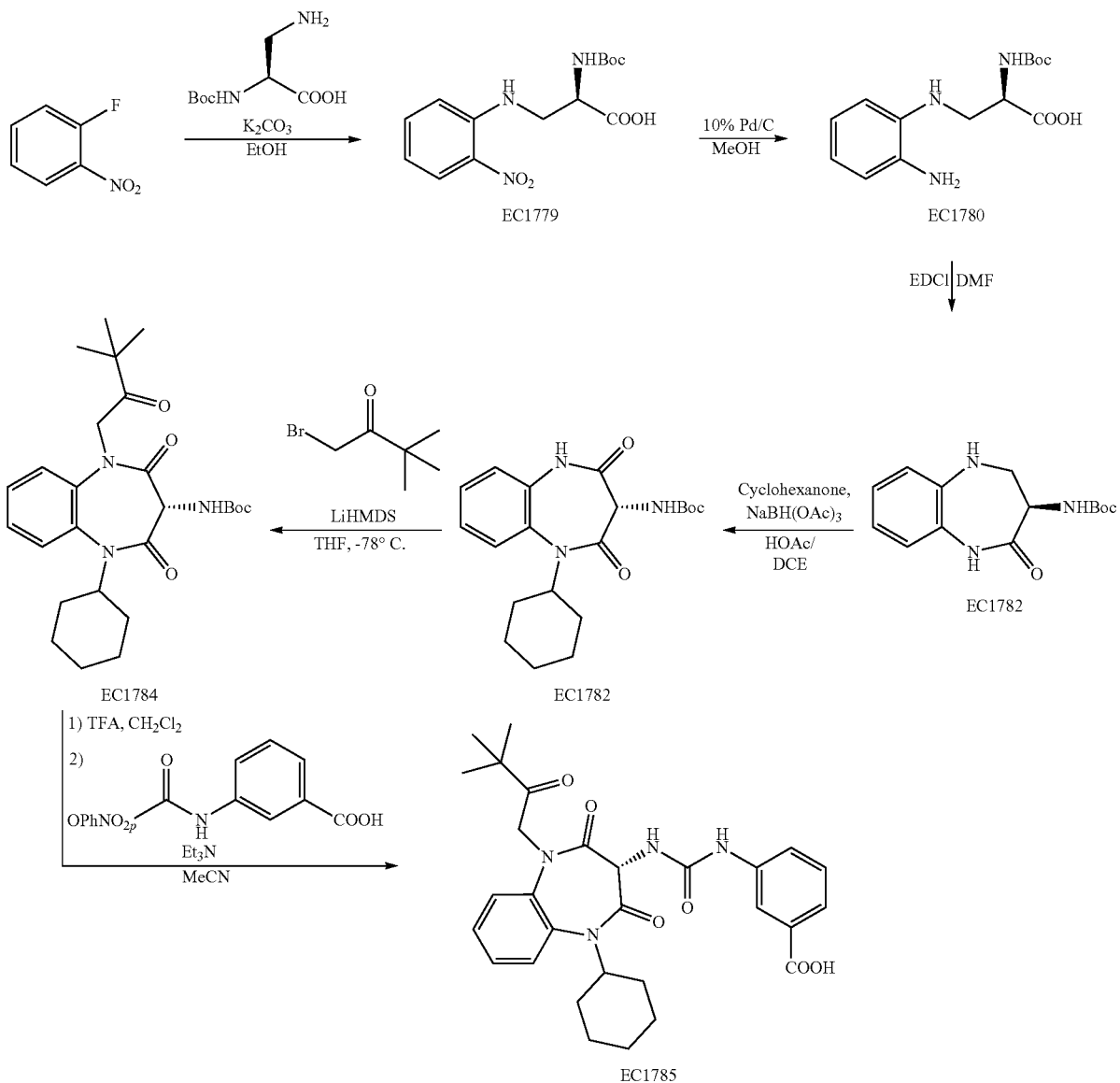

The aqueous layer was acidified to pH 3 using 2 N HCl, and extracted with ethy actetate (3×). The organic extracts were combined, dried over $Na_2SO_4$ and the solvent removed under vacuum to yield the desired acid, EC1779 (3.66 g, 79%).

$^1$H NMR (500 MHz CDCl$_3$): δ 8.34-8.22 (s, 1H), 8.21-8.16 (m, 1H), 7.50-7.42 (m, 1H), 7.04-6.95 (m, 1H), 6.75-6.64 (m, 1H), 5.38-5.30 (m, 1H), 4.67-4.25 (m, 1H), 3.93-3.82 (m, 1H), 3.79-3.66 (m, 1H), 1.51-1.33 (m, 9H). [M+H]$^+$=Calculated 326.1, found 326.4.

EC1780: In a dry hydrogenator vessel, EC1779 (3.66 g, 11.3 mmol) was dissolved in methanol and was added 10%

EC1779: 1-Fluoro, 2-nitro benzene (2 g, 14.2 mmol), Boc-Dap-OH (4.34 g, 21.3 mmol) and $K_2CO_3$ (5.88 g, 42.5 mmol) were dissolved in ethanol (30 ml) and refluxed overnight. Upon cooling, the solvent was removed under vacuum, dissolved and in $H_2O$ and washed with dietyl ether.

Pd/C (360 mg). The atmosphere were replaced with 1 atm $H_2$ gas and stirred for 3 hrs. Upon completion, the mixture was filtered through celite, the pad was washed with methanol and the filtrate as concentrated under vacuum to yield amine, EC1780 (3.30 g, 99%).

$^1$H NMR (500 MHz CDCl$_3$): δ 6.92-6.76 (m, 2H), 6.73-6.64 (m, 2H), 4.45-4.37 (m, 1H), 3.53-3.41 (m, 2H), 1.36 (s, 9H). [M+H]$^+$=Calculated 296.3, found 296.6.

EC1782: EC1780 (3.30 g, 11.1 mmol) was dissolved in DMF (110 ml) and cooled to 0° C. under argon atmosphere. To the solution, EDCI.HCl (2.35 g, 12.3 mmol) was added, warmed to room temperature and stirred for 18 hrs. The reaction mixture was diluted with H$_2$O (330 ml), acidified with 2N HCl and extracted with ethyl acetate (3×). The organic extracts were combined, dried over Na$_2$SO$_4$, concentrated under vacuum and purified using silica gel chromatography to yield lactam, EC1782 (3.01 g, 97%).

$^1$H NMR (500 MHz CDCl$_3$): δ 8.42 (s, 1H), 6.99-6.67 (m, 4H), 5.82-5.74 (m, 1H), 4.54-4.43 (m, 1H), 4.08-4.00 (m, 1H), 3.89-3.81 (m, 1H), 3.46-3.37 (m, 1H), 1.44 (s, 9H). [M+H]$^+$=Calculated 278.3, found 278.4.

EC1783: EC1782 (3.01 g, 10.9 mmol) and cyclohexanone (1.46 ml, 14.1 mmol) were dissolved in a acetic acid:dichloroethane (1:1, 60 ml). The reaction mixture was stirred for 1 hr, followed by the addition of NaBH(OAc)$_3$ (3.68 g, 17.4 mmol) and left to stir for 1 hr. The reaction was quenched by the addition of 1N NaOH until pH10. The mixture was extracted with ethyl acetate, dried over Na$_2$SO$_4$, concentrated and purified using silica gel chromatography to yield tertiary amine, EC1783 (3.81 g, 98%).

$^1$H NMR (500 MHz CDCl$_3$): δ 7.16-6.84 (m, 4H), 4.39-4.28 (m, 1H), 3.62-3.56 (m, 1H), 3.36-3.05 (m, 2H), 1.98-1.91 (m, 1H), 1.82-1.76 (m, 1H), 1.71-1.46 (m, 4H), 1.32 (s, 9H), 1.22-1.04 (m, 4H). [M+H]$^+$=Calculated 360.5, found 360.5.

EC1784: In a dry flask, EC1783 (3.81 g, 10.6 mmol) was dissolved in THF (100 ml) under argon and chilled to −78° C. To the chilled solution was added LiHMDS (11.13 ml, 11.1 mmol) dropwise, stirred for 30 mins, subsequent addition of bromopinacolone (1.85 ml, 13.8 mmol) and left to warm to room temperature over 30 mins. The reaction was quenched with saturated NH$_4$Cl and extracted with ethyl acetate (3×). The organic extracts were combined, dried over Na$_2$SO$_4$, concentrated acetate) to yield EC1784 (4.43 g, 91%).

$^1$H NMR (500 MHz CDCl$_3$): δ 7.19-7.11 (m, 2H), 7.01-6.93 (m, 2H), 5.59-5.51 (m, 1H), 5.06 (d, J=17.6 Hz, 1H), 4.48-4.40 (m, 1H), 4.12 (d, J=17.6 Hz, 1H), 3.65-3.55 (m, 1H), 3.29-3.22 (m, 1H), 3.20-3.15 (m, 1H), 2.03-1.98 (m, 2H), 1.83-1.77 (m, 1H), 1.76-1.54 (m, 4H), 1.36 (s, 9H), 1.28-1.21 (m, 10H), 1.20-1.15 (m, 3H). [M+H]$^+$=Calculated 458.6, found 458.7.

EC1785*: In a flask, EC1784 (1 g, 2.19 mmol) was dissolved in 30% TFA in DCM at 0° C. and left to warm to room temperature and stirred for 1 h. Upon complete removal of the Boc protecting group, the solvent was removed under reduced pressure, and the crude residue was left under high vacuum for 3 hr. The crude residue, activated amine (0.99 g, 3.28 mmol) were dissolved in MeCN (20 ml) under argon and chilled to 0° C. To the reaction mixture, DIPEA (1.95 ml, 10.9 mmol) was added dropwise and the reaction was left to warm to room temperature and stirred for 2 hr. The reaction was quenched with saturated NH$_4$Cl and extracted with ethyl acetate (3×). the organic extracts were combined, dried over Na$_2$SO$_4$, concentrated and purified on silica gel chromatography to yield acid, EC1785 (1.09 g, 95%).

$^1$H NMR (500 MHz CDCl$_3$) δ 8.37 (d, J=7.8 Hz, 1H), 8.21 (s, 1H), 7.72 (s, 1H), 7.59 (d, J=7.8 Hz, 1H), 7.38 (d, J=5.3 Hz, 1H), 7.37-7.31 (m, 1H), 7.24-7.18 (m, 2H), 7.04-6.98 (m, 2H), 5.18 (d, J=17.7 Hz, 1H), 4.74-4.65 (m, 1H), 4.17 (d, J=17.6 Hz, 1H), 3.84-3.76 (m, 1H), 3.45-3.37 (m, 1H), 3.27-3.18 (m, 1H), 2.09-2.02 (m, 1H), 1.89-1.74 (m, 2H), 1.72-1.56 (m, 3H), 1.49-1.32 (m, 3H), 1.26 (s, 9H), 1.25-1.14 (m, 1H). [M+H]$^+$=Calculated 521.6, found 521.6.

Example 13: Fmoc-Glu(O$^t$Bu)-EC0475-Glu(O$^t$Bu)-EC0475-Boc-Dap-Asp(O$^t$Bu)-Cys(Trt)-Resin (13)

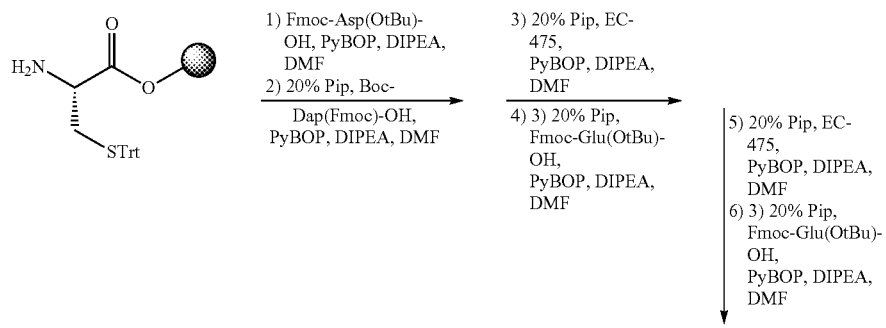

-continued

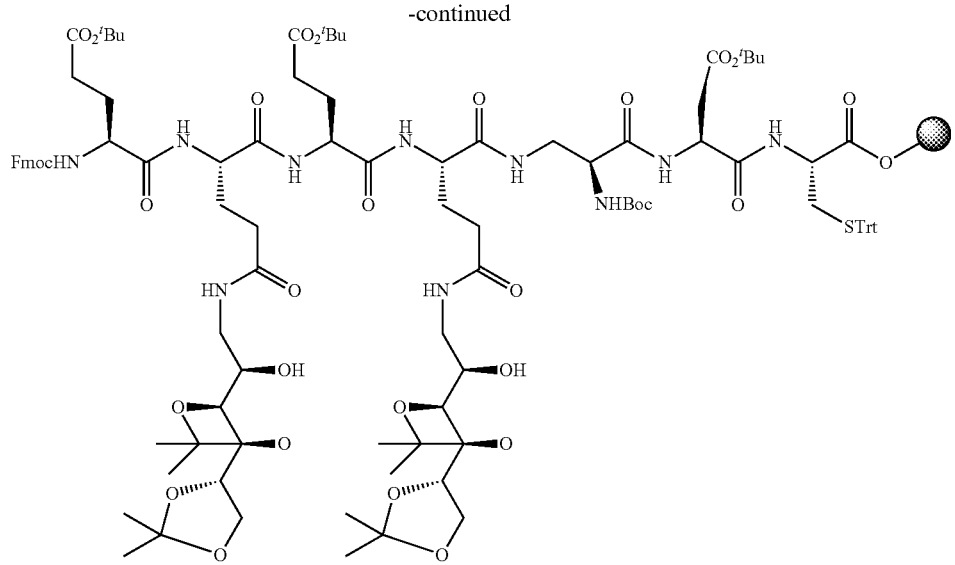

In a peptide synthesis vessel, H-Cys(Trt) resin (2.38 g, 1.5 mmol) was placed and washed with DMF (3×10 ml). Initial Fmoc deprotection was performed using 20% piperidine in DMF (3×10 ml) solution for 10 mins per cycle. Subsequent washes of DMF (3×10 ml) and i-PrOH (3×10 ml), a Kaiser test was done to determine reaction completion. Following another DMF wash (3×10 ml); a Fmoc-Asp(O$^t$Bu)-OH solution (1.23 g, 3.0 mmol, 2.0 eq.) in DMF, PyBOP (1.56 g, 3.0 mmol, 2.0 eq.) and DIPEA (0.80 ml, 4.5 mmol, 3.0 eq.) were added to the vessel and the solution bubbled with Argon for 1 hour. The coupling solution was filtered, the resin was washed with DMF (3×10 ml) and i-PrOH (3×10 ml) and a Kaiser test was done to assess reaction completion. The above process was performed successively for the additional couplings.

TABLE 4

Reagents for Resin bound protected linker peptide (1) synthesis

| Compound (All Compounds in this column are commercially available) | mmol | Equivalent | Molecular Weight | Quantity (grams) |
|---|---|---|---|---|
| H-Cys(Trt)-Resin (Loading ~0.63 mmol/g) | 1.5 | 1 | | 2.38 |
| Fmoc-Asp(O$^t$Bu)—OH | 3.0 | 2 | 411.5 | 1.23 |
| Boc-Dap(Fmoc)—OH | 3.0 | 2 | 426.5 | 1.28 |
| EC0475 | 3.0 | 2 | 612.7 | 1.84 |
| Fmoc-Glu(O$^t$Bu)—OH | 3.0 | 2 | 425.5 | 1.28 |
| EC0475 | 3.0 | 2 | 612.7 | 1.84 |
| Fmoc-Glu(O$^t$Bu)—OH | 3.0 | 2 | 425.5 | 1.28 |
| PyBOP | 3.0 | 2 | 520.31 | 1.56 |
| i-Pr$_2$NEt | 4.5 | 3 | 129.24 | 0.58 (d = 0.742) |

Example 14: Synthesis of EC1786 (14)

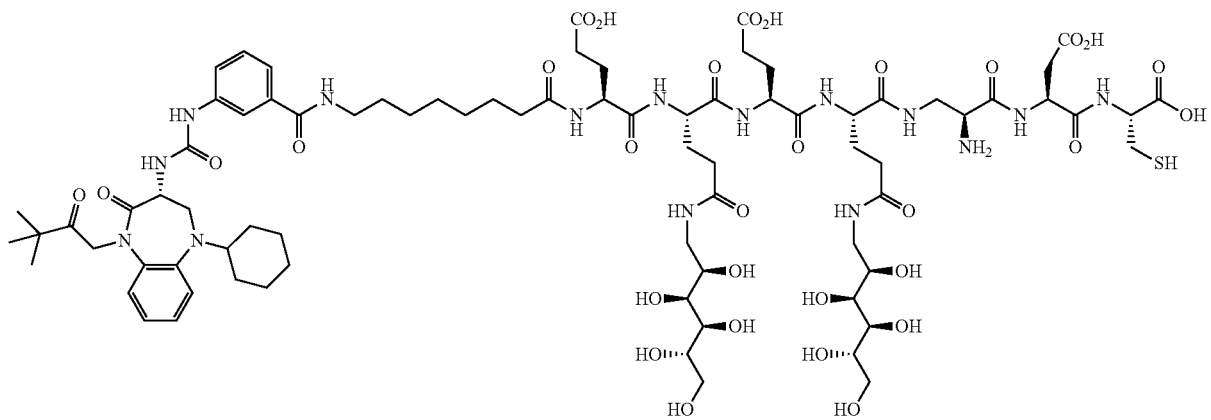

EC 1786

In a peptide synthesis vessel, resin bound-protected linker peptide, 13 (0.3 g, 0.009 mmol) was placed and was subjected to previously reported standard solid phase synthesis for the coupling of Fmoc-8-amino-caprylic acid and EC1785 to protected Linker-resin, 13. Resin cleavage was performed with a cocktail consisting of 94% $CF_3CO_2H$, 2.5% EDT, 2.0% triisopropylsilane and 1.5% $H_2O$. The cleavage cocktail (10 ml) was poured onto the resin and bubbled with Argon for 30 mins, followed by filtration into a clean flask. Further cleavage was performed twice successively with fresh cleavage cocktail for 10 mins of bubbling. The combined filtrate was poured onto cold diethyl ether, the precipitate formed was collected by centrifugation at 4000 rpm for 5 mins (3×). The precipitate was obtained following decanting and drying of the solid under vacuum; the desired linker was then purified by preparative HPLC (mobile phase A=10 mM Ammonium acetate, pH=5; Organic phase B=Acetonitrile; Method; 10% B to 100% B in 30 mins) to yield EC1786 (53 mg, 32%)

$^1$H NMR (500 MHz DMSO-$d_6$) Pivotal signals: δ 7.65 (s, 1H), 7.42-7.37 (m, 1H), 7.29-7.26 (m, 1H), 7.25-7.18 (m, 3H), 7.08, 7.03 (m, 1H), 6.97-6.92 (m, 1H), 5.06-4.98 (m, 1H), 4.58-4.48 (m, 1H), 4.39-4.30 (m, 3H), 3.06-2.96 (m, 3H), 2.88-2.81 (m, 1H), 2.80-2.73 (m, 1H), 1.15-1.06 (m, 14H). $[M+H]^+$=Calculated 1809.9, found 1810.3.

TABLE 5

Reagents for EC1786 synthesis

| Compound (All Compounds in this column are commercially available) | mmol | Equivalent | Molecular Weight | Quantity (grams) |
|---|---|---|---|---|
| Protected-Linker-Cys(Trt)-Resin (Loading ~0.63 mmol/g) | 0.009 | 1 | | 0.3 |
| Fmoc-8-amino-caprylic acid | 0.181 | 2 | 381.5 | 0.07 |
| EC1785 | 0.181 | 2 | 520.6 | 0.09 |
| PyBOP | 0.181 | 2 | 520.31 | 0.09 |
| DIPEA | 0.272 | 3 | 129.24 (d = 0.742) | $2.11 \times 10^{-6}$ |

Example 15: Synthesis of EC1812 (15)

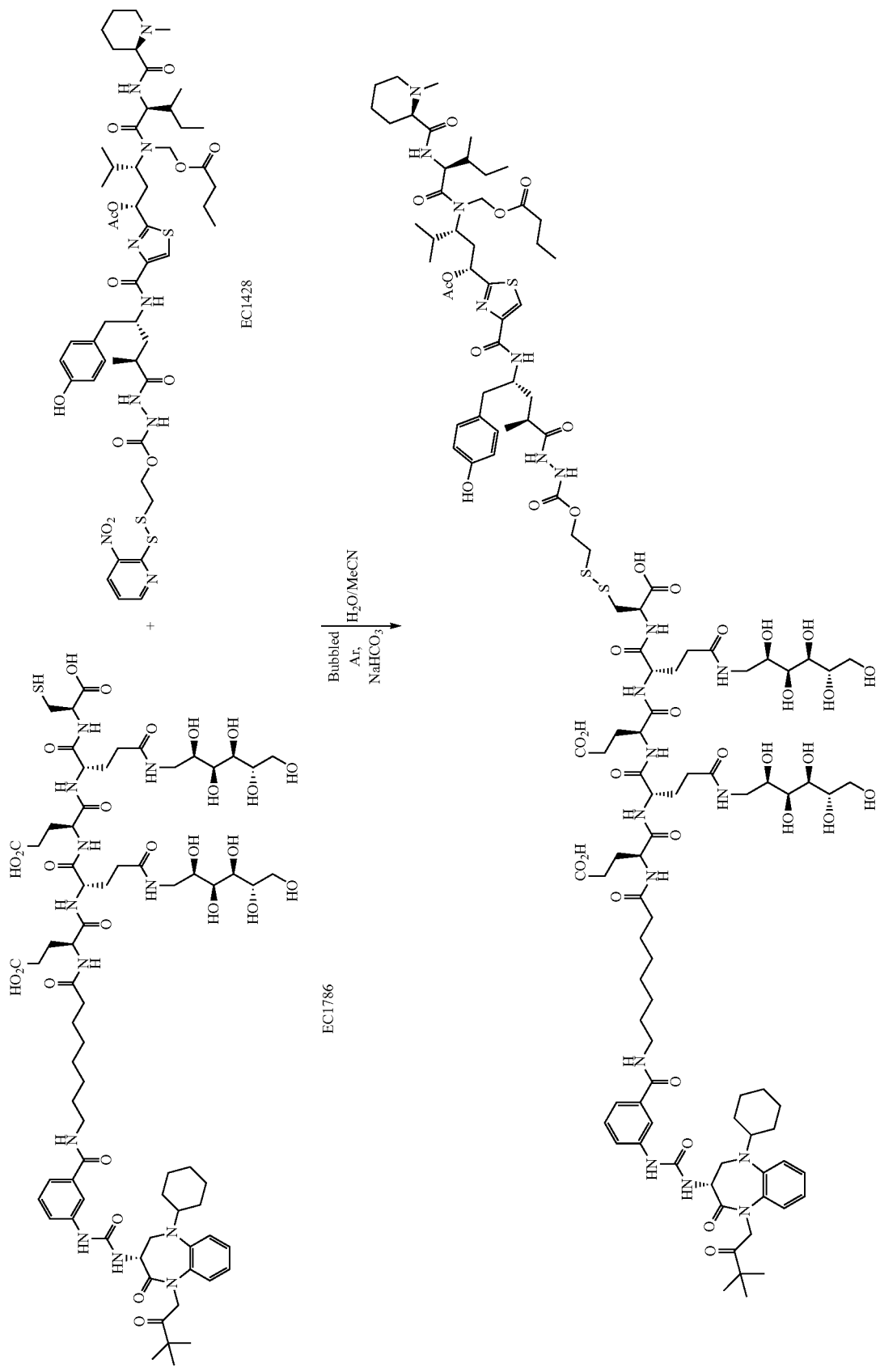

Peptide (EC1786) (28 mg, 17.4 μmol) was 1.5 ml of DI H$_2$O being sparged with Argon. A solution of EC1428* (17.5 mg, 15.8 μmol) in 1.5 ml acetonitrile was added to the sparging solution and adjusted to pH7 using a saturated NaHCO$_3$ solution. Upon completion the reaction mixture was diluted with DI H$_2$O to 10% acetonitrile in H$_2$O and purified by preparative HPLC (mobile phase A=50 mM Ammonium Bicarbonate, pH=7; Organic phase B=Acetonitrile; Method; 10% B to 100% B in 30 mins) to yield EC1812 (15) (9.6 mg, 24%).

$^1$H NMR (500 MHz DMSO-d$_6$) Pivotal signals: δ 8.15 (s, 1H), 7.64-7.52 (m, 2H), 7.31-7.27 (m, 1H), 7.26-7.18 (m, 3H), 7.08-7.03 (m, 1H), 6.99-6.91 (m, 3H), 6.48 (d, J=7.8 Hz, 2H), 6.21-6.13 (m, 1H), 5.72-5.66 (m, 1H), 5.24-5.18 (m, 1H), 5.05-4.99 (m, 1H), 4.42-4.31 (m, 5H), 4.36-4.03 (m, 8H), 2.81-2.72 (m, 2H), 1.15-1.08 (m, 11H). ([M+2H]$^+$)/2=Calculated 1277.9, found 1278.

*EC1428 was prepared according to the procedures set forth in US20140107316.

Example 16: Synthesis of EC1975 (16)

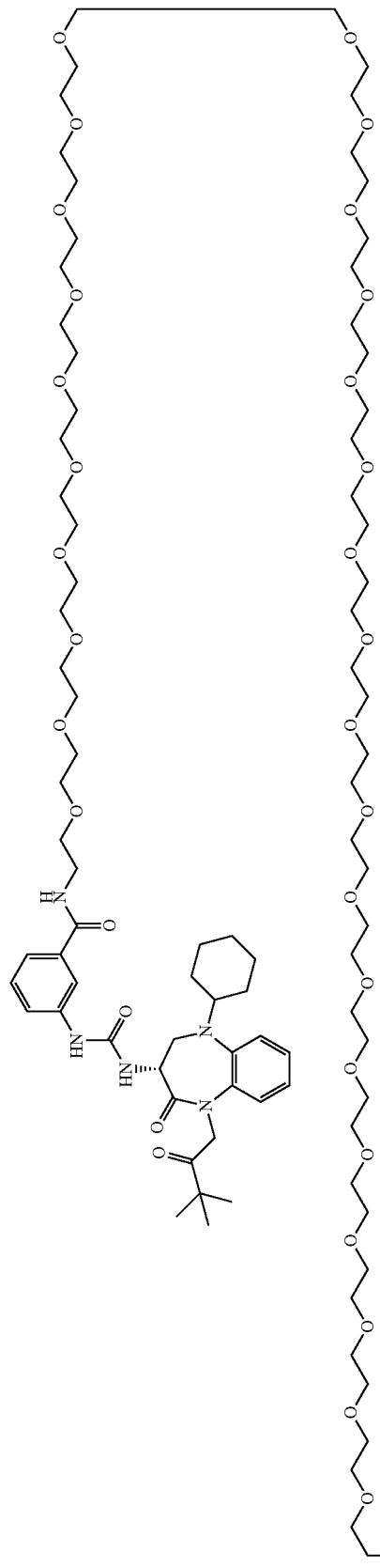
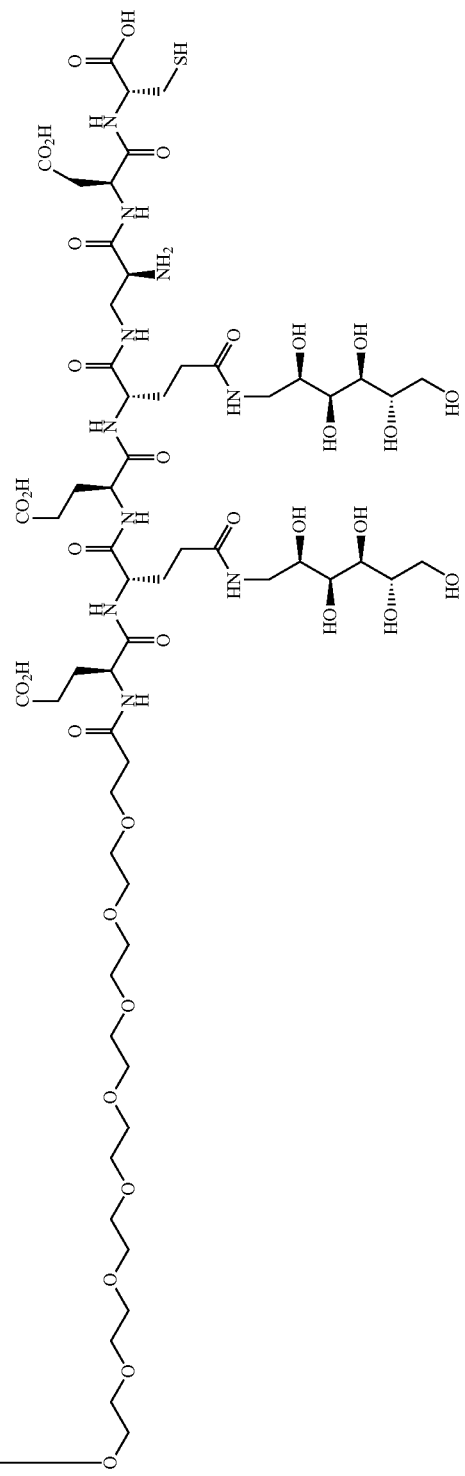

The general procedure listed for the synthesis of peptide linker, EC1786 was followed for the coupling of Fmoc-N-amido-dPEG®$_{36}$-acid and EC1785 to protected linker-resin, 13. Resin cleavage and purification was performed with the previously reported procedure to yield desired peptide EC1975 (227 mg, 30%)

$^{1}$H NMR (500 MHz DMSO-d$_{6}$) Pivotal signals: δ 7.67 (s, 1H), 7.38-7.33 (m, 1H), 7.31-7.23 (m, 2H), 7.19 (s, 2H), 7.06-7.01 (m, 1H), 6.95-6.90 (m, 1H), 4.98-4.92 (m, 1H), 4.61-4.47 (m, 1H), 3.97-3.84 (m, 1H), 3.15-2.98 (m, 4H), 1.71-1.53 (m, 3H), 1.26-1.02 (m, 14H). ([M+2H]$^{+}$)/2=Calculated 1277.9, found 1278.

Example 17: Synthesis of EC1977 (17)

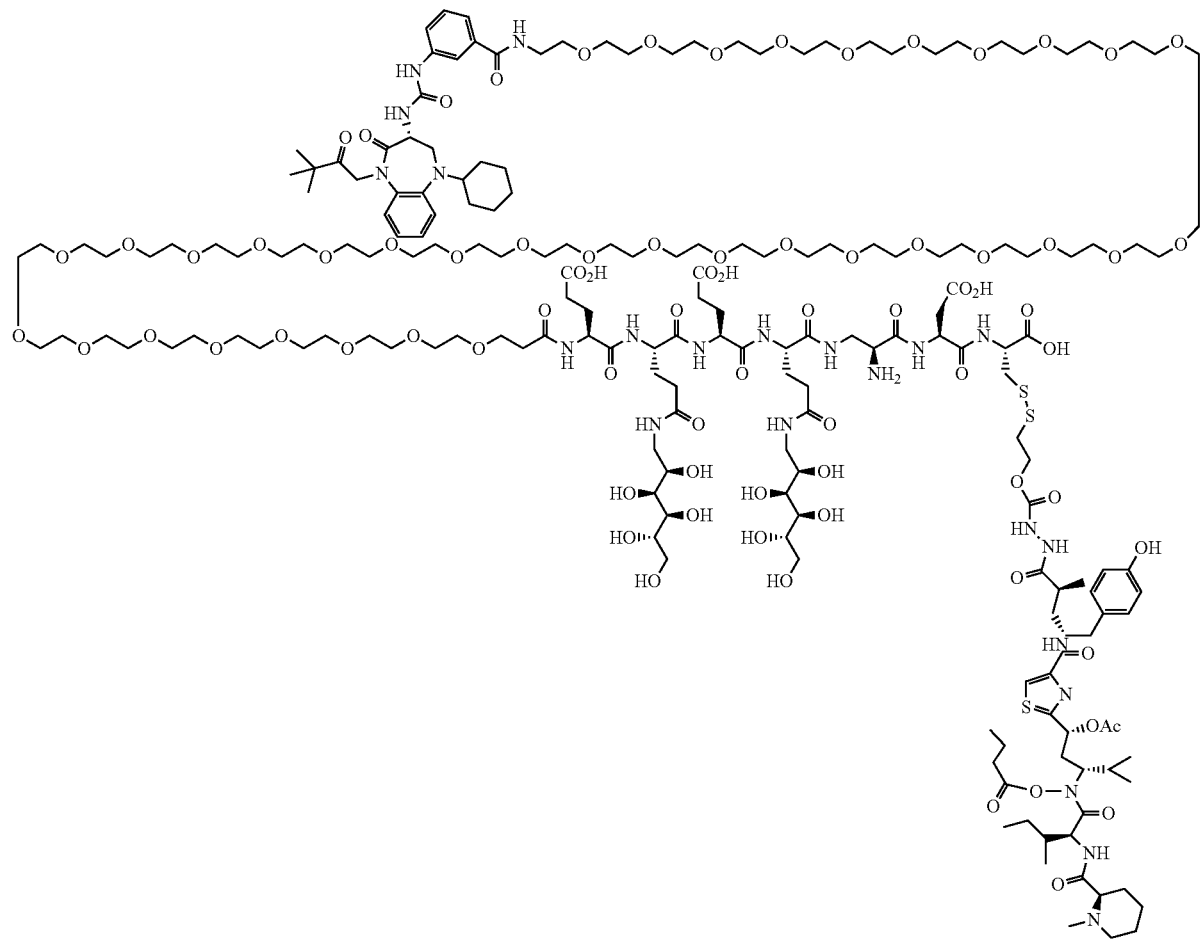

EC1977

Peptide (EC1975) (0.70 mg, 21.1 μmol) was 3 ml of DI H$_2$O being sparged with Argon. A solution of EC1428* (28 mg, 25.3 μmol) in 3 ml acetonitrile was added to the sparging solution and adjusted to pH7 using a saturated NaHCO$_3$ solution. Upon completion the reaction mixture was diluted with DI H$_2$O to 10% acetonitrile in H$_2$O and purified by preparative HPLC (mobile phase A=50 mM Ammonium Bicarbonate, pH=7; Organic phase B=Acetonitrile; Method; 10% B to 100% B in 30 mins) to yield EC1977 (17) (10 mg, 11%).

$^1$H NMR (500 MHz DMSO-d$_6$) Pivotal signals: δ 8.11 (s, 1H), 7.69-7.67 (s, 1H), 7.40-7.37 (m, 1H), 7.32-7.18 (m, 4H), 7.08-7.02 (m, 1H), 6.98-6.00 (m, 3H), 6.56 (d, J=7.8 Hz, 2H), 6.13-6.05 (m, 1H), 5.69-5.63 (m, 1H), 5.26-5.23 (m, 1H), 5.02-4.97 (m, 1H), 3.05-2.83 (m, 6H), 2.37-2.26 (m, 4H), 1.14-1.03 (m, 12H), 0.82-0.68 (m, 10H). ([M+3H]$^+$)/3=Calculated 1424.6, found 1424.7.

Example 18: Synthesis of EC1906 (18)

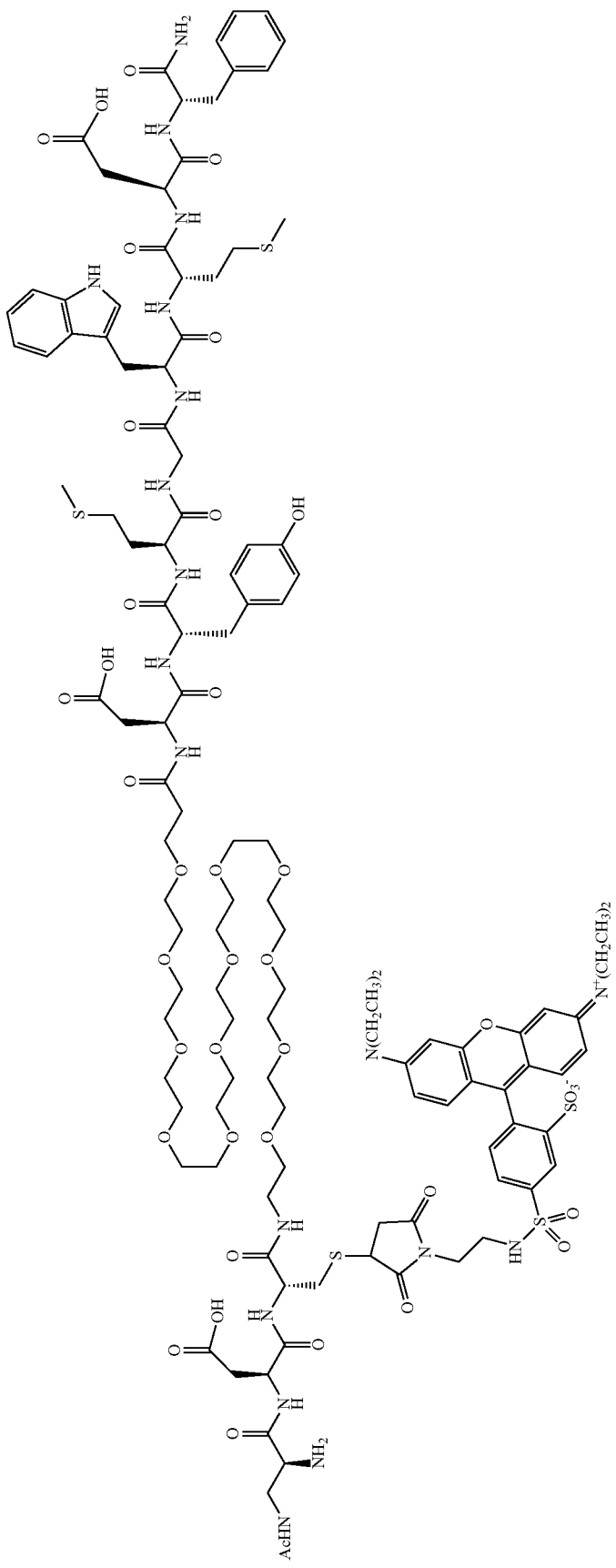

In a flask, peptide spacer, EC1872 (5.5 mg, 2.74 µmol) and maleimido Rhodamine dye (1.24 mg, 1.83 µmol) were dissolved in DMSO (1 ml) under argon. To the reaction was mixture was added DIPEA (4.9 µl, 27.4 µmol) and left to stir for 30 mins. Upon completion, the reaction mixture was diluted with deionized $H_2O$ (5 ml) and purified using preparative HPLC (mobile phase A=50 mM Ammonium Bicarbonate, pH=7; Organic phase B=Acetonitrile; Method; 10% B to 100% B in 30 mins) to yield 18 (1.7 mg, 35%). $([M+2H]^+)/2$=Calculated 1346.04, found 1346.15.

BIOLOGY EXAMPLES

Example 1: In Vitro Analysis of CCK2R Conjugates

CCK2R-positive HEK-CCK2R cells were seeded in 12-well Falcon plates and allowed to form nearly confluent monolayers overnight in RPMI/HIFCS. Each well then received increasing concentrations of CCK2R targeted conjugates (n=4). Cells were pulsed for 2 h at 37° C., rinsed with medium, and then chased in fresh medium up to 72 h. Spent medium was aspirated and replaced with medium containing [$^3$H]thymidine. Following a 2 h incubation, cells were washed with PBS and then treated with 5% trichloroacetic acid. The trichloroacetic acid was aspirated and cells were solubilized in 0.25 N sodium hydroxide. Each solubilized sample were transferred to scintillation vials containing Ecolume scintillation cocktail and counted in a liquid scintillation counter. Final results were expressed as the percentage of [$^3$H]thymidine incorporation relative to untreated controls and IC50 values calculated using GraphPad Prism software. Results are shown in Table 6.

TABLE 6

| Conjugate | $IC_{50}$ (nm) |
|---|---|
| EC1826 | 3.3 |
| EC1868 | 0.2 |
| EC1873 | 2.8 |
| EC1947 | 0.9 |

Example 2: Biodistribution of $^{99m}$Tc-CCK8 Agents in HEK-CCK2R Tumor Model

Female Balb/c nu/nu mice were fed ad libitum with 2918 irradiated Teklad Global 18% Rodent Diet for the duration of the experiment. HEK-CCK2R tumor cells were inoculated subcutaneously at the right flank of each mouse. Mice were dosed with 50 nmol/kg of the radiolabeled agent through the lateral tail vein in a volume of 200 µL PBS. Mice dosed with $^{99m}$Tc-EC1981 showed higher uptake in CCK2R expressing tissues such as tumor (2.21% ID/g) and kidney (14.25% ID/g) than $^{99m}$Tc-EC1825 (tumor, 0.69% ID/g and kidney, 1.48% ID/g). Results are shown in FIG. 1.

Example 3: Antitumor Activity in HEK-CCK2R Tumor Model

Female Balb/c nu/nu mice were fed ad libitum with 2918 irradiated Teklad Global 18% Rodent Diet for the duration of the experiment. HEK-CCK2R tumor cells were inoculated subcutaneously at the right flank of each mouse. Mice were dosed through the lateral tail vein under sterile conditions in a volume of 200 µL of phosphate-buffered saline (PBS).

Growth of each s.c. tumor was followed by measuring the tumor two times per week. Tumors were measured in two perpendicular directions using Vernier calipers, and their volumes were calculated as $0.5 \times L \times W^2$, where L=measurement of longest axis in mm and W=measurement of axis perpendicular to L in mm.

Figure 2:
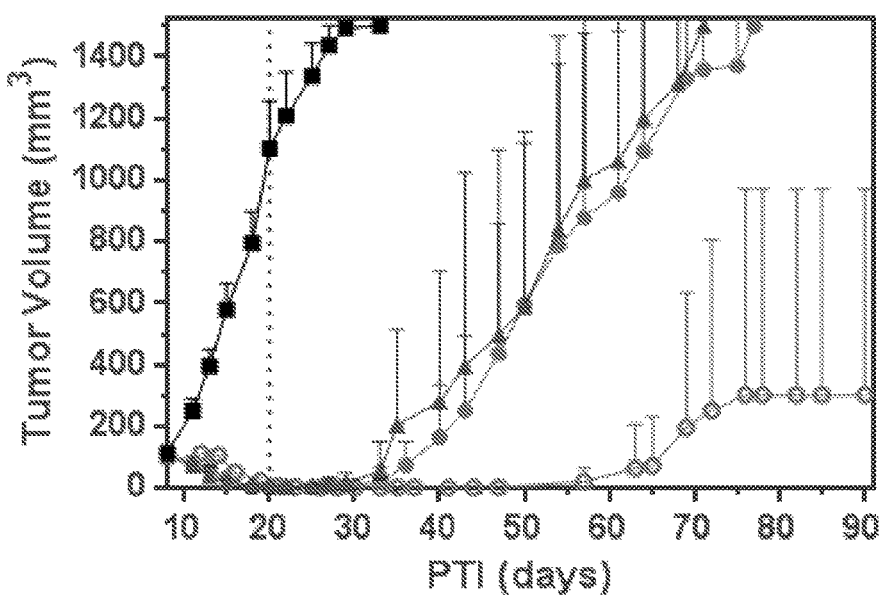
FIG. 2 shows that the conjugates described herein are more efficacious in vivo, as compared to control, in mice bearing subcutaneous HEK-CCK2R tumor cells at a dose of 2 μmol/kg, TIW×2 weeks. (■) control; (▲) EC1873 {1,4,0}; (●) EC1868 {0,5,0}; (○) EC1947 {0,1,4}. All treatment groups were n=5; and each treatment group indicates {PR, CR, cure}.
Figure 3:
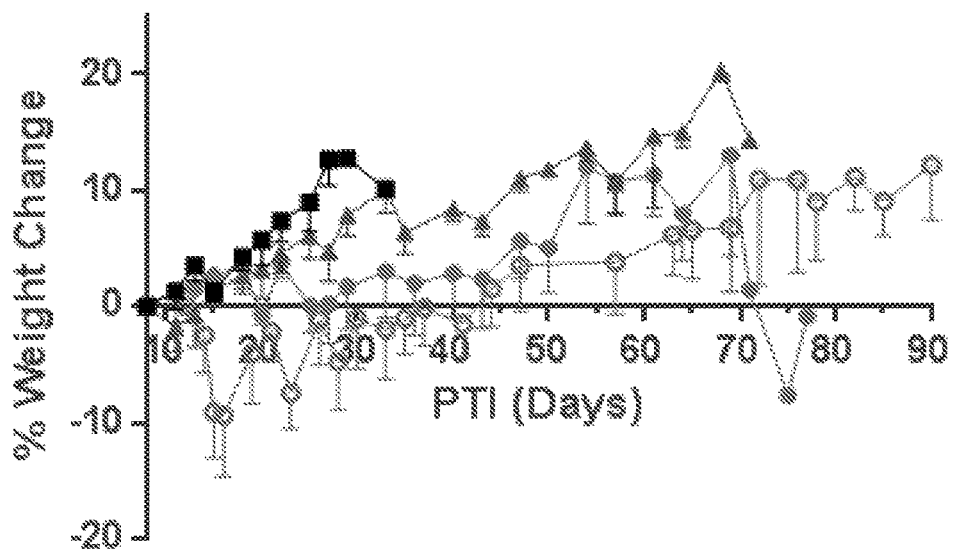
FIG. 3 shows that the conjugates described herein do not induce weight loss when administered in vivo to mice bearing subcutaneous HEK-CCK2R tumor cells tumors at a dose of 2 μmol/kg, TIW×2 weeks. (■) control; (▲) EC1873; (●) EC1868; (○) EC1947.
Figure 4:
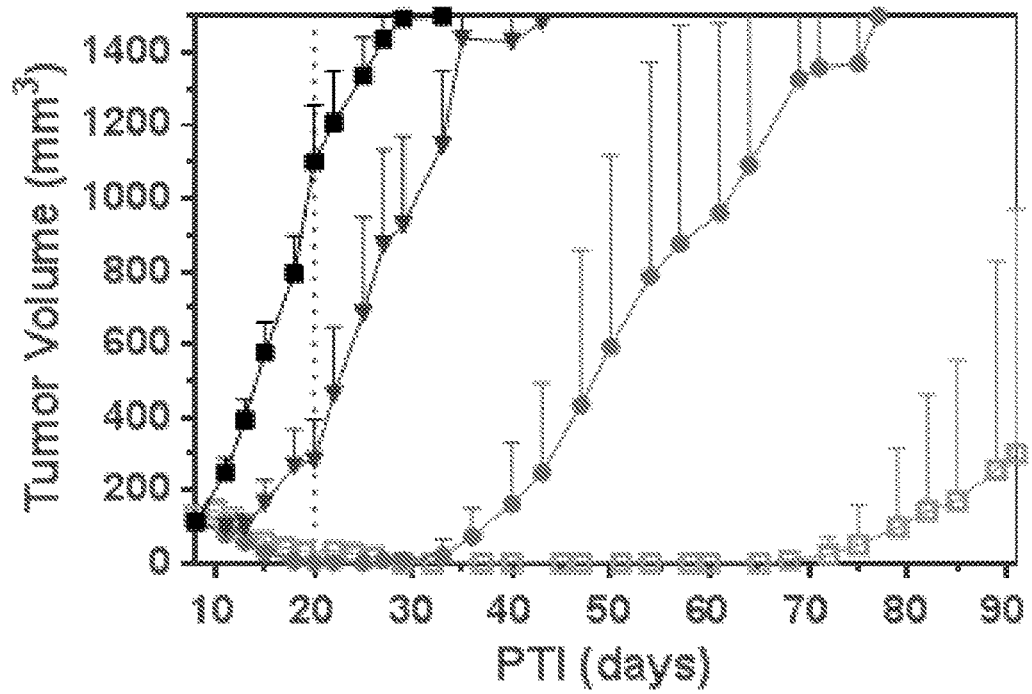
FIG. 4 shows that the conjugates described herein are more efficacious in vivo, as compared to control, in mice bearing subcutaneous HEK-CCK2R tumor cells at a dose of 2 μmol/kg, TIW×2 weeks. (■) control; (▼) EC1812 {1,0,0}; (●) EC1868 {0,5,0}; (□) EC1977 {0,1,4}. All treatment groups were n=5; and each treatment group indicates {PR, CR, cure}.

Treatment with 2 µmol/kg of EC1947 (Sulfated CCK8-Tubulysin B SMDC), three times a week for two weeks produced maximal anti-tumor activity with 80% cures and 20% CR's. In comparison, EC1868 (CCK8-PEG3-Tubulysin B SMDC) and EC1873 (CCK8-PEG12-Tubulysin B SMDC) at the same dose and schedule produced 100% CR's and 80% CR's/20% PR's, respectively. Results are shown in FIG. 2, FIG. 3 and FIG. 4.

Example 4: In Vitro Study of Conjugates Versus Competitor

Figure 5:
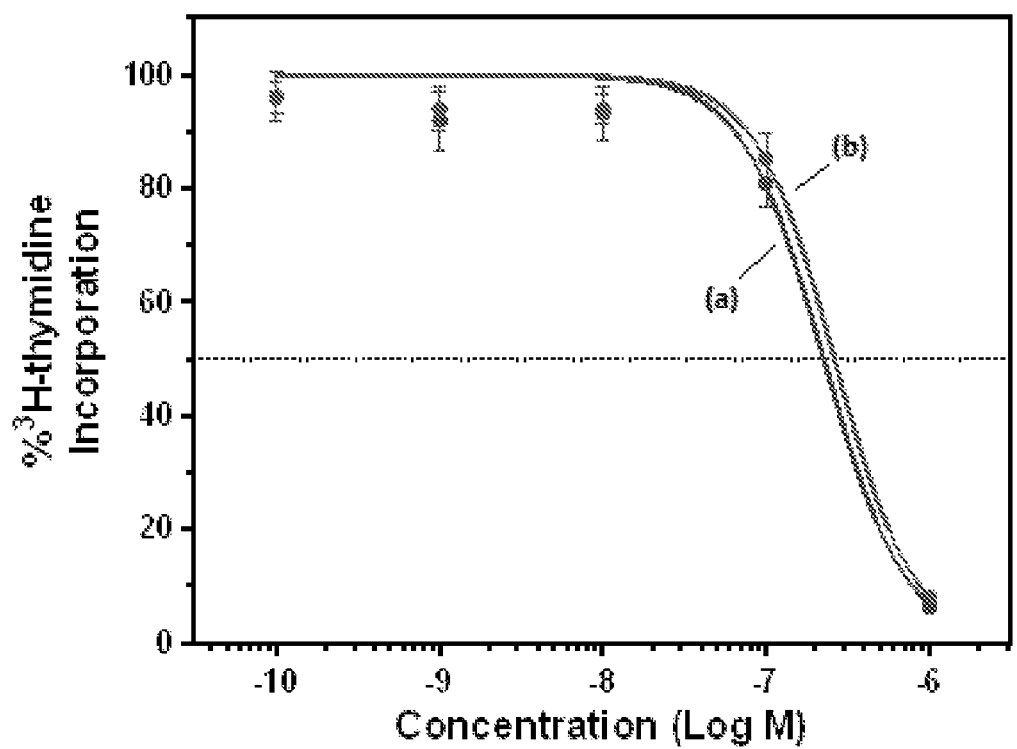
FIG. 5 shows the effect of EC1812 (Z360-tubulysin)+/− Re-EC1786 on HEK-CCK2R. EC1812 is relatively inactive on HEK-CCK2R, and the activity is not competeable with excess Re-EC1786. (a) EC1812 (IC$_{50}$=225 nM), (b) EC1812+Re-EC1786 (IC$_{50}$=262 nM).
Figure 6:
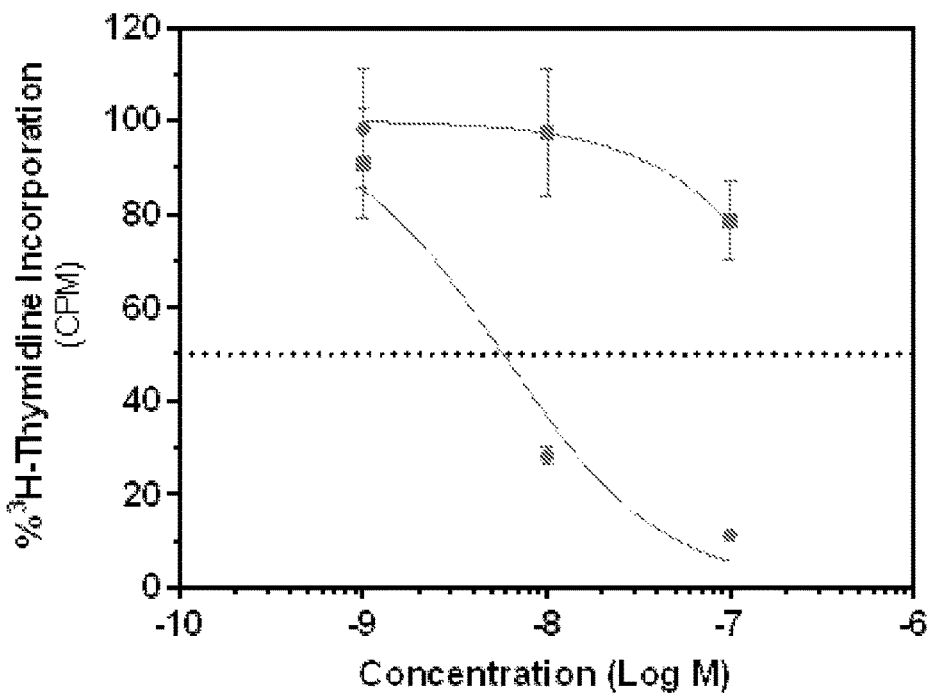
FIG. 6 shows the effect of EC1868+/−Re-EC1850 on HEK-CCK2R. EX1868 exhibits potent, competeable cytotoxic activity in HEK293-CCK2R expressing cells. (●) EC1812 (IC$_{50}$=5.8 nM), (■) EC1812+Re-EC1825 (IC$_{50}$=364.7 nM).
Figure 7:
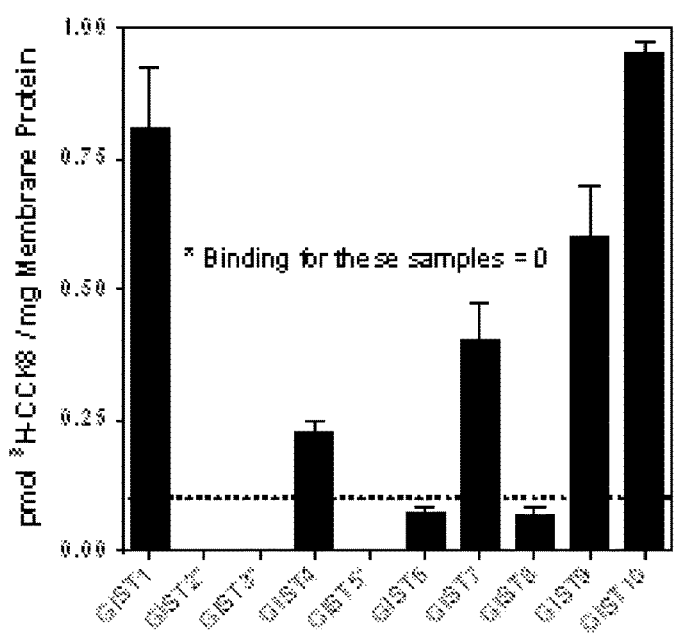
FIG. 7 shows CCK2R radioligand binding in GIST.
Figure 8:
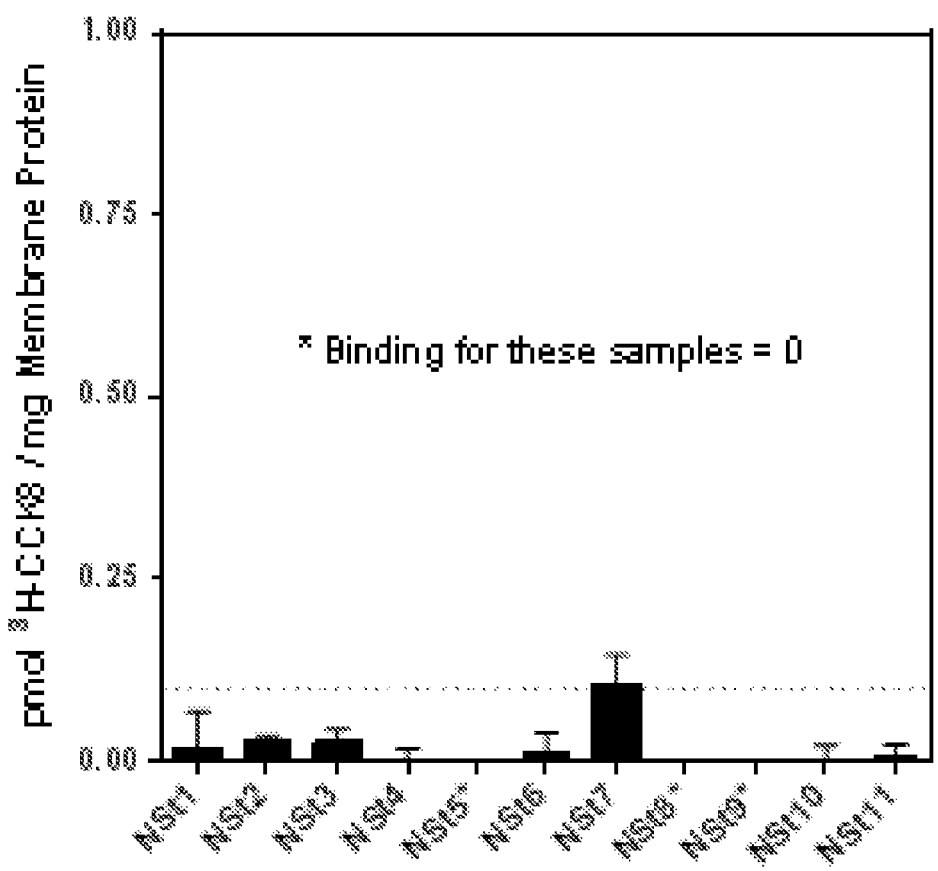
FIG. 8 shows CCK2R radioligand binding in normal stomach tissue.
Figure 9:
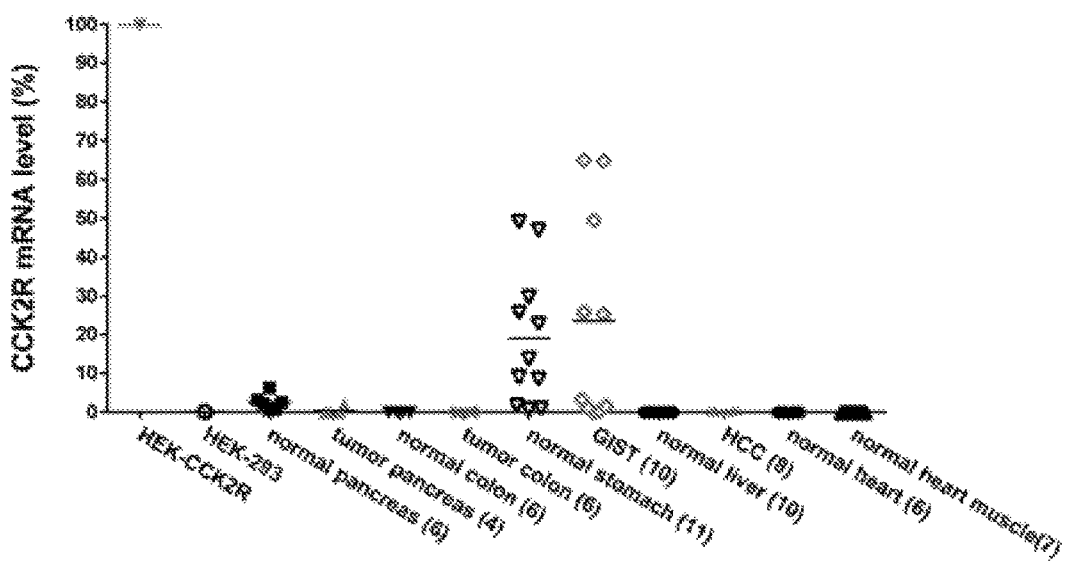
FIG. 9 shows CCK2R mRNA expression in frozen human tissues. Results show CCK2R expression in GIST and normal stomach human samples.
Figure 10:
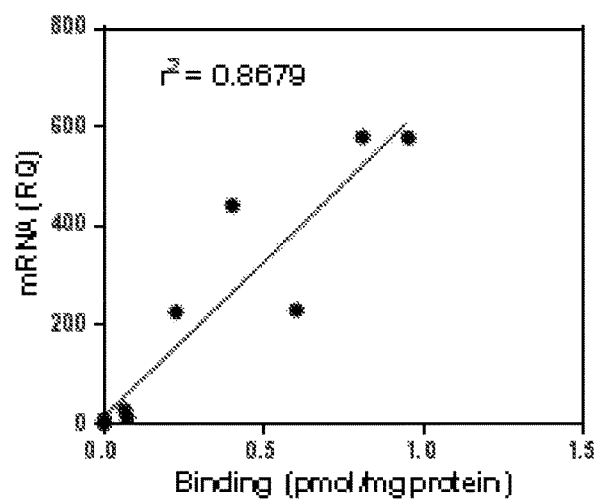
FIG. 10 shows CCK2R binding-mRNA correlation in GIST.
Figure 11A:
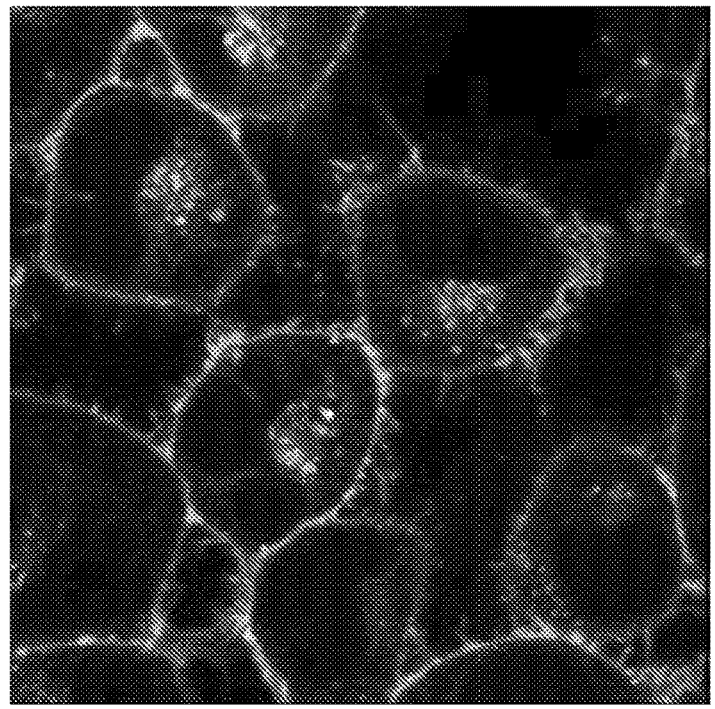
FIG. 11A: CCK2R/EC1906.
Figure 11B:
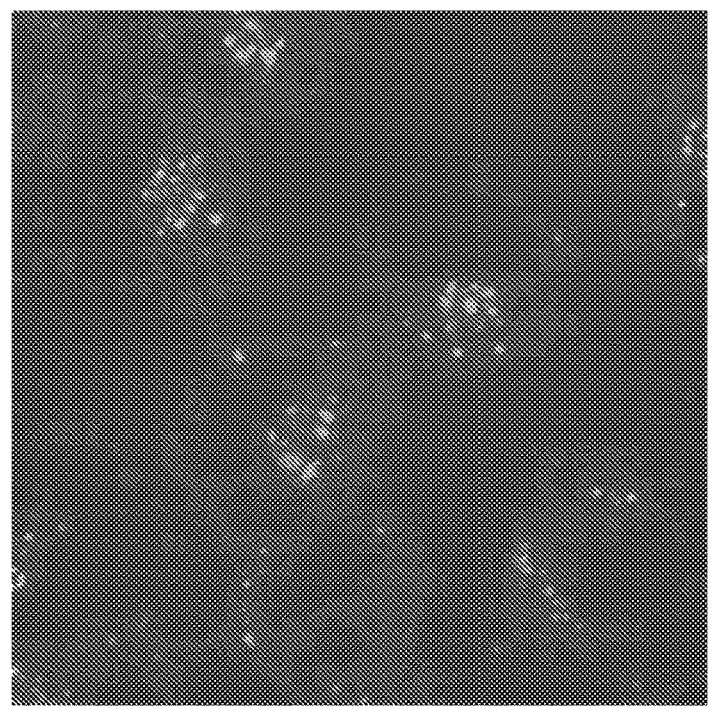
FIG. 11B: 100 nM EC1906.
Figure 11C:
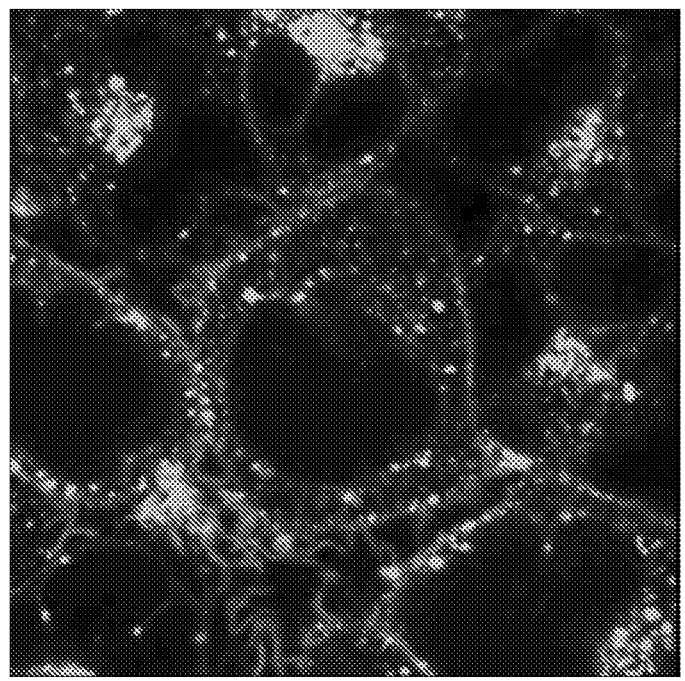
FIG. 11C: CCK2R/EC1906.
Figure 11D:
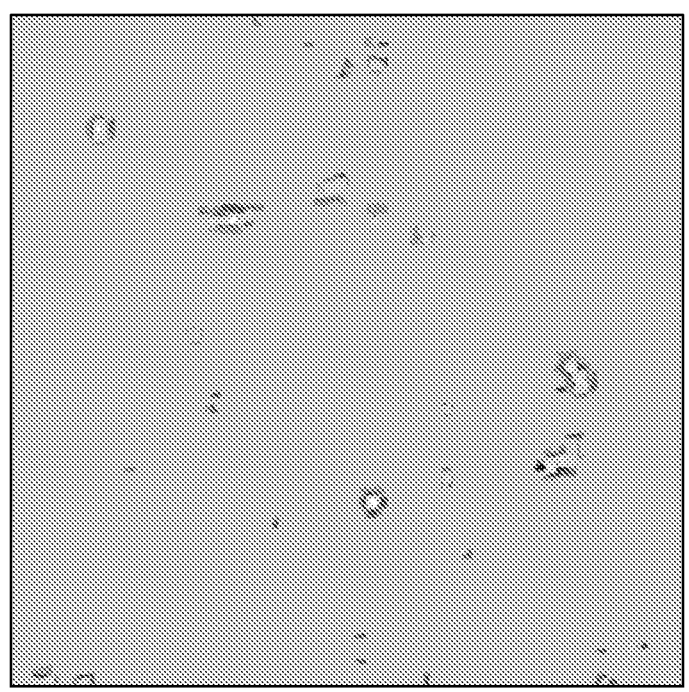
FIG. 11D: 100 nM EC1906+10 μM EC1850.

CCK2R-positive HEK-CCK2R cells were seeded in 12-well Falcon plates and allowed to form nearly confluent monolayers overnight in RPMI/HIFCS. Each well then received increasing concentrations of CCK2R targeted conjugates (EC1812 or EC1868)+/−10 µM of CCK2R binding competitor (Re-EC1786 or Re-EC1825). Cells were pulsed for 2 h at 37° C., rinsed with medium, and then chased in fresh medium up to 72 h. Spent medium was aspirated and replaced with medium containing [$^3$H]thymidine. Following a 2 h incubation, cells were washed with PBS and then treated with 5% trichloroacetic acid. The trichloroacetic acid was aspirated and cells were solubilized in 0.25 N sodium hydroxide. Each solubilized sample were transferred to scintillation vials containing Ecolume scintillation cocktail and counted in a liquid scintillation counter. Final results were expressed as the percentage of [$^3$H]thymidine incorporation relative to untreated controls and IC50 values calculated using GraphPad Prism software. Results are shown in FIG. 5 and FIG. 6.

Example 5: Preparation of Cell and Tissue Membranes for CCK2R Binding Assay

Materials: At least 100 mg of frozen tissue or one 150 cm$^2$ flask of monolayer cells; Branson Sonifier Cell Disruptor; PowerGen tissue homogenizer; homogenization Buffer stock; reconstitution buffer stock; 100 mM PMSF; Halt Protease Inhibitor Cocktail, EDTA-free (100×; Pierce), soybean trypsin inhibitor (STI) 10 mg/mL stock.

Reagent Preparations
Homogenization Buffer
10 mM HEPES, pH 6.5, 0.25 M sucrose, 1 mM EDTA, 5 mM $MgCl_2$, 1 mM PMSF, 1× Halt Protease Inhibitor Cocktail. 500 mL: 1.192 g HEPES (free acid), 42.788 g sucrose, 1 mL 0.5 M EDTA, 0.508 g $MgCl_2$. Stirred to dissolve and adjust pH to 6.5 with 1 N NaOH. Stored at 4° C. Add 10 µL of 100 mM PMSF and 10 µL of 100× Halt Protease Inhibitor Cocktail per mL of Homogenization Buffer prior to use.

KRH Buffer
25 mM HEPES, pH 7.4, 104 mM NaCl, 5 mM KCl, 2 mM $CaCl_2$, 1 mM $KH_2PO_4$, 1.2 mM $MgSO_4$. 1 L: 5.96 g HEPES (free acid), 6.08 g NaCl, 373 mg KCl, 294 mg $CaCl_2$ (dihydrate), 136 mg $KH_2PO_4$ (monobasic), 296 mg $MgSO_4$ (heptahydrate). Stirred to dissolve and adjust pH to 7.4 with 1 N NaOH. Stored at 4° C.

Reconstitution Buffer
50 mM Tris, pH 7.4+protease inhibitors+10% glycerol. Prepared 50 mM Tris by adding 606 mg of Trizma base to 100 mL Milli-Q water. Adjusted pH to 7.4 with HCl. Added L of 100 mM PMSF, 10 μL of 10 mg/mL soybean trypsin inhibitor stock, and 100 μL glycerol per mL of Tris Buffer Procedure for Monolayer Cells Note: Perform all cell preparation procedures on ice or at 4° C.

For monolayer cell cultures, dislodged cells from one T150 flask using cell dissociation solution or by scraping. Counted cells using a hemacytometer. Transferred $20\times10^6$ cells to a separate tube and centrifuged cells for 5 min. at 300×g. Resuspended cell pellet in PBS and centrifuged again. Resuspend cell pellet in 1 mL Homogenization Buffer+PMSF and Halt Protease Inhibitor Cocktail. Homogenized cells thoroughly using a Sonifier Cell Disruptor. Pulsed cells 3×5 sec at 20% amplitude on ice. Monitored cell breakage by light microscope.

Transferred homogenate to a microcentrifuge tube and spun at 10,000×g, 4° C. for 10 min. to remove unbroken cells and nuclei. Transferred supernatant to ultra microcentrifuge tubes. Centrifuged samples at 150,000×g for 45 min at 4° C. Resuspended pellet in 500 μL Reconstitution Buffer. Inverted on a rotator overnight at 4° C. Saved some of the Reconstitution Buffer for BCA protein assay the next day.

The next day, centrifuged the samples at 3000×g at 4° C. for 10 min to remove insoluble material. Retained the supernatant for receptor binding assay. Stored membrane samples at −80° C.

Procedure for Tissue

Note: perform all cell preparation procedures on ice or at 4° C.

Cut a piece of frozen tissue using a razor blade. Weighed the tissue and determine the amount of Homogenization Buffer needed. Used 1 mL Homogenization Buffer per 200 mg tissue. Placed the tissue and Homogenization Buffer into a 14 mL plastic test tube. Homogenized the tissue with the PowerGen tissue homogenizer for 1 min on ice. Observed homogenate to ensure thorough tissue disruptions. Transferred 1 mL aliquots to microcentrifuge tubes. Processed samples as outlined above.

Example 6: CCK2R Ligand Binding Assay on Cell or Tissue Membranes

Assay Parameters
Tissue Membrane Samples:
Membrane per well: 10 μg
$^3$H-CCK8 concentration: 10 nM
Competitors: L365260 (10 μM): To correct of nonspecific binding; A-71623 (10 μM): To assess potential CCK1R binding
Incubation time: 60 min. at RT
N=3
Materials: Cell or tissue membrane samples; BCA Protein Assay Kit (Pierce); Binding Buffer; BSA; Soybean trypsin inhibitor (STI) 10 mg/mL stock; 0.1% PEI; $^3$H-CCK8, sulfated (Perkin Elmer # NET1162050UC; Lot #1975252 87.9 Ci/mmol; 2.28 μM); L365260 (10 mM stock; Sigma); A-71623 (Tocris); CCK8 (1 mM; purchased from Sigma); Multiscreen$_{HTS}$ FB glass fiber filter plates (Millipore); Multiscreen Vacuum Manifold System (Millipore); Receiver plates (Greiner)

Reagent Preparation
Binding Buffer (KRH Buffer+BSA and STI)
25 mM HEPES, pH 7.4, 104 mM NaCl, 5 mM KCl, 2 mM CaCl$_2$, 1 mM KH$_2$PO$_4$, 1.2 mM MgSO$_4$, 0.1 mg/mL soybean trypsin inhibitor, and 0.2% BSA. Added 2 mg BSA and 10 μL of 10 mg/mL soybean trypsin inhibitor stock per mL of KRH Buffer prior to use.

Wash Buffer
25 mM HEPES, pH 7.4, 0.9% NaCl, 0.2% BSA. 1 L: 5.96 g HEPES (free acid) and 9 g NaCl. Mixed thoroughly to dissolve and adjust pH to 7.4. Added 2 mg of BSA per mL of buffer prior to use.

Procedure
Notes: Keep membrane samples on ice prior to binding assay. Do not let vacuum exceed 135-271 millibar (4-8 in. Hg) during filtration Thawed the membrane samples and determine protein concentration using the BCA Protein Assay Kit. Pre-treated filter plate with 0.1% PEI (100 mg/100 mL) by adding 200 μL per well. Incubated for 60 min at 4° C. Washed 3× with Binding Buffer prior to adding samples to the plate. Diluted membrane samples to the appropriate 4× concentration in Binding Buffer (30 μL needed per well). 4×=400 μg/mL/300 μL each (see attached sheet for dilutions).

Prepared 4× solution of L365260 in Binding Buffer (30 μL needed per well): 40 μM L365260: 40 μL of 1 mM substock+0.960 mL Binding Buffer.

Prepared 4× solution of A-71623 in Binding Buffer (30 μL needed per well): 40 μM A-71623: 40 μL of 1 mM substock+0.960 mL Binding Buffer.

Prepared 4× solution of $^3$H-CCK8 in Binding Buffer (30 μL needed per well): 40 nM $^3$H-CCK8: 56.1 μL of 2.28 μM stock+q.s. 3.144 (1.572×2) mL Binding Buffer Added 30 μL (wells to receive competitors) or 60 μL (non-competed wells) of Binding Buffer to each appropriate well a low-binding 96-well plate. Added 30 μL of 4× competitor (if needed) to each appropriate well. Added 30 μL of the 4×$^3$H-CCK8 solution to each well. Finally, added 30 μL of 4× sample to each well.

Added 120 μL of Binding Buffer to empty wells. Put lid on plate and place on a shaker for 1 h at RT. Transferred 100 μL of samples to pre-treated filter plate. Filtered samples through the plate and collect filtrate. Washed plate 6 times with 150 μL ice cold Wash Buffer. Collect washes. Blotted the bottom of the plate and remove plastic underdrain. Dried plate in overnight at RT.

Removed filters using a 300 μL pipet tip and placed in 3 mL of Ecolite+Scintillation Cocktail. Counted in the LSC and calculate μmol $^3$H-CCK8 bound per mg membrane protein.

Example 7: RNA Purification and Reverse Transcription

Human clinical tissue RNAs were purified from ~50 mg frozen tissues by using RNeasy Plus Universal Mini kit (Qiagen) according to the manufacturer's protocol. Purified RNA samples were treated with DNase to remove contaminated genomic DNAs by using a DNA-free DNA Removal Kit (ambion). RNA concentration was measured by using a Qubit RNA HS Assay Kit (Thermo Fisher). cDNAs were then synthesized by using High-Capacity RNA-to-cDNA Kit (Thermo Fisher) according to the manufacturer's manual. Reaction mixtures without reverse transcriptase were also prepared to be used as negative controls in the following real-time PCR.

Example 8: Real-time PCR

Synthesized cDNA samples were used to examine CCK2R gene expression level by real-time PCR. TissueScan Cancer and Normal Tissue cDNA array (OriGene CSRT103) was also tested to evaluate CCK2R gene expression levels in human normal and tumors tissues. The reaction mix was prepared on ice by mixing 1 ul synthesized cDNA, 1 uL CCKBR probe mixture (Taqman Gene Expression assay: Hs00176123, FAM-MGB design), 10 uL 2× TaqMan Fast Advanced Master Mix, and 8 uL nuclease-free $H_2O$. When Cancer and Normal Tissue cDNA array was examined, 9 uL nuclease-free H2O was first added into each well to dissolve cDNA, then 1 uL probe mixture and 9 uL 2× TaqMan Fast Advanced Master Mix were added and mixed well before qPCR thermal cycles. qPCR was performed on a 7500 Fast Real-Time PCR instrument (Applied Biosystems). The thermal cycling conditions are 95° C. for 20 sec for enzyme activation, then 40 cycles repeat of melting (95° C. for 3 sec) followed by annealing/extension (60° C. for 30 sec). GAPDH gene expression in each sample was also tested at the same time by using Taqman Gene Expression assay (Hs02758991_g1, FAM-MGB design). CCK2R gene expression level was calculated by considering GAPDH expression as 1000 in each sample.

Example 9: Imaging and Internalization of CCK2R Imaging Conjugate

HEK293 cells overexpressing a GFP-tagged version of CCK2R (HEK-CCK2R) were incubated with EC1906 in the presence or absence of competitor (EC1850), and subsequently visualized under a confocal microscope. EC1906 resulted in cellular internalization of CCK2R. See results in FIGS. 11A, 11B, 11C and 11D. EC1906 was effectively competed with excess ligand demonstrating specificity for CCK2R.

What is claimed is:

1. A conjugate of the formula A-L-B, or a pharmaceutically acceptable salt thereof, wherein A is an imaging agent (I), L is a linker, and B is a binding ligand of CCK2R, wherein the conjugate has the formula

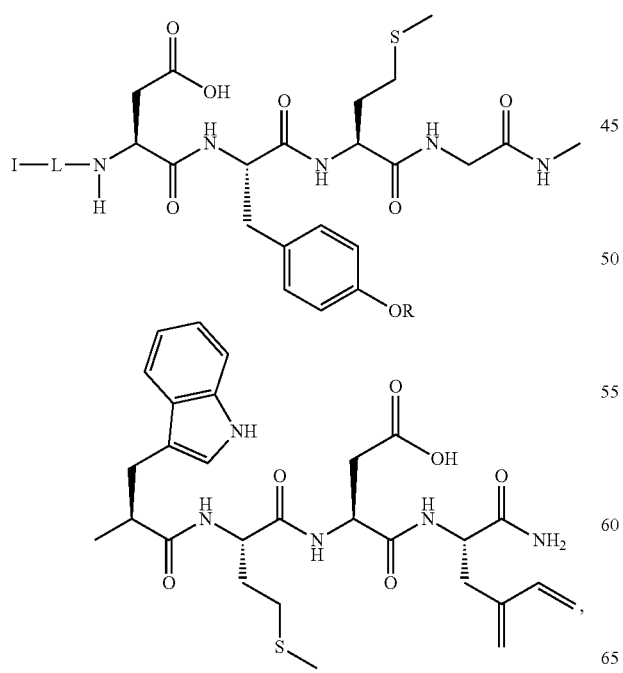

wherein R is H, $SO_3^-$ or $SO_3M$, wherein M is a counter-ion, L is a linker, and I is an imaging agent, and wherein L is of the formula

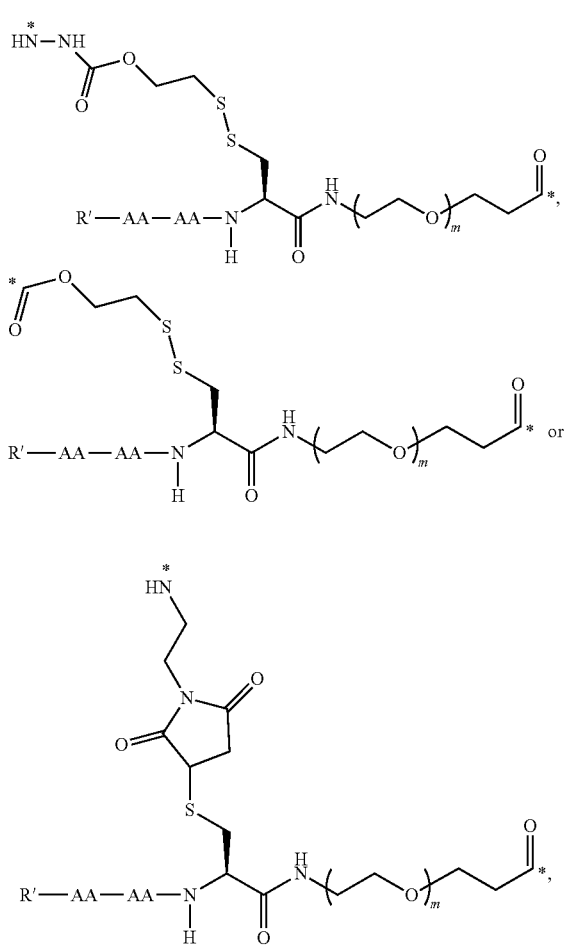

wherein AA is an amino acid, R' is selected from the group consisting of H, $C_1$-$C_6$ alkyl, and —C(O)R", R" is selected from the group consisting of H, $C_1$-$C_6$ alkyl, $C_2$-$C_6$ alkenyl, $C_2$-$C_6$ alkynyl $C_3$-$C_6$ cycloalkyl and $C_6$-$C_{10}$ aryl, m is an integer between 1 and 50, and * is a covalent bond.

2. The conjugate of claim 1, or a pharmaceutically acceptable salt thereof, wherein each amino acid is independently selected from the group consisting of L-asparagine, L-arginine, L-glycine, L-aspartic acid, L-glutamic acid, L-glutamine, L-cysteine, L-alanine, L-valine, L-leucine, L-isoleucine, 3-amino-L-alanine, D-asparagine, D-arginine, D-glycine, D-aspartic acid, D-glutamic acid, D-glutamine, D-cysteine, D-alanine, D-valine, D-leucine, D-isoleucine and 3-amino-D-alanine.

3. The conjugate of claim 1, or a pharmaceutically acceptable salt thereof, wherein each amino acid is independently selected from the group consisting of L-asparagine, L-arginine, L-glycine, L-aspartic acid, L-glutamic acid, L-glutamine, L-cysteine, L-alanine, L-valine, L-leucine, L-isoleucine and 3-amino-L-alanine.

4. The conjugate of claim 1, or a pharmaceutically acceptable salt thereof, of the formula

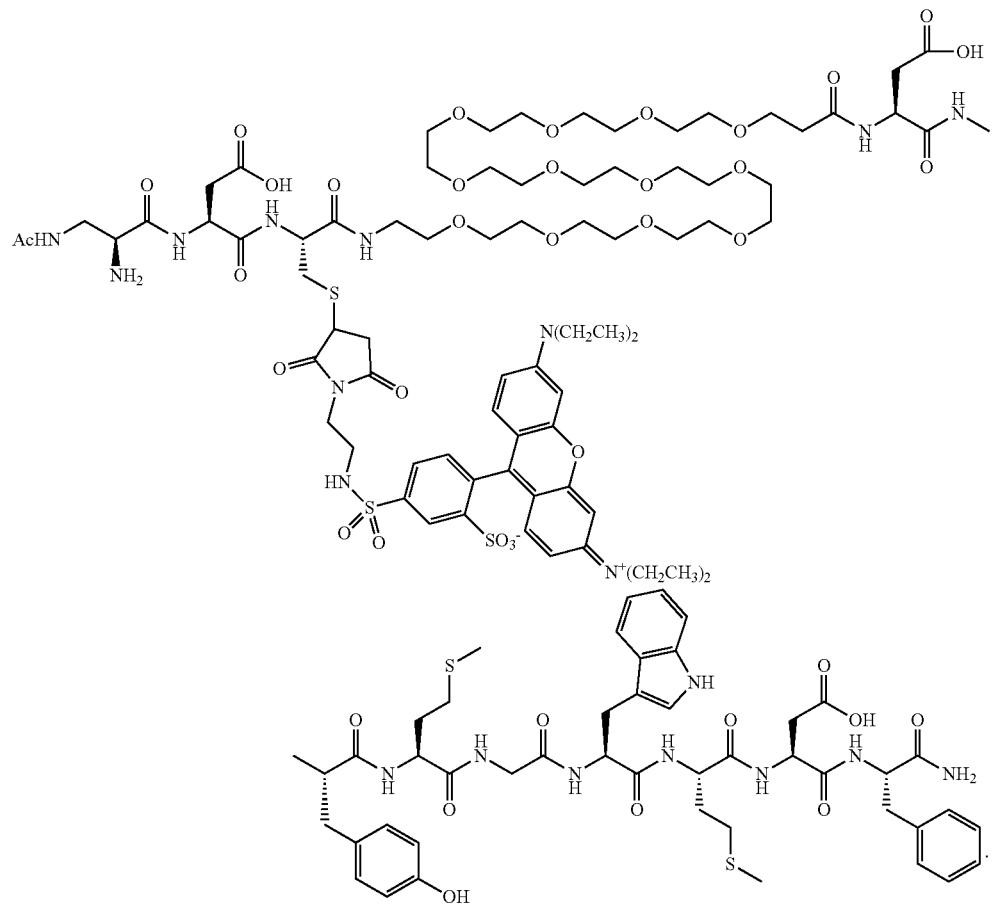
5. A pharmaceutical composition, comprising a conjugate of claim 1, or a pharmaceutically acceptable salt thereof, and optionally at least one excipient.
* * * * *